US008293869B2

(12) United States Patent
Bossard et al.

(10) Patent No.: US 8,293,869 B2
(45) Date of Patent: Oct. 23, 2012

(54) POLYMER CONJUGATES OF GLP-1

(75) Inventors: Mary J. Bossard, Madison, AL (US); Zhihao Fang, Madison, AL (US); Tacey X. Viegas, Madison, AL (US); Stewart A. Thompson, Burlingame, CA (US); Mei-chang Kuo, Palo Alto, CA (US)

(73) Assignee: Nektar Therapeutics, San Francisco, CA (US)

( * ) Notice: Subject to any disclaimer, the term of this patent is extended or adjusted under 35 U.S.C. 154(b) by 517 days.

(21) Appl. No.: 12/086,687

(22) PCT Filed: Dec. 18, 2006

(86) PCT No.: PCT/US2006/048181
§ 371 (c)(1),
(2), (4) Date: Nov. 18, 2009

(87) PCT Pub. No.: WO2007/075534
PCT Pub. Date: Jul. 5, 2007

(65) Prior Publication Data
US 2010/0210505 A1    Aug. 19, 2010

Related U.S. Application Data

(60) Provisional application No. 60/751,121, filed on Dec. 16, 2005, provisional application No. 60/751,082, filed on Dec. 16, 2005.

(51) Int. Cl.
*A61K 38/26*        (2006.01)
*A61K 38/00*        (2006.01)
*C07K 1/00*         (2006.01)

(52) U.S. Cl. ............................ 530/308; 530/324; 530/345
(58) Field of Classification Search .................. None
See application file for complete search history.

(56) References Cited

U.S. PATENT DOCUMENTS

| | | | |
|---|---|---|---|
| 4,667,668 A | 5/1987 | Wetterlin | |
| 4,668,218 A | 5/1987 | Virtanen | |
| 4,805,811 A | 2/1989 | Wetterlin | |
| 4,868,122 A | 9/1989 | Kominek et al. | |
| 5,118,666 A | 6/1992 | Habener | |
| 5,120,712 A | 6/1992 | Habener | |
| 5,320,094 A | 6/1994 | Laube et al. | |
| 5,388,572 A | 2/1995 | Mulhauser et al. | |
| 5,458,135 A | 10/1995 | Patton et al. | |
| 5,522,385 A | 6/1996 | Lloyd et al. | |
| 5,523,549 A | 6/1996 | Tenzer | |
| 5,612,460 A | 3/1997 | Zalipsky | |
| 5,672,581 A | 9/1997 | Rubsamen et al. | |
| 5,707,826 A | 1/1998 | Wagner et al. | |
| 5,739,208 A | 4/1998 | Harris | |
| 5,740,794 A | 4/1998 | Smith et al. | |
| 5,767,254 A | 6/1998 | Polt | |
| 5,785,049 A | 7/1998 | Smith et al. | |
| 5,840,900 A | 11/1998 | Greenwald et al. | |
| 5,880,131 A | 3/1999 | Greenwald et al. | |
| 5,908,830 A | 6/1999 | Smith et al. | |
| 5,932,462 A | 8/1999 | Harris et al. | |
| 6,063,138 A | 5/2000 | Hanna et al. | |
| 6,214,966 B1 | 4/2001 | Harris | |
| 6,257,233 B1 | 7/2001 | Burr et al. | |
| 6,348,558 B1 | 2/2002 | Harris et al. | |
| 6,362,254 B2 | 3/2002 | Harris et al. | |
| 6,376,470 B1 | 4/2002 | Greenwald et al. | |
| 6,440,930 B1 | 8/2002 | Rinella, Jr. | |
| 6,506,730 B1 | 1/2003 | Lee et al. | |
| 6,565,885 B1 | 5/2003 | Tarara et al. | |
| 6,720,407 B1 | 4/2004 | Hughes et al. | |
| 6,828,303 B2 | 12/2004 | Kim et al. | |
| 6,849,708 B1 | 2/2005 | Habener | |
| 7,585,837 B2 * | 9/2009 | Shechter et al. | ............... 514/1.1 |
| 8,183,340 B2 * | 5/2012 | Glaesner et al. | ............... 530/308 |
| 2003/0143596 A1 | 7/2003 | Bentley et al. | |
| 2003/0195154 A1 | 10/2003 | Walker et al. | |
| 2004/0235710 A1 | 11/2004 | DeFelippis et al. | |
| 2005/0009988 A1 | 1/2005 | Harris et al. | |
| 2005/0014903 A1 | 1/2005 | Kozlowski et al. | |
| 2005/0118718 A1 | 6/2005 | Bae et al. | |
| 2005/0260259 A1 | 11/2005 | Bolotin | |
| 2006/0293499 A1 * | 12/2006 | Bentley et al. | ................. 528/322 |
| 2010/0184690 A1 * | 7/2010 | Knudsen et al. | ................. 514/12 |

FOREIGN PATENT DOCUMENTS

| | | |
|---|---|---|
| EP | 0129985 | 9/1988 |
| EP | 0467172 | 4/1994 |
| EP | 0472598 | 7/1996 |
| EP | 0946191 | 3/2003 |
| EP | 0699686 | 10/2003 |
| EP | 0619322 | 12/2005 |
| WO | WO 9111457 | 8/1991 |
| WO | 9420069 A1 | 9/1994 |
| WO | WO 9500162 | 1/1995 |
| WO | WO 9632149 | 10/1996 |
| WO | WO 9741031 | 11/1997 |
| WO | WO 9741833 | 11/1997 |
| WO | WO 9808871 | 3/1998 |
| WO | WO 9820895 | 5/1998 |
| WO | WO 9929336 | 6/1999 |
| WO | WO 9943707 | 9/1999 |
| WO | WO 0012116 | 3/2000 |

(Continued)

OTHER PUBLICATIONS

Mooney et al. 2002. BBA 1569:75-80.*

(Continued)

*Primary Examiner* — Shulamith H Shafer
(74) *Attorney, Agent, or Firm* — Mark A. Wilson

(57) ABSTRACT

Conjugates of a GLP-I moiety may be covalently attached to one or more water-soluble polymers. For instance, a GLP-I polymer conjugate may include a GLP-I moiety releasably attached at its N-terminus to a water-soluble polymer. The GLP-I polymer conjugate may include a GLP-I moiety covalently attached to a water-soluble polymer, wherein the GLP-I moiety possesses an N-methyl substituent. The GLP-I polymer conjugate may include a GLP-I moiety covalently attached at a polymer attachment site to a water-soluble polymer, wherein the GLP-I moiety is glycosylated at a site separate from the polymer attachment site.

9 Claims, 12 Drawing Sheets

FOREIGN PATENT DOCUMENTS

| | | |
|---|---|---|
| WO | WO 0034332 | 6/2000 |
| WO | WO 0041548 | 7/2000 |
| WO | WO 0066629 | 11/2000 |
| WO | WO 0112230 | 2/2001 |
| WO | WO 0162827 | 8/2001 |
| WO | 0246227 A2 | 6/2002 |
| WO | WO 03000278 | 1/2003 |
| WO | WO 03058203 | 7/2003 |
| WO | WO 03070805 | 8/2003 |
| WO | WO 2004007427 | 1/2004 |
| WO | WO 2004022004 | 3/2004 |
| WO | WO 2004022629 | 3/2004 |
| WO | WO 2004022630 | 3/2004 |
| WO | WO 2004029081 | 4/2004 |
| WO | WO 2004033723 | 4/2004 |
| WO | WO 2004060406 | 7/2004 |
| WO | WO 2004060965 | 7/2004 |
| WO | WO 2004060966 | 7/2004 |
| WO | WO 2004060967 | 7/2004 |
| WO | WO 2004074315 | 9/2004 |
| WO | WO 2004078777 | 9/2004 |
| WO | WO 2004089280 | 10/2004 |
| WO | WO 2004093823 | 11/2004 |
| WO | 2005014035 A2 | 2/2005 |
| WO | WO 2005027978 | 3/2005 |
| WO | 2005058954 A1 | 6/2005 |
| WO | WO 2005058955 | 6/2005 |
| WO | WO 2005065714 | 7/2005 |
| WO | WO 2005097158 | 10/2005 |
| WO | WO 2005099768 | 10/2005 |
| WO | WO 2006010143 | 1/2006 |
| WO | WO 2006014673 | 2/2006 |
| WO | WO 2006037810 | 4/2006 |
| WO | WO 2006091506 | 8/2006 |
| WO | 2006124529 A1 | 11/2006 |
| WO | WO 2006138572 | 12/2006 |

OTHER PUBLICATIONS

Haviv et al. 1993. J. Med Chem. 36:363-369.*

Office Communication corresponding to European Patent Application No. 06 847 728.0-1216, dated Jul. 20, 2010.

Chou, et al., "A Radioimmunoassay for LY315902, an analog of Glucagon-like Insulinotropic Peptide, and Its Application in the Study of Canine Pharmacokinetics", J. of Pharm. Sci., vol. 86, No. 7, pp. 768-773, (Jul. 1997).

Dillon, et al., "Cloning and functional expression of the human glucagon-like peptide-1 (GLP-1) receptor", Endocrinology, vol. 133, No. 4, pp. 1907-1910, (1993).

Doores, et al., "Direct deprotected glycosyl-asparagine ligation", Chem. Commun., pp. 1401-1403, (2006).

Drucker, "Biological Actions and Therapeutic Potential of the Glucagon-like Peptides", Gastroenterology, vol. 122, pp. 531-544, (2002).

Drucker, "Development of Glucagon-Like Peptide-1-Based Pharmaceuticals as Therapeutic Agents for the Treatment of Diabetes", Curr. Pharm. Des., vol. 7, pp. 1399-1412, (2001).

Drucker, "Glucagon-Like Peptides", Diabetes, vol. 47, pp. 159-169, (Feb. 1998).

Dugas, et al., "Bioorganic Chemistry: A Chemical Approach to Enzyme Action", Springer Verlag, NY, pp. 54-92, (1981).

Edwards, et al., "Exendin-4 reduces fasting and postprandial glucose and decreases energy intake in healthy volunteers", Am. J. Physiol. Endocrinol. Metab., vol. 281, pp. E155-E161, (2001).

Gallwitz, et al., "GLP-1-analogues resistant to degradation by dipeptidyl-peptidase IV in vitro", Reg. Peptides, vol. 86, pp. 103-111, (2000).

Goke, et al., "Exendin-4 Is a High Potency Agonist and Truncated Exendin-(9-39)-amide an Antagonist at the Glucagon-like Peptide 1-(7-36)-amide Receptor of Insulin-secreting β-Cells", The J. of Bio. Chem., vol. 268, No. 26, Issue of Sep. 15, pp. 19650-19655, (1993).

Gonda, "Physio-chemical principles in aerosol delivery", in Topics in Pharm. Sci., (1991), Crommelin & Midha eds., Medpharm. Sci. Pub., Struttgart, pp. 95-117, (1992).

Gutniak, et al., "Antidiabetogenic Effect of Glucagon-Like Peptide-1 (7-36) Amide in Normal Subjects and Patients with Diabetes Mellitus", The New Eng. J. of Med., vol. 326, pp. 1316-1322, (May 14, 1992).

Harris & Zalipsky, Eds., "Poly(Ethylene Glycol Chemistry: Biotechnical and Biomedical Applications", ACS, Washington, pp. 127-137, (1992).

Kieffer, et al., "Degradation of Glucose-Dependent Insulinotropic Polypeptide and Truncated Glucagon-Like Peptide 1 In Vitro and In Vivo by Dipeptidyl Peptidase IV", Endocrinology, vol. 136, No. 8, pp. 3585-3596, (1995).

Kim, et al., "Development and Characterization of a Glucagon-Like Peptide 1-Albumin Conjugate", Diabetes, vol. 52, pp. 751-759, (Mar. 2003).

Lee, et al., "Synthesis Characterization, and Pharmacokinetic Studies of PEGylated Glucagon-like Peptide-1", Bioconj. Chem., vol. 16, pp. 377-382, (2005).

Merrifield, et al., "Solid Phase Peptide Synthesis. I. The Synthesis of a Tetrapeptide", J. Am. Chem. Soc., vol. 85, No. 14, pp. 2149-2154, (May 1, 2002).

Nauck, et al., "Preserved Incretin Activity of Glucagon-like Peptide 1 [7-36 Amide] but Not of Synthetic Human Gastric Inhibitory Polypeptide in Patients with Type-2 Diabetes Mellitus", J. Clin. Invest., vol. 91, pp. 301-307, (Jan. 1993).

Ouchi, et al., "Design of Antitumor Agent-Terminated Poly(Ethylene Glycol) Conjugate as a Macromolecular Prodrug", Polymer Preprints, vol. 38, No. 1, pp. 582-583, (1997).

Pasut, et al., "Protein, peptide and non-peptide drug PEGylation for Therapeutic application", Exp. Opinion, vol. 14, No. 6, pp. 859-894, (2004).

Rau, et al., "Transiently PEGylated GLP-1 Conjugates: In vitro-in vivo Correlation of Linker-Controlled Cleavage Kinetics", CRS Meeting, 2 pages, (2006).

Roberts, et al., "Chemistry for peptide and protein PEGylation", Adv. Drug Del. Rev., vol. 54, pp. 459-476, (2002).

Sims, et al., "A Method for the Estimation of Polyethylene Glycol in Plasma Protein Fractions", Anal. Biochem., vol. 107, pp. 60-63, (1980).

Stewart, et al., "Solid Phase Peptide Synthesis", W.H. Freeman and Company, pp. 24-66, (1969).

Veronese, et al., "PEG Peptide and Protein Drug Delivery: A Procedure to Identify the PEGylation Site", Cont. Rel. Soc., 2 pages, (1999).

Veronese, et al., "Peptide and Protein PEGylation", Adv. Drug Del. Rev., vol. 54, No. 4, pp. 453-609, (Jun. 17, 2002).

Young, et al., "Glucose-Lowering and Insulin-Sensitizing Actions of Exendin-4", Diabetes, vol. 48, pp. 1026-1034, (May 1999).

Zalipsky, "Chemistry of polyethylene glycol conjugates with biologically active molecules", Adv. Drug Del. Rev., vol. 16, pp. 157-182, (1995).

Zalipsky, et al., "Use of Functionalized Poly(Ethylene Glycol)s for Modification of Polypeptides", Plenum Press, NY, pp. 347-370, (1992).

Zander, et al., "Effect of 6-week course of glucagon-like peptide 1 on glycaemic control, insulin sensitivity, and β-cell function in type 2 diabetes: a parallel-group study", The Lancet, vol. 359, pp. 824-830, (Mar. 9, 2002).

Enzon Pharmaceuticals, Macromolecular Engineering Technologies, pp. 1-14, (2004).

Nektar—Transforming Therapeutics, Nektar Molecule Engineering: Polyethylene Glycol and Derivatives for Advanced PEGylation, pp. 1-20, (Catalog—2003).

Nektar—Transforming Therapeutics, Nektar Advanced PEGylation: Polyethylene Glycol and Derivatives for Advanced PEGylation, pp. 1-24, (Catalog—2004).

NOF Corporation, "PEG Derivatives, Phospholipid and Drug Delivery Materials for Pharmaceuticals", pp. 1-46, (Catalogue 2003—1st).

NOF Corporation, "PEG Derivatives, Phospholipid and Drug Delivery Materials for Pharmaceuticals", pp. 1-50, (Catalogue 2003—2nd).

NOF Corporation, "PEG Derivatives, Phospholipids and Drug Delivery Materials for Pharmaceutical Products and Formulations", pp. 1-59, (Catalogue Ver. 8—Apr. 2006).

Polypure, Products: PEG amines; PEG acids and amino acids; PEG thiols, and disulfides; BIOTINS, (Apr. 2004).

Polypure, Products; PEG amines; PEG acids and amino acids; PEG thiols and disulfides; BIOTINS, (Apr. 2005).

Quanta Biodesign, Labeling, Derivatization and Crosslinking Reagents for Biological and Related Materials with dPEG, pp. 1-38, (Mar. 12, 2004).

Quanta Biodesign, Labeling, Modification and Crosslinking Reagents incorporating our unique monodispersed dPEG Technology, pp. 1-31, (Nov. 5, 2004).

Quanta Biodesign, Ltd., Leading innovator, producer and provider of monodisperse discrete PEG (dPEG) derivatives, (Product Catalog), pp. 1-51, (Updated: Jul. 18, 2005).

Quanta Biodesign, Ltd., Leading innovator, producer and provider of monodisperse discrete PEG (dPEG) derivatives, (Product Catalog), pp. 1-51, (Updated: Nov. 17, 2005).

Shearwater Polymers, Inc., pp. 2-49, (Catalog—Mar. 1995).

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—2000).

Shearwater Corporation, Polyethylene Glycol and Derivatives for Biomedical Applications, pp. 1-17, (Catalog—2001).

European Examination Report In EP Application No. 06 847 728.0 date May 12, 2009.

PCT Internationl Search Report in PCT Application No. PCT/US2006/048181 mail date Sep. 25, 2007.

PCT International Preliminary Report on Patentability in PCT Application No. PCT/US2006/048181 date of issuance of report Jun. 18, 2008.

Zlokarnik, et al., "Quantitation of Transcription and Clonal Selection of Single Living Cells with β-Lactamase as Reporter", Science, vol. 279, pp. 84-88, (Jan. 2, 1998).

* cited by examiner

SEQUENCE LISTING

<160> NUMBER OF SEQ ID NOS: 4

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2

```
<211> LENGTH: 31
<212> TYPE: PRT
<213> ORGANISM: Homo sapiens

<400> SEQUENCE: 2

His Ala Glu Gly Thr Phe Thr Ser Asp Val Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 39
<212> TYPE: PRT
<213> ORGANISM: Heloderma horridum

<400> SEQUENCE: 3

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Heloderma horridum
<220> FEATURE:
<221> NAME/KEY: MISC_FEATURE
<222> LOCATION: (39)..(39)
<223> OTHER INFORMATION: Amidation

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

POLYMER CONJUGATES OF GLP-1

CROSS-REFERENCE TO RELATED APPLICATIONS

This application is a 35 USC §371 application of International Application No. PCT/US2006/048181, filed Dec. 18, 2006, which claims priority to U.S. Application No. 60/751,121, filed Dec. 16, 2005, and to U.S. Application No. 60/751,082, filed Dec. 16, 2005, all of which are hereby incorporated by reference in their entireties. The present application expressly incorporates by reference herein the entire disclosure of U.S. Provisional Patent Application No. 60/691,516, filed Jun. 16, 2005.

FIELD OF THE INVENTION

The present invention relates generally to pharmaceuticals. For instance, the present invention relates to conjugates comprising a GLP-1 (glucagon-like peptide-1) moiety covalently attached to one or more water-soluble polymers. Among other things, the invention additionally relates to methods for synthesizing GLP-1 polymer conjugates, compositions comprising such conjugates, and methods for treating patients by administering GLP-1 conjugates.

This application contains a Sequence Listing appendix, provided as a paper copy, as required under 37 CFR §1.821(c), and is herein incorporated by reference in its entirety, as required by 37 CFR §1.52(e)(5). A copy of the sequence listing is also provided as required under 37 CFR §1.821(e), as a Computer Readable Form (CFR) on a diskette.

BACKGROUND OF THE INVENTION

Glucagon-like-peptide-1 (referred to hereinafter as GLP-1) is a proglucagon-derived peptide secreted from intestinal L-cells in response to nutrient ingestion (Drucker, D J: *The Glucagon-Like Peptides*. Diabetes 47:159-169, 1998). GLP-1 acts as an incretin to stimulate the release of insulin from pancreatic beta cells in conjunction with carbohydrates that are absorbed from the gut. GLP-1 also exerts actions independent of islet hormone secretion, including inhibition of both gastric emptying and food intake and stimulation of β-cell proliferation.

Significantly, GLP-1 possesses the ability to rapidly lower glucose levels in both normal and diabetic subjects (Gutniak, M., et al., *N Engl J Med* 326:1316-1322, 1992; Nauck M A, et al., *J Clin Invest* 91:301-307, 1993). In a six-week study in humans, continuous subcutaneous infusion of native GLP-1 significantly decreased blood glucose and $HbA_{1c}$ in patients with type 2 diabetes (Zander M, et al., *Lancet* 359:824-830, 2002). Based on results such as these, there has been considerable interest in developing GLP-1 based pharmaceutical agents for the treatment of type-2 diabetes and the like.

Although native GLP-1 effectively lowers blood glucose following administration, its usefulness as a therapeutic agent is severely hampered due to the fact that native GLP-1 (amino acids 1-37) is poorly active, and its two naturally-occurring truncated versions, GLP-1 (7-37) and GLP-1 (7-36)$NH_2$, have extremely short in vivo half-lives. The short in vivo half-life of GLP-1 is due primarily to $NH_2$-terminal cleavage and inactivation by the enzyme, dipeptidyl peptidase, DPP-IV (Kieffer T J et al., *Endocrinology* 136:3585-3596, 1995).

Various approaches have been explored to attempt to circumvent the rapid in vivo cleavage of GLP-1 by DPP-IV. For example, GLP-1 analogs having one or more amino acid substitutions aimed at reducing the affinity of GLP-1 for DPP-IV to attenuate its cleavage have been prepared (Drucker D J, *Curr Pharm Des* 7:1399-1412, 2001; Drucker D J, *Gastroenterology* 122:531-544, 2002). Similarly, the naturally-occurring lizard peptide, exendin-4, has been found to be a potent GLP-1R agonist that exhibits reduced DPP-IV mediated cleavage and possesses a longer duration of action than GLP-1 (Young, A A, et al., *Diabetes* 48:1026-1034, 1999; Edwards C M, et al., *Am J Physiol Endicrinol Metab* 281:E155-161, 2001). GLP-1 derivatives having a short covalent chemical linker designed to interact with a specific cysteine residue in albumin following administration have also been developed (Kim, J G, et al., *Diabetes* 52, 751, 2003), as have GLP-1 analogs having several modifications including a modified N-terminus, an octanoic acid acylated at lysine-34, and a substitution of arginine at position 26 (Chou, J., et al., *J. Pharm Sci*, 86 (7), 768-773, 2000). Additionally, stable covalent attachment of polyethylene glycol to GLP-1 has been described (See, e.g., WO 2004/093823).

While these and other various approaches appear to describe GLP-1 compounds having improved therapeutic properties when compared to native GLP-1, there still exists a need for improved GLP-1 compounds capable of providing additional therapeutic advantages over existing GLP-1 based therapeutic agents. Thus, there remains a need in the art to provide additional advantageous GLP-1 moiety-polymer conjugates. Among other things, one or more embodiments of the present invention are therefore directed to such conjugates as well as compositions comprising the conjugates and related methods as described herein.

SUMMARY OF THE INVENTION

Accordingly, the present invention provides GLP-1 conjugates. Other features and advantages of the present invention will be set forth in the description of invention that follows, and in part will be apparent from the description or may be learned by practice of the invention. The invention will be realized and attained by the compositions and methods particularly pointed out in the written description and claims hereof.

One aspect of the present invention is directed to a GLP-1 polymer conjugate comprising a GLP-1 moiety releasably attached at its N-terminus to a water-soluble polymer.

Another aspect of the present invention is directed to a pharmaceutical composition comprising at least an effective amount of a mixture of positional isomers of GLP-1 mono-polymer conjugates having a single water-soluble polymer releasably attached to a GLP-1 moiety, wherein one of the mono-polymer conjugates possesses the water-soluble polymer covalently attached to the N-terminus of the GLP-1 moiety.

Yet another aspect of the present invention is directed to a pharmaceutical composition comprising at least an effective amount of a mixture of GLP-1 polymer conjugates, wherein at least one GLP-1 polymer conjugate possesses a water-soluble polymer releasably attached to a GLP-1 moiety at its N-terminus.

Still another aspect of the present invention is directed to a method for preparing a GLP-1 polymer conjugate, the method comprising contacting a GLP-1 moiety with a water-soluble polymer reagent comprising an amino-reactive functional group suitable to form a hydrolyzable linkage, under conjugation conditions effective to promote reaction of the N-terminal amino group of the GLP-1 moiety with the amino-reactive functional group of the water-soluble polymer reagent, to thereby form a GLP-1 polymer conjugate comprising the GLP-1 moiety releasably attached at its N-terminus to the water-soluble polymer.

In another aspect the present invention is directed to a method for treating a condition in a mammalian subject responsive to treatment with GLP-1, the method comprising administering to the subject, a GLP-1 polymer conjugate comprising a GLP-1 moiety releasably attached to a water-soluble polymer, wherein the conjugate lacks bioactivity prior to the administering, and whereby, as a result of the administering, the GLP-1 moiety is released from the conjugate and is effective to result in a reduction in blood glucose level in the subject over a period of time prolonged over that observed for native GLP-1.

In yet another aspect the present invention is directed to a GLP-1 polymer conjugate comprising a GLP-1 moiety covalently attached to a water-soluble polymer, wherein the GLP-1 moiety possesses an N-methyl substituent.

In still another aspect the present invention is directed to a GLP-1 polymer conjugate comprising a GLP-1 moiety covalently attached at a polymer attachment site to a water-soluble polymer, wherein the GLP-1 moiety is glycosylated at a site separate from the polymer attachment site.

In another aspect the present invention is directed to a composition, comprising a glycosylated and pegylated GLP-1 conjugate made by stepwise solid phase peptide synthesis involving contacting a growing peptide chain with protected amino acids in a stepwise manner, wherein at least one of the protected amino acids is glycosylated, followed by pegylation, and wherein the composition has a purity of at least about 95% of a single species of the glycosylated and pegylated GLP-1 conjugate.

In yet another aspect the present invention is directed to a method of making a glycosylated GLP-1 polymer conjugate. The method includes contacting a growing peptide chain with protected amino acids in a stepwise manner, wherein at least one of the protected amino acids is glycosylated prior to contacting, under conditions effective to form a glycosylated GLP-1. The method also includes contacting the glycosylated GLP-1 with a water-soluble polymer reagent under conjugation conditions effective to form the glycosylated GLP-1 polymer conjugate comprising a glycosylated GLP-1 moiety attached to the water-soluble polymer.

In still another aspect the present invention is directed to a GLP-1 polymer conjugate having the structure:

$$POLY^1-X^1 \diagdown_{Ar} \diagdown \begin{matrix} R^1 \\ | \\ C \\ | \\ R^2 \\ | \\ H_\alpha \end{matrix} - Y^1 - \overset{\overset{Y^2}{\|}}{C} - NH\text{-}GLP\text{-}1$$

$$POLY^2-X^2 \diagup$$

wherein:
POLY$^1$ is a first water-soluble polymer;
POLY$^2$ is a second water-soluble polymer;
X$^1$ and X$^2$ are each independently a spacer moiety having an atom length of from about 1 to about 18 atoms;

$$\diagdown_{Ar} \diagdown H_\alpha$$

is an aromatic-containing moiety bearing an ionizable hydrogen atom, H$_\alpha$;

R$^1$ is H or a lower alkyl;
R$^2$ is H or a lower alkyl;
Y$^1$ is O or S;
Y$^2$ is O or S; and
—NH-GLP-1 is a GLP-1 moiety, wherein the —NH— of —NH-GLP-1 represents an amino group of the GLP-1 moiety.

In yet another aspect the present invention is directed to a GLP-1 polymer conjugate having the structure:

$$POLY^1-X^1-Ar^1 \diagdown \begin{matrix} R^1 \\ | \\ C \\ | \\ C \\ | \\ R^2 \\ | \\ H_\alpha \end{matrix} -Y^1- \overset{\overset{Y^2}{\|}}{C} -NH\text{-}GLP\text{-}1$$

$$POLY^2-X^2-Ar^2 \diagup$$

wherein:
POLY$^1$ is a first water-soluble polymer;
POLY$^2$ is a second water-soluble polymer;
X$^1$ and X$^2$ are each independently a spacer moiety having an atom length of from about 1 to about 18 atoms;
Ar$^1$ is a first aromatic moiety;
Ar$^2$ is a second aromatic moiety;
H$\alpha$ is an ionizable hydrogen atom;
R$^1$ is H or a lower alkyl;
R$^2$ is H or a lower alkyl;
Y$^1$ is O or S;
Y$^2$ is O or S; and
—NH-GLP-1 is a GLP-1 moiety, wherein the —NH— of —NH-GLP-1 represents an amino group of the GLP-1 moiety.

In another aspect the present invention is directed to a GLP-1 polymer conjugate having the structure:

$$POLY^1-X^1-Ar^1 \diagdown \begin{matrix} R^1 \\ | \\ C \\ | \\ C \\ | \\ R^2 \\ | \\ H_\alpha \end{matrix} -Y^1- \overset{\overset{Y^2}{\|}}{C} -NH\text{-}GLP\text{-}1$$

$$POLY^2-X^2-Ar^2 \diagup$$

wherein:
POLY$^1$ is a first water-soluble polymer;
POLY$^2$ is a second water-soluble polymer;
X$^1$ and X$^2$ are each independently a spacer moiety having an atom length of from about 1 to about 18 atoms;
Ar$^1$ is a first aromatic moiety;
Ar$^2$ is a second aromatic moiety;
H$\alpha$ is an ionizable hydrogen atom;
R$^1$ is H or a lower alkyl;
R$^2$ is H or a lower alkyl;
Y$^1$ is O or S;
Y$^2$ is O or S; and
—NH-GLP-1 is a GLP-1 moiety, wherein the —NH— of —NH-GLP-1 represents an amino group of the GLP-1 moiety.

In still another aspect the present invention is directed to a GLP-1 polymer conjugate having the structure:

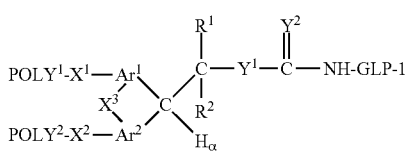

wherein:
POLY$^1$ is a first water-soluble polymer;
POLY$^2$ is a second water-soluble polymer;
X$^1$, X$^2$, and X$^3$ are each independently a spacer moiety having an atom length of from about 1 to about 18 atoms;
Ar$^1$ is a first aromatic moiety;
Ar$^2$ is a second aromatic moiety;
H$\alpha$ is an ionizable hydrogen atom;
R$^1$ is H or a lower alkyl;
R$^2$ is H or a lower alkyl;
Y$^1$ is O or S;
Y$^2$ is O or S; and
—NH-GLP-1 is a GLP-1 moiety, wherein the —NH— of —NH-GLP-1 represents an amino group of the GLP-1 moiety.

Accordingly, in one aspect, the invention provides extended delivery compositions comprising a GLP-1 moiety. The conjugates and compositions of the invention typically possess extended release properties in vitro and in vivo. In vivo animal model data presented herein suggests that the GLP-1 conjugates of the invention can possess a longer circulating half-life in the bloodstream than native GLP-1, thereby overcoming some of the drawbacks associated with therapeutic administration of native GLP-1 due to its rapid clearance.

Thus, the conjugates and compositions described herein may facilitate a decreased frequency of dosing compared to native GLP-1.

For example, in one or more embodiments, a GLP-1 polymer conjugate of the invention is releasable, e.g., is effective to release the GLP-1 moiety, e.g., by a degradative process such as hydrolysis. Such releasable conjugates will comprise at least one degradable linkage, such as a hydrolyzable linkage, between the GLP-1 moiety and the water-soluble polymer.

In one or more embodiments, the water-soluble polymer is selected from the group consisting of poly(alkylene glycols), poly(oxyethylated polyols), poly(olefinic alcohols), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), and copolymers and terpolymers thereof.

In some preferred embodiments, the water-soluble polymer is a polyethylene glycol.

A GLP-1 polymer conjugate of the invention may additionally comprise at least one additional water-soluble polymer such as polyethylene glycol releasably attached to a number of sites on the GLP-1 moiety selected from one and two. Such exemplary sites on the GLP-1 moiety include Lys26 and Lys34, among others.

In one or more embodiments, the GLP-1 polymer conjugate possesses the water-soluble polymer, e.g., polyethylene glycol, releasably attached to a single site of the GLP-1 moiety.

In yet one or more embodiments, the water-soluble polymer is releasably attached to the GLP-1 moiety via a linker comprising a hydrolyzable linkage selected from carbamate, carboxylate ester, phosphate ester, anhydride, acetal, ketal, acyloxyalkyl ether, imine, orthoester, thioester, thiolester, and carbonate. Particularly preferred linkages include carbamate, carboxylate ester, and carbonate.

In yet one or more additional embodiments, a GLP-1 conjugate of the invention comprises a GLP-1 moiety releasably attached, e.g., via a hydrolyzable linkage, to a water-soluble polymer such as PEG, such that upon hydrolysis either in vitro or in vivo, the unconjugated GLP-1 moiety is released. Due to the hydrolyzable nature of such conjugates, a GLP-1 conjugate of the invention may or may not be bioactive.

Thus, in one or more embodiments, a GLP-1 polymer conjugate is provided where the conjugate essentially lacks bioactivity, yet is still effective, when administered in vivo to a mammalian subject in need thereof, to provide a blood glucose-lowering effect. Such blood glucose lowering is achieved by release of the GLP-1 moiety subsequent to administration.

In one or more embodiments, the water-soluble polymer has a molecular weight ranging from about 500 daltons to about 80,000 daltons, such as from about 1000 daltons to about 40,000 daltons.

In yet one or more additional embodiments, the water-soluble polymer has a structure selected from linear, branched, forked, and multi-armed.

In yet one or more further embodiments, the GLP-1 moiety is glycosylated.

In a preferred embodiment, the glycosylated GLP-1 possesses a mono-, di-, or trisaccharide covalently attached to one or more of its amino acid sites. For example, the mono-, di-, or trisaccharide may be covalently attached to one or more sites of the GLP-1 moiety, wherein the one or more sites each comprise one of Asp, Asn, Ser, and Thr that is naturally occurring or substituted at one or more sites selected from the N-terminus (His7), Ala8, Glu9, Thr11, Thr13, Ser14, Ser17, Ser18, Glu21, Gly22, Gln23, Lys26, and Lys34.

In yet one or more additional embodiments, a GLP-1 polymer conjugate possesses a mono-, di-, or trisaccharide covalently attached to one of Asp, Asn, Ser, and Thr that is substituted at the Ala8 site of the GLP-1 moiety. Illustrative saccharides include glucose, mannose, xylose, lactose, maltose, melibiose, and maltotriose. Such GLP-1 polymer conjugates may further comprise a mono-, di- or trisaccharide covalently attached at one or both of positions Glu21 and Gln23.

In yet one or more further embodiments, the GLP-1 polymer conjugate possesses an N-methyl substituent at any one or more of positions 7-His, 8-Ala, and 9-glutamic acid of the GLP-1 moiety.

In one or more embodiments, a GLP-1 polymer conjugate possesses the following structure:

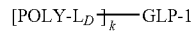

where POLY is a water-soluble polymer, L$_D$ is a degradable linkage, e.g., a hydrolyzable linkage, and k corresponds to the number of reactive sites on GLP-1 to which an independent polymer segment (POLY-L$_D$) is covalently attached. GLP-1 is a GLP-1 moiety. Each of the polymer segments is independently selected, although typically, each of the polymer segments covalently attached to the GLP-1 moiety is the same. Typically, k ranges from about 1 to about 4, that is to say, is selected from the group consisting of 1, 2, 3, and 4. Often, k is 1, 2, or 3. In some particular embodiments, k is 1. In yet one or more specific embodiments, L$_D$ is —O—C(O)—NH—.

Generally, the $L_D$ in the above structure possesses a length such as from about 1 to about 20 atoms, from about 2 to about 15 atoms, or from about 3 to about 10 atoms. That is to say, typically, $L_D$ has an overall atom length selected from the group consisting of 1, 2, 3, 4, 5, 6, 7, 8, 9, 10, 11, 12, 13, 14, 15, 16, 17, 18, 19, and 20.

In one or more particular embodiments, a GLP-1 polymer conjugate possesses the following structure:

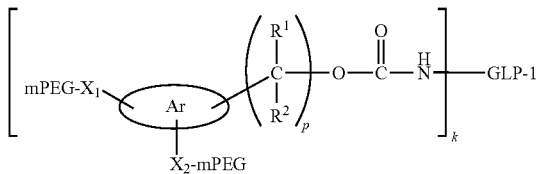

where mPEG is $CH_3O—(CH_2CH_2O)_nCH_2CH_2—$,
n ranges from 10 to 1800,
p is an integer ranging from 1 to 8,
$R_1$ is H or lower alkyl,
$R_2$ is H or lower alkyl,
Ar is an aromatic hydrocarbon, such as a bicyclic or tricylic aromatic,
$X_1$ and $X_2$ are each independently a spacer moiety having an atom length of from about 1 to about 18 atoms, and
—NH-GLP-1 is a GLP-1 moiety, wherein the —NH— of —NH-GLP-1 represents an amino group of the GLP-1 moiety.

In references to the preceding structure, in one or more specific embodiments, p is 1 and $R_1$ and $R_2$ are both H. In yet one or more alternative embodiments, $X_1$ and $X_2$ each comprise at least one amide bond. In yet one or more additional embodiments, $X_1$ and $X_2$ are the same.

In reference to the preceding structure, $X_1$ and $X_2$, may, in certain embodiments, each independently possess a structure selected from —NH—C(O)—CH$_2$—O—, —NH—C(O)—(CH$_2$)$_q$—O—, —NH—C(O)—(CH$_2$)$_q$—C(O)—NH—, —NH—C(O)—(CH$_2$)$_q$—, and —C(O)—NH—, where q is selected from 2, 3, 4, and 5. In yet zone or more further embodiments, Ar is selected from pentalene, indene, naphthalene, indacene, acenaphthylene, and fluorene.

Illustrative GLP-1 polymer conjugates of the invention include the following releasable conjugates:

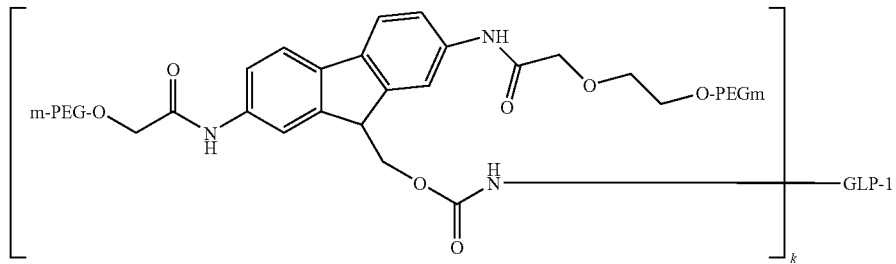

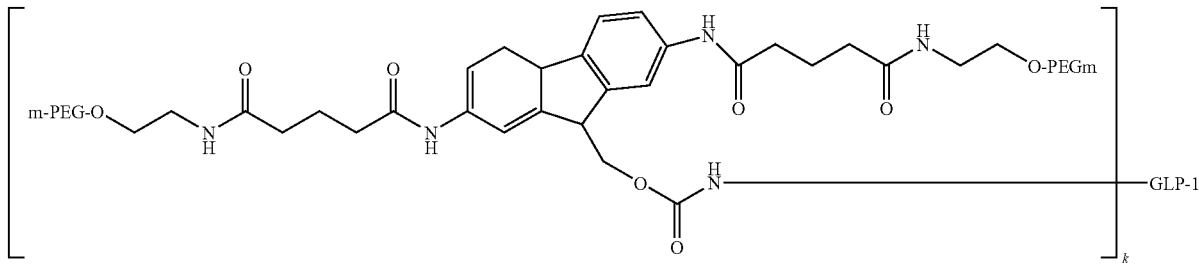

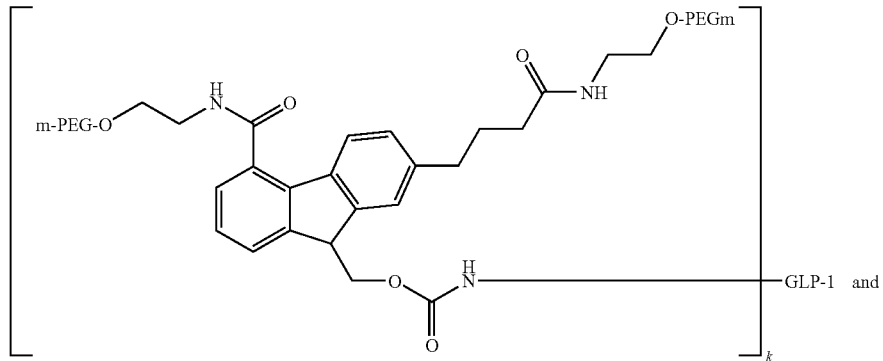

-continued $$\left[ \text{m-PEG-O} \underset{\substack{\text{fluorenyl structure with} \\ \text{amide, NH, O-PEGm, carbamate linker}}}{} \text{GLP-1} \right]_k$$

In yet one or more additional embodiments, a releasable GLP-1 polymer conjugate of the invention possesses the following generalized structure:

$$\left[ \text{POLY-L}_{D1}\text{-Ar}_1\text{—O—}\overset{\text{O}}{\underset{\|}{\text{C}}}\text{—NH} \right]_k \text{—GLP-1}$$

where $L_{D1}$ is either —O— or —NH—C(O)—, $Ar_1$ is an aromatic group, —NH-GLP-1 is a GLP-1 moiety, wherein the —NH— of —NH-GLP-1 represents an amino group of the GLP-1 moiety, and k is selected from 1, 2, and 3. Preferably, $Ar_1$ is selected from ortho, meta, and para-substituted phenyl. Illustrative conjugates of this type include:

In yet one or more alternative embodiments, the pharmaceutical composition comprises, in addition to the GLP-1 conjugate, GLP-1.

Preferred compositions include those suitable for parenteral or pulmonary administration.

In one or more embodiments, a pharmaceutical composition of the invention is in dry powder form.

In one of more particular embodiments, the composition as described above comprises a GLP-1 polymer conjugate having the water-soluble polymer covalently attached, either releasably or stably, to the GLP-1 moiety at the side chain of His7 at the imidazole nitrogen.

As noted above, in certain aspects, the invention provides a method for preparing a GLP-1 polymer conjugate. In certain embodiments, the method further comprises isolating the GLP-1 polymer conjugate.

$$\left[ \text{CH}_3\text{O—(CH}_2\text{CH}_2\text{O)}_n\text{CH}_2\text{CH}_2\text{—O—}\phantom{x}\text{—O—}\overset{\text{O}}{\underset{\|}{\text{C}}}\text{—NH} \right]_k \text{—GLP-1 and}$$

$$\left[ \text{CH}_3\text{O—(CH}_2\text{CH}_2\text{O)}_n\text{CH}_2\text{CH}_2\text{—O—NH—}\overset{\text{O}}{\underset{\|}{\text{C}}}\text{—}\phantom{x}\text{—O—}\overset{\text{O}}{\underset{\|}{\text{C}}}\text{—NH} \right]_k \text{—GLP-1}$$

In yet one or more additional embodiments, a GLP-1 polymer conjugate of the invention is characterized by the following structure:

$$\left[ \text{H}_3\text{C—(OCH}_2\text{CH}_2)_n\text{—O—CH}_2\overset{\text{O}}{\underset{\|}{\text{C}}}\text{—O—}\underset{\underset{\text{CH}_3}{|}}{\text{CHCH}_2}\text{—}\overset{\text{O}}{\underset{\|}{\text{C}}}\text{—NH} \right]_k \text{—GLP-1}$$

where n ranges from about 10 to about 1800.

In one or more related embodiments, the GLP-1 moiety possesses an N-methyl substituent at any one or more of positions 7-His, 8-Ala, and 9-Glu.

Also forming part of the invention is a pharmaceutical composition comprising any one or more of the herein described GLP-1 polymer conjugates, e.g., in combination with a pharmaceutically acceptable excipient.

In one or more embodiments, the pharmaceutical composition comprises, in addition to the GLP-1 conjugate, insulin and/or basal insulin.

In yet one or more additional embodiments, the method further comprises purifying the GLP-1 polymer conjugate. For example, purifying can be by chromatography or membrane separation.

In one or more embodiments of the method, the GLP-1 moiety employed in the contacting step comprises protected ε-amino lysines.

In yet a related embodiment, the method may further comprise subsequent to the contacting, deprotecting the protected ε-amino lysines of the GLP-1 polymer conjugate.

In yet another embodiment, provided herein is an aerosolized composition comprising a GLP-1 polymer conjugate.

As noted above, in certain aspects, the invention provides a method for delivery of a GLP-1 polymer conjugate to a mammalian subject in need thereof.

In one or more related embodiments of this aspect of the invention, the administering is by a route selected from subcutaneous and inhalation.

In yet one or more further embodiments, the administering is by inhalation and the GLP-1 polymer conjugate is in aerosolized form.

Yet in another aspect, the invention provides a method for delivery of a GLP-1 moiety to a mammalian subject in need thereof, where the method comprises pulmonarily administering to the subject a therapeutically effective amount of a GLP-1 polymer conjugate.

In yet another aspect, provided herein is a method for delivering a GLP-1 moiety to a mammalian subject. The method comprises the steps of aerosolizing a pharmaceutical composition comprising a GLP-1 polymer conjugate to form an aerosolized composition, and administering the aerosolized composition to the lungs of the subject by inhalation.

In yet another aspect, provided is a method for treating a condition in a mammalian subject responsive to treatment with GLP-1. The method comprises administering to the subject, a GLP-1 polymer conjugate comprising a GLP-1 moiety releasably attached to a water-soluble polymer, wherein the conjugate lacks bioactivity prior to the administering, and whereby, as a result of the administering, the GLP-1 moiety is released from the conjugate and is effective to result in a reduction in blood glucose level in the subject over a period of time prolonged over that observed for native GLP-1.

In yet another aspect, provided herein is a method of lowering the blood glucose level in a mammalian subject in need thereof, comprising administering to the subject a therapeutically effective amount of a GLP-1 polymer conjugate, to thereby produce lowered blood glucose levels in the subject over an extended period of at least about 8 hours post-administering.

In one or more related embodiments, the method comprises administering a GLP-1 polymer conjugate to such a subject, wherein upon administration, the conjugate is hydrolyzed over a period of several days (e.g., 2-7 days, 2-6 days, 3-6 days, 3-4 days) to thereby release GLP-1 into the bloodstream. The releasable, e.g., hydrolyzable, conjugates are effective, in certain embodiments, to lower blood glucose levels over an extended period of greater than about 48 hours (e.g., for about 1-3 days or so, or for about 1-2.5 days or so).

Also provided herein is the use of a GLP-1 conjugate for the preparation of a medicament to be delivered to the lungs of a mammalian subject, wherein delivery comprises administering the medicament by inhalation for deposition in and absorption from the lung of the subject, for the treatment of diabetes.

The present invention further encompasses a method of stimulating the GLP-1 receptor in a mammalian subject. The method comprises administering to the subject a therapeutically effective amount of a GLP-1 conjugate. The method may be used to treat subjects having a condition selected from non-insulin dependent diabetes, stress-induced hyperglycemia, obesity, gastric and/or intestinal motility or emptying disorders.

Each of the herein-described features of the invention is meant to apply equally to each and every embodiment as described herein, unless otherwise indicated.

Additional objects, advantages and novel features of the invention will be set forth in the description that follows, and in part, will become apparent to those skilled in the art upon reading the following, or may be learned by practice of the invention.

DESCRIPTION OF SEQUENCE LISTING

The following Table describes the amino acid sequences referred to in the Specification.

| Name | SEQ ID NO: | Sequence |
|---|---|---|
| GLP-1 (7-36) | 1 | HAEGTFTSDVSSYLEGQAAKEFIAWLVKGR |
| GLP-1 (7-37) | 2 | HAEGTFTSDVSSYLEGQAAKEFIAWLVKGRG |
| Exendin-3 | 3 | HSDGTFTSDLSKQMEEEAVRLFIEWLKNGGPSSGAPPPS |
| Exendin-4 (C-terminus amidated) | 4 | HGEGTFTSDLSKQMEEEAVRLFIEWLKNGGPSSGAPPPS |

BRIEF DESCRIPTION OF THE FIGURES

The present invention is further described in the description of invention that follows, in reference to the noted plurality of non-limiting drawings, wherein.

DESCRIPTION OF THE INVENTION

Figure 1:
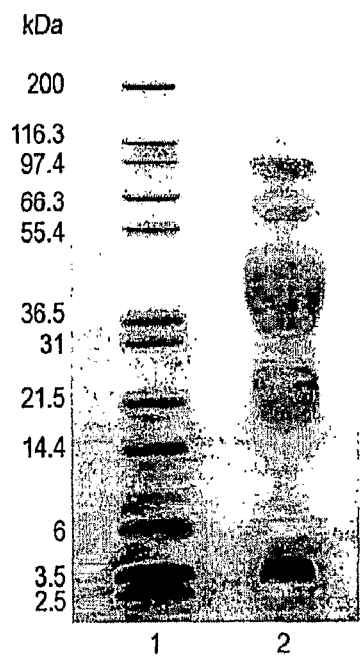
FIG. 1 corresponds to an SDS-PAGE analysis of a G2PEG2Fmoc$_{20K}$-GLP-1 reaction mixture as described in Example 3. Lane 1: Invitrogen Mark 12 unstained standard. Lane 2: G2PEG2Fmoc$_{20K}$-N$^{ter}$-GLP-1 reaction mixture.

Before describing one or more embodiments of the present invention in detail, it is to be understood that this invention is not limited to the particular polymers, synthetic techniques, GLP-1 moieties, and the like, as such may vary.

Unless otherwise stated, a reference to a compound or component includes the compound or component by itself, as well as in combination with other compounds or components, such as mixtures of compounds.

As used in this specification and the claims, the singular forms "a," "an," and "the" include plural referents unless the context clearly dictates otherwise. Thus, for example, reference to "a polymer" includes a single polymer as well as two or more of the same or different polymers, reference to "a pharmaceutically acceptable excipient" refers to a single pharmaceutically acceptable excipient as well as two or more of the same or different pharmaceutically acceptable excipients, and the like.

In describing and claiming the present invention(s), the following terminology will be used in accordance with the definitions provided below.

"PEG," "polyethylene glycol" and "poly(ethylene glycol)" as used herein, are interchangeable. Typically, PEGs for use in accordance with the invention comprise the following structure: "—(OCH$_2$CH$_2$)$_n$—" where (n) is 2 to 4000. As used herein, PEG also includes "—CH$_2$CH$_2$—O(CH$_2$CH$_2$O)$_n$—CH$_2$CH$_2$—" and "—(OCH$_2$CH$_2$)$_n$O—," depending upon whether or not the terminal oxygens have been displaced. When the PEG further comprises a spacer moiety or a linker covalently attached thereto (to be described in greater detail below), the atoms comprising the spacer moiety or linker, when covalently attached to PEG, do not result in the formation of an oxygen-oxygen bond (i.e., an "—O—O—" or peroxide linkage). Throughout the specification and claims, it should be remembered that the term "PEG" includes structures having various terminal or "end capping" groups. The term "PEG" also means a polymer that contains a majority, that is to say, greater than 50%, of —OCH$_2$CH$_2$— or —CH$_2$CH$_2$O-repeating subunits. With respect to specific forms, the PEG can take any number of a variety of molecular weights, as well as structures or geometries such as "branched," "linear," "forked," "multifunctional," and the like, to be described in greater detail herein.

The terms "end-capped" and "terminally capped" are interchangeably used herein to refer to a terminal or endpoint of a polymer having an end-capping moiety. Typically, although not necessarily, the end-capping moiety comprises a hydroxy or C$_{1-20}$ alkoxy group, such as a C$_{1-10}$ alkoxy group or a C$_{1-5}$ alkoxy group. Thus, examples of end-capping moieties include alkoxy (e.g., methoxy, ethoxy), benzyloxy, as well as aryl, heteroaryl, cyclo, heterocyclo, and the like. The end-capping moiety may include one or more atoms of the terminal monomer in the polymer [e.g., the end-capping moiety "methoxy" in CH$_3$(OCH$_2$CH$_2$)$_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount and/or location of the polymer and/or the moiety (e.g., active agent) to which the polymer is coupled can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like.

"Non-naturally occurring" with respect to a polymer as described herein, means a polymer that in its entirety is not found in nature, i.e., is synthetic. A non-naturally occurring polymer may, however, contain one or more monomers or segments of monomers that are naturally occurring, so long as the overall polymer structure is not found in nature.

The term "water soluble" as in a "water-soluble polymer" is any polymer that is soluble in water at room temperature. The water-soluble polymer is a polymer having a solubility of 1% (w/v) or more in water at 25° C. Typically, a water-soluble polymer will transmit at least about 75%, such as at least about 95%, of light transmitted by the same solution after filtering. On a weight basis, a water-soluble polymer will often be at least about 35% (w/v) soluble in water, such as at least about 50% (w/v) soluble in water, at least about 70% (w/v) soluble in water, or at least about 85% (w/v) soluble in water, at 25° C. Typically, the water-soluble polymer is at least about 95% (w/v) soluble in water or completely soluble in water.

"Hydrophilic", e.g., in reference to a "hydrophilic polymer", refers to a polymer that is characterized by its solubility in and compatibility with water. In non-cross linked form, a hydrophilic polymer is able to dissolve in, or be dispersed in water. Typically, a hydrophilic polymer possesses a polymer backbone composed of carbon and hydrogen, and generally possesses a high percentage of oxygen in either the main polymer backbone or in pendent groups substituted along the polymer backbone, thereby leading to its "water-loving" nature. The water-soluble polymers of the present invention are typically hydrophilic, e.g., non-naturally occurring hydrophilic.

Molecular weight in the context of a water-soluble polymer, such as PEG, can be expressed as either a number-average molecular weight or a weight-average molecular weight. Unless otherwise indicated, all references to molecular weight herein refer to the weight-average molecular weight. Both molecular weight determinations, number-average and weight-average, can be measured using gel permeation chromatographic or other liquid chromatographic techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 1.2, less than about 1.15, less than about 1.10, less than about 1.05, and less than about 1.03. As used herein, references will at times be made to a single water-soluble polymer having either a weight-average molecular weight or number-average molecular weight; such references will be understood to mean that the single water-soluble polymer was obtained from a composition of water-soluble polymers having the stated molecular weight.

The terms "active" or "activated" when used in conjunction with a particular functional group, refer to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage," or "linker" are used herein to refer to an atom or a collection of atoms used to link interconnecting moieties such as a terminus of a polymer and a GLP-1 moiety or an electrophile or nucleophile of a GLP-1 moiety. The spacer moiety may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are often not necessarily saturated and may be branched or straight chain. Straight chain is typical. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched. Non-limiting examples of lower alkyl include methyl, ethyl, n-butyl, i-butyl, and t-butyl.

"Cycloalkyl" refers to a saturated or unsaturated cyclic hydrocarbon chain, including bridged, fused, or Spiro cyclic compounds, such as those made up of 3 to about 12 carbon atoms, or 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, such as $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy; lower phenyl; substituted phenyl; and the like. "Substituted aryl" is aryl having one or more noninterfering substituents. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl and heterocycle.

"Heteroaryl" is an aryl group containing from one to four heteroatoms, such as sulfur, oxygen, or nitrogen, or a combination thereof. Heteroaryl rings may also be fused with one or more cyclic hydrocarbon, heterocyclic, aryl, or heteroaryl rings. As used herein, "heteroaryl" includes substituted heteroaryl.

"Heterocycle" or "heterocyclic" means one or more rings of 5-12 atoms, such as 5-7 atoms, with or without unsaturation or aromatic character and having at least one ring atom that is not a carbon. Heteroatoms include, but are not limited to, sulfur, oxygen, and nitrogen. As used herein, "heterocycle" includes substituted heterocycle.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl, and substituted aryl.

"Electrophile" and "electrophilic group" refer to an ion or atom or collection of atoms that may be ionic, having an electrophilic center, i.e., a center that is electron seeking, capable of reacting with a nucleophile.

"Nucleophile" and "nucephilic group" refer to an ion or atom or collection of atoms that may be ionic having a nucleophilic center, i.e., a center that is seeking an electrophilic center or capable of reacting with an electrophile.

A "hydrolytically degradable" or "hydrolyzable" linkage or bond is a bond that reacts with water (i.e., is hydrolyzed) under physiological conditions. Examples include bonds that have a hydrolysis half-life at pH 8, 25° C. of less than about 30 minutes. The tendency of a bond to hydrolyze in water will depend not only on the general type of linkage connecting two given atoms but also on the substituents attached to the two given atoms. Hydrolytically unstable or degradable linkages include but are not limited to carbamate, carboxylate ester (referred to herein simply as "ester"), phosphate ester, anhydrides, acetals, ketals, acyloxyalkyl ether, imine, orthoester, peptide and oligonucleotide. Hydrolytically degradable linkages exclude linkages in which cleavage of a carrier group becomes effective only after unmasking an activating group, such as disclosed in WO 2005/099768, which is incorporated herein by reference in its entirety. In other words, hydrolytically degradable linkages exclude linkages based on cascade cleavage mechanisms.

"Releasably attached", e.g., in reference to a GLP-1 moiety releasably attached to a water-soluble polymer, refers to a moiety such as a GLP-1 moiety that is covalently attached via a linker that includes a hydrolytically degradable linkage as defined above, wherein upon hydrolysis, the GLP-1 moiety is released. The GLP-1 moiety thus released will typically correspond to the unmodified parent or native GLP-1 moiety, or may be slightly altered, e.g., to possess a short organic tag of no more than about 8 atoms or so, e.g., typically resulting from incomplete cleavage of the water-soluble polymer. Preferably, the unmodified parent GLP-1 moiety is released. In instances in which the water-soluble polymer includes or is covalently attached to the GLP-1 moiety via a linker comprising an aryl group, release of the GLP-1 moiety occurs via a mechanism which involves neither a 1,4- nor a 1,6-elimination step.

An "enzymatically degradable linkage" means a linkage that is subject to degradation by one or more enzymes.

A "hydrolytically stable" linkage or bond refers to a chemical bond, typically a covalent bond, which is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethane, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient" refers to an excipient that may optionally be included in a composition and that causes no significant adverse toxicological effects to a patient upon administration.

A "pharmaceutical composition" is a composition useful for pharmaceutical purposes.

As used herein, "effective amount" refers to an amount covering both therapeutically effective amounts and prophylactically effective amounts.

As used herein, "therapeutically effective amount" refers to an amount that is effective to achieve the desired therapeutic result. For example, an effective amount of a pharmaceutical composition to treat or ameliorate diabetes is an amount sufficient to reduce or eliminate the symptoms of diabetes, for example, an amount that is needed to provide a desired level of insulin in the bloodstream to result in reduced blood glucose. The pharmacologically effective amount of a given pharmaceutical composition will vary with factors such as the nature of the active component in the composition, the route of administration, the size and species of the animal to receive the composition, and the purpose of the administration. The suitable amount can be readily determined by one skilled in the art based upon available literature and the information provided herein.

As used herein, "prophylactically effective amount" refers to an amount that is effective to achieve the desired prophylactic result. Because a prophylactic dose is administered in patients prior to onset of disease, the prophylactically effective amount typically is less than the therapeutically effective amount.

"Multi-functional" means a polymer having three or more functional groups contained therein, where the functional groups may be the same or different. Multi-functional polymeric reagents will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9, or 10 functional groups within the polymer backbone.

The term "GLP-1 moiety," as used herein, refers to a moiety having GLP-1 activity. The GLP-1 moiety will also have at least one electrophilic group or nucleophilic group suitable for reaction with a water-soluble polymer as provided herein.

In addition, the term "GLP-1 moiety" encompasses both the GLP-1 moiety prior to conjugation as well as the GLP-1 moiety residue following conjugation. As will be explained in further detail below, one of ordinary skill in the art can determine whether any given moiety has GLP-1 activity. As used herein, the term "GLP-1 moiety" includes peptides modified deliberately, as for example, by site directed mutagenesis or accidentally through mutations. The term "GLP-1 moiety" includes native GLP-1 (GLP-1 (7-37)OH or GLP-1 (7-36)NH$_2$), GLP-1 analogs, GLP-1 derivatives, GLP-1 biologically active fragments, extended GLP-1 (see, for example, International Patent Publication No. WO 03/058203, which is incorporated herein by reference, in particular with respect to the extended glucagon-like peptide-1 analogs described therein), and exendin-4 analogs and exendin-4 derivatives comprising one or two cysteine residues at particular positions within GLP-1 as described in WO 2004/093823, which is incorporated herein by reference.

"GLP-1" refers to a compound having GLP-1 activity. As used herein, the term "GLP-1" includes peptides modified deliberately, as for example, by site directed mutagenesis or accidentally through mutations. The term "GLP-1" includes native GLP-1 (GLP-1 (7-37)OH or GLP-1 (7-36)NH$_2$), GLP-1 analogs, GLP-1 derivatives, GLP-1 biologically active fragments, extended GLP-1 (see, for example, International Patent Publication No. WO 03/058203, which is incorporated herein by reference, in particular with respect to the extended glucagon-like peptide-1 analogs described therein), and exendin-4 analogs and exendin-4 derivatives comprising one or two cysteine residues at particular positions within GLP-1 as described in WO 2004/093823, which is incorporated herein by reference.

The term "fragment" means any peptide having the amino acid sequence of a portion of a GLP-1 moiety that retains some degree of GLP-1 activity. Fragments include peptides produced by proteolytic degradation of the GLP-1 or produced by chemical synthesis by methods routine in the art. Often, GLP-1 fragments are obtained after truncation of one or more amino acids from the N-terminus and/or C-terminus of a GLP-1 moiety, and possess a degree of GLP-1 activity.

The term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 95 percent homology, equivalent biological properties (although potentiality different degrees of activity), and equivalent expression characteristics are considered substantially homologous. For purposes of determining homology, truncation of the mature sequence should be disregarded. Sequences having lesser degrees of homology, comparable bioactivity, and equivalent expression characteristics are considered substantial equivalents. Exemplary GLP-1 moieties for use herein include those peptides having a sequence that is substantially homologous to, e.g., native GLP-1.

A "deletion variant" of a GLP-1 moiety is a peptide in which one or more amino acid residues of the GLP-1 moiety have been deleted and the amino acid residues preceding and following the deleted amino acid residue are connected via an amide bond (except in instances where the deleted amino acid residue was located on a terminus of the peptide or protein). Deletion variants include instances where only a single amino acid residue has been deleted, as well as instances where two amino acids are deleted, three amino acids are deleted, four amino acids are deleted, and so forth. Each deletion retains some degree of GLP-1 activity.

A "substitution variant" of a GLP-1 moiety is peptide or protein in which one or more amino acid residues of the GLP-1 moiety have been deleted and a different amino acid residue has taken its place. Substitution variants include instances where only a single amino acid residue has been substituted, as well as instances where two amino acids are substituted, three amino acids are substituted, four amino acids are substituted, and so forth. Each substitution variant has some degree of GLP-1 activity.

An "addition variant" of a GLP-1 moiety is a peptide in which one or more amino acid residues of the GLP-1 have been added into an amino acid sequence and adjacent amino acid residues are attached to the added amino acid residue by way of amide bonds (except in instances where the added amino acid residue is located on a terminus of the peptide, wherein only a single amide bond attaches the added amino acid residue). Addition variants include instances where only a single amino acid residue has been added, as well as instances where two amino acids are added, three amino acids are added, four amino acids are added, and so forth. Each addition variant has some degree of GLP-1 activity.

"Insulinotropic activity" refers to the ability to stimulate insulin secretion in response to elevated glucose levels, thereby causing glucose intake by cells and decreased plasma glucose levels. Insulinotropic activity can be measured by methods known in the art, such as by measuring GLP-1 receptor binding activity or activation, e.g., assays employing pancreatic islet cells or insulinoma cells, as described in EP 619 322 and U.S. Pat. No. 5,120,712, respectively, which are incorporated herein by reference. Insulinotropic activity is typically measured in humans by measuring insulin or C-peptide levels.

The terms "subject", "individual," or "patient" are used interchangeably herein and refer to a vertebrate, preferably a mammal. Mammals include, but are not limited to, murines, rodents, simians, humans, farm animals, sport animals, and pets.

"Optional" or "optionally" means that the subsequently described circumstance may or may not occur, so that the description includes instances where the circumstance occurs and instances where it does not.

"Substantially" (unless specifically defined for a particular context elsewhere or the context clearly dictates otherwise) means nearly totally or completely, for instance, satisfying one or more of the following: greater than 50%, 51% or greater, 75% or greater, 80% or greater, 90% or greater, and 95% or greater of the condition.

Unless the context clearly dictates otherwise, when the term "about" precedes a numerical value, the numerical value is understood to mean f 10% of the stated numerical value.

"Amino acid" refers to any compound containing both an amino group and a carboxylic acid group. Although the amino group most commonly occurs at the position adjacent to the carboxy function, the amino group may be positioned at any location within the molecule. The amino acid may also contain additional functional groups, such as amino, thio, carboxyl, carboxamide, imidazole, etc. An amino acid may be synthetic or naturally occurring, and may be used in either its racemic or optically active (D-, or L-) form.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

A "sustained release composition" or an "extended release composition" is a composition that releases the active component slowly over a relatively longer period of time than an "immediate release" composition. In general, the active component, e.g., GLP-1 polymer conjugate, is released over at least about 3 hours, or at least about 4 hours, or at least about 5 hours, or at least about 6 hours, or at least about 8 hours.

A "sustained plasma level" of a protein for a specified period of time means that the protein can be detected in the plasma for a duration specified. A protein can be detected by any methods for detecting such protein, e.g., immunological, biochemical, or functional methods. For example, insulin can be detected by enzyme-linked immunosorbent assay (ELISA), mass spectrometry, or determination of blood glucose levels.

A composition that is "suitable for pulmonary delivery" refers to a composition that is capable of being aerosolized and inhaled by a subject so that a portion of the aerosolized particles reaches the lungs to permit penetration into the alveoli. Such a composition may be considered "respirable" or "inhalable."

An "aerosolized" composition contains liquid or solid particles that are suspended in a gas (typically air), typically as a result of actuation (or firing) of an inhalation device such as a dry powder inhaler, an atomizer, a metered dose inhaler, or a nebulizer.

A "jet nebulizer" is a system, such as a device, that forces compressed air through a solution of a drug so that a fine spray can be delivered to a facemask and inhaled. Nebulizers often are used to administer drugs to those who lack the ability to use a metered-dose or breath-activated inhaler.

A "dry powder inhaler" is a device that is loaded with a unit dosage of the drug in powder form. Generally, the inhaler is activated by taking a breath. For example, a capsule or blister is punctured and the powder is dispersed so that it can be inhaled in, e.g., a "Spinhaler" or "Rotahaler." "Turbohalers" are fitted with canisters that deliver measured doses of the drug in powder form.

A "metered dose inhaler" or "MDI" is a device that delivers a measured dose of a drug in the form of a suspension of extremely small liquid or solid particles, which is dispensed from the inhaler by a propellant under pressure. Such inhalers are placed into the mouth and depressed (activated) to release the drug as the individual takes a breath.

As used herein, the term "emitted dose" or "ED" refers to an indication of the delivery of dry powder from an inhaler device after an actuation or dispersion event from a powder unit or reservoir. ED is defined as the ratio of the dose delivered by an inhaler device to the nominal dose (i.e., the mass of powder per unit dose placed into a suitable inhaler device prior to firing). The ED is an experimentally determined amount, and may be determined using an in vitro device set-up which mimics patient dosing. To determine an ED value, as used herein, dry powder is placed into a Pulmonary Delivery System (PDS) device (Nektar Therapeutics), described in U.S. Pat. No. 6,257,233, which is incorporated herein by reference in its entirety. The PDS device is actuated, dispersing the powder. The resulting aerosol cloud is then drawn from the device by vacuum (30 L/min) for 2.5 seconds after actuation, where it is captured on a tared glass fiber filter (Gelman, 47 mm diameter) attached to the device mouthpiece. The amount of powder that reaches the filter constitutes the delivered dose. For example, for a blister containing 5 mg of dry powder that is placed into an inhalation device, if dispersion of the powder results in the recovery of 4 mg of powder on a tared filter as described above, then the ED for the dry powder composition is 80% (=4 mg (delivered dose)/5 mg (nominal dose)).

A composition in "dry powder form" is a powder composition that typically contains less than about 20 wt %, less than about 10 wt %, or less than about 5 wt %, of water.

As used herein, "mass median diameter" or "MMD" refers to the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise. Typically, powder samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using an algorithm.

"Mass median aerodynamic diameter," or "MMAD," is a measure of the aerodynamic size of a dispersed particle. The aerodynamic diameter is used to describe an aerosolized powder in terms of its settling behavior, and is the diameter of a unit density sphere having the same settling velocity, in air, as the particle. The aerodynamic diameter encompasses particle shape, density, and physical size of a particle. As used herein, MMAD refers to the midpoint or median of the aerodynamic particle size distribution of an aerosolized powder determined by cascade impaction at standard conditions using a Pulmonary Delivery System (PDS) device (Nektar Therapeutics), described in U.S. Pat. No. 6,257,233, which is incorporated herein by reference in its entirety, unless otherwise indicated.

"Fine particle fraction" is the fraction of particles with an aerodynamic diameter that is less than 5 microns. Where specified, the fine particle fraction may also refer to the fraction of particles with an aerodynamic diameter that is less than 3.3 microns.

"Treating or ameliorating" a disease or medical condition means reducing or eliminating the symptoms of the disease or medical condition. In some embodiments, "treating or ameliorating" a disease or medical condition will be directed at addressing the cause of the disease or medical condition. Treating a disease may result in cure of the disease.

"Basal insulin" refers to a long-acting insulin that is sufficient to sustain steady low levels of insulin effective to satisfy basal requirements. Generally, a basal insulin is one exhibiting a prolonged time of action of greater than about 8 hours in a standard model of diabetes. Commercially available basal insulins include neutral protamine Hagedorn (NPH), Lente, and Ultralente'—and analogs such as insulin glargine.

A GLP-1 polymer conjugate which lacks bioactivity is one which, when evaluated in an assay suitable for assessing GLP-1 bioactivity, possesses a bioactivity of less than about 2% when compared to native GLP-1. Various assays may be used to assess bioactivity, including in-vitro and in-vivo assays that measure GLP-1 receptor binding activity or receptor activation, as described in greater detail herein. A receptor-signaling assay may also be used to assess GLP-1 activity (see, e.g., Zlokarnik et al, Science, 1998, 279:84-88).

A "monomer" or "mono-conjugate", in reference to a polymer conjugate of GLP-1, refers to a GLP-1 moiety having only one water-soluble polymer molecule covalently attached thereto, whereas a GLP-1 "dimer" or "di-conjugate" is a polymer conjugate of GLP-1 having two water-soluble polymer molecules covalently attached thereto, and so forth.

Turning now to one or more aspects of the present invention, conjugates are provided, the conjugates typically comprising a GLP-1 moiety releasably attached, either directly via a hydrolyzable linkage or via a linker comprised of a hydrolyzable linkage, to a water-soluble polymer. The conjugates of the invention, when administered in vivo, are usually effective not only in providing a significant reduction in blood glucose levels, but have been shown to possess extended release properties. That is to say, the blood glucose lowering ability of the present conjugates is typically effective over a duration of hours, and in some instances, days, in contrast to the rapid clearance and short activity of native GLP-1. Thus, the conjugates of the invention typically provide several notable advantages over native GLP-1. Finally, although it has been suggested that N-terminal modification of GLP-1 is ineffective to provide a GLP-1 derivative suitable for pharmacological use, see for example, International Patent Publication No. WO 04/078777, the present invention provides, in one aspect, N-terminally modified water-soluble polymer conjugates that are not only effective, but indeed possess several advantages over native GLP-1, to be described in greater detail below.

The GLP-1 Moiety

The conjugates of the invention comprise a GLP-1 moiety. As previously stated, the term "GLP-1 moiety" is meant to encompass the GLP-1 moiety prior to conjugation as well as following attachment to one or more water-soluble polymers. It will be understood, however, that when the GLP-1 moiety is covalently attached to a water-soluble polymer, the GLP-1 moiety is slightly altered due to the presence of one or more covalent bonds associated with linkage to the polymer (or linker that is attached to the polymer), due to reaction of one of more reactive groups of the GLP-1 moiety (e.g., an amino, carboxyl, etc.), with the water-soluble polymer. Often, this slightly altered form of the GLP-1 moiety attached to another molecule, such as a water-soluble polymer, is referred to as a "residue" of the GLP-1 moiety.

A GLP-1 moiety for use in the invention is any GLP-1 moiety having GLP-1 activity. Numerous GLP-1 analogs, derivatives, and variants have been previously described, and are encompassed by the term, "GLP-1 moiety". One preferred GLP-1 moiety for use in the invention is human GLP-1, a 37 amino acid peptide. Its naturally-occurring forms include GLP-1 (7-36)$NH_2$, GLP-1 (7-37)OH and GLP-1 (7-37)$NH_2$, where, according to conventional numbering, the N-terminal histidine is assigned as residue 7. Commercially-available forms also include GLP-1 (1-36).

The amino acid sequence of GLP-1 (7-36) corresponds to: (SEQ ID NO:1).

His7-Ala8-Glu9-Gly10-Thr11-Phe12-Thr13-Ser14-

Asp15-Val16-Ser17-Ser18-Tyr19-Leu20-Glu21-Gly22-

Gln23-Ala24-Ala25-Lys26-Glu27-Phe28-Ile29-Ala30-

Trp31-Leu32-Val33-Lys34-Gly35-Arg36

The amino acid sequence of GLP-1 (7-37)OH corresponds to: (SEQ ID NO:2).

His7-Ala8-Glu9-Gly10-Thr11-Phe12-Thr13-Ser14-

Asp15-Val16-Ser17-Ser18-Tyr19-Leu20-Glu21-Gly22-

Gln23-Ala24-Ala25-Lys26-Glu27-Phe28-Ile29-Ala30-

Trp31-Leu32-Val33-Lys34-Gly35-Arg36-Gly37

Additional GLP-1 moieties for use in the invention include GLP-1 peptide analogs such as those described in WO 91/11457, N-terminal truncated fragments of GLP-1 as described in EP 0 699 686, and cysteine-inserted GLP-1 sequences as described in WO 2004/093823, among others. Cysteine-inserted GLP-1 variants for use in the invention include those having a cysteine inserted at positions selected from amino acid 11, 12, 16, 22, 23, 24, 25, 26, 27, 30, 34, 35, 36, and 37 of GLP-1. Such variants are typically designated as follows. For instance, a GLP-1 variant having a cysteine inserted at positions 22 and 35 is typically described as [Cys$^{22}$Cys$^{35}$]GLP-1(7-37). Variants for use in preparing a conjugate of the invention often have no more than 1 or 2 cysteine amino acids per GLP-1 moiety. Exemplary locations for insertion of a cysteine include, but are not limited to, amino acids 22, 26, 34, 35, 36, and 37 of GLP-1. Such GLP-1 moieties are particularly useful for conjugation to a thiol-selective polymer reagent, such as a water-soluble polymer having one or more reactive maleimide functional groups.

Other GLP-1 moieties suitable for use in the invention include GLP-1 moieties as described in U.S. Published Application No. 2004/0235710, corresponding to Ser. No. 10/486,333.

Also for use in the present invention are GLP-1 analogs referred to as exendins. Exendins are peptides that were first isolated from the salivary secretions of the Gila-monster and the Mexican Beaded Lizard. The exendins have a degree of similarity to several members of the GLP family, with the highest homology, 53%, to GLP-1 (7-36)NH$_2$(Goke, et al., J. Biol. Chem., 268:19650-55, 1993).

Particular exendins for use in the present invention include exendin-3 and exendin-4 (synthetic extendin-4 is also known as Exenatide).

Exendin-3 (1-39) has the following amino acid sequence: (SEQ ID NO:3).

His Ser Asp Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro Ser.

The amino acid sequence of exendin-4 (1-39) corresponds to: (SEQ ID NO:4).

His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro Ser wherein the C-terminus serine is amidated.

The GLP-1 moiety may be obtained from either non-recombinant methods or from recombinant methods, and the invention is not limited in this regard. Moreover, several GLP-1 moieties are commercially available, e.g., hGLP-1, rExendin-4, and rHuGLP-1 are available from ProSpecTany Techno Gene LTD (Rehovot, Israel); and (Ser8)GLP-1 (7-36) amide, hGLP-1 amide, hGLP-1 (7-36)Lys(biotin)amide, (American Peptide Co., Sunnyvale, Calif.), among others. Methods for preparing GLP-1 moieties are well-known, and are described, e.g., in U.S. Pat. Nos. 5,118,666; 5,120,712; and 5,523,549.

GLP-1 moieties can be prepared using standard methods of solution or solid phase peptide synthesis such as those described in Dugas H., Penny, C., *Bioorganic Chemistry*, Springer Verlag, New York, p. 54-92 (1981); Merrifield, J. M., *Chem Soc.*, 85, 2149 (1962), and Stewart and Young, *Solid Phase Peptide Synthesis*, Freeman, San Francicso, p. 24-66 (1969). Peptide synthesizers are available from, e.g., Applied Biosystems, Foster City, Calif. Solid phase synthesizers are typically used according to manufacturers' instructions for blocking interfering groups, protecting certain amino acids, coupling, decoupling, and capping unreacted amino acids. BOC-amino acids and other reagents are commercially available from Applied Biosystems. As a non-limiting example, sequential BOC chemistry using double coupling protocols are applied to the starting p-methyl benzhydryl amine resins for the production of C-terminal carboxamides. For the production of C-terminal acids, the corresponding PAM resin is used. Asn, Gln, and Arg are coupled using preformed hydroxybenzotriazole esters. Suitable side chain protecting groups include: Arg (tosyl), Asp (cyclohexyl), Glu (cyclohexyl), Ser (benzyl), Thr (benzyl), and Tyr (4-bromocarbobenzoxy). BOC deprotection may be carried out with trifluoroacetic acid in methylene chloride. Following synthesis, the resulting peptide may be deprotected and cleaved from the resin using, e.g., anhydrous HF containing 10% meta-cresol.

Exemplary recombinant methods used to prepare a GLP-1 moiety (whether a human GLP-1 or a different protein having GLP-1 activity) include the following, among others as will be apparent to one skilled in the art. Typically, a GLP-1 moiety as described herein is prepared by constructing the nucleic acid encoding the desired polypeptide or fragment, cloning the nucleic acid into an expression vector, transforming a host cell (e.g., plant, bacteria such as *Escherichia coli*, yeast such as *Saccharomyces cerevisiae*, or mammalian cell such as Chinese hamster ovary cell or baby hamster kidney cell), and expressing the nucleic acid to produce the desired polypeptide or fragment. The expression can occur via exogenous expression (when the host cell naturally contains the desired genetic coding) or via endogenous expression. Methods for producing and expressing recombinant polypeptides in vitro and in prokaryotic and eukaryotic host cells are known to those of ordinary skill in the art. See, for example, U.S. Pat. No. 4,868,122.

To facilitate identification and purification of the recombinant polypeptide, nucleic acid sequences that encode an epitope tag or other affinity binding sequence can be inserted or added in-frame with the coding sequence, thereby producing a fusion protein comprised of the desired polypeptide and a polypeptide suited for binding. Fusion proteins can be identified and purified by first running a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be identified and purified by lysing the host cells, separating the polypeptide, e.g., by size exclusion chromatography, and collecting the polypeptide. These and other methods for identifying and purifying recombinant polypeptides are known to those of ordinary skill in the art. In one or more embodiments of the present invention, the GLP-1 moiety is not in the form of a fusion protein. See, for example, Dillon et al., Cloning and Functional Expression of the Human Glucagon-Like Peptide-1 Receptor, Endocrinology, 133:1907-1910 (1993).

For any given moiety, it is possible to determine whether that moiety possesses GLP-1 activity. Various assays may be used to assess bioactivity, including in-vitro and in-vivo assays that measure GLP-1 receptor binding activity or receptor activation. See, for example, EP 619 322 and U.S. Pat. No. 5,120,712 for descriptions of assessing GLP-1 activity. A receptor-signaling assay may also be used to assess GLP-1 activity, such as described in Zlokarnik et al, Science, 279, 84-88, 1998.

Other methods known to those of ordinary skill in the art can also be used to determine whether a given moiety has GLP-1 activity. Such methods are useful for determining the GLP-1 activity of both the moiety itself (and therefore can be used as a "GLP-1 moiety"), as well as that of the corresponding polymer-moiety conjugate. For example, one can determine whether a given moiety is an agonist of the human GLP-1 receptor by assessing whether that moiety stimulates the formation of cAMP in a suitable medium containing the human GLP-1 receptor. The potency of such moiety is determined by calculating the EC50 value from a dose response curve. As an example, BHK cells (baby hamster kidney cells) expressing the cloned human GLP-1 receptor can be grown in DMEM media containing penicillin, streptomycin, calf serum, and Geneticin. The cells are then washed in phosphate buffered saline and harvested. Plasma membranes are then prepared from the cells by homogenization, and the homogenate is then centrifuged to produce a pellet. The resulting pellet is suspended by homogenization in a suitable buffer, centrifuged, and then washed. The cAMP receptor assay is then carried out by measuring cyclic AMP (cAMP) in response to the test insulinotropic moiety. cAMP can be quantified using the AlphaScreen™ cAMP Kit (Perkin Elmer). Incubations are typically carried out in microtiter plates in buffer, with addition of, e.g., ATP, GTP, IBMX (3-isobutyl-1-methylxanthine, Tween-20, BSA, acceptor beads, and donor beads incubated with biotinylated-cAMP. Counting may be carried out, e.g., using the Fusion™ instrument (Perkin Elmer). Concentration-response curves are then plotted for the individual insulinotropic moieties under evaluation, and their $EC_{50}$ values determined.

Nonlimiting examples of GLP-1 moieties include any of SEQ ID NO: 1, SEQ ID NO: 2 and SEQ ID NO: 3; and SEQ ID NO:4; truncated versions thereof; hybrid variants, and peptide mimetics having GLP-1 activity. Biologically active fragments, deletion variants, substitution variants or addition variants of any of the foregoing that maintain at least some degree of GLP-1 activity can also serve as a GLP-1 moiety in the conjugates of the invention.

GLP-1 Modifications

A GLP-1 moiety as described herein may also contain one or more additional modifications, e.g., the introduction of one or more glycosides, or methyl groups.

Methylation

A GLP-1 moiety may also possess one or more methyl or other lower alkyl groups at one or more positions of the GLP-1 sequence. Examples of such groups include methyl, ethyl, propyl, isopropyl, butyl, isobutyl, pentyl, etc. Sites of modification include residues 7, 8, 9, and/or 10, with the 7 and/or 9 positions being preferred. Introduction of one or more methyl groups is expected to modify the dipeptidyl peptidase IV (DPP IV) recognition site, such that the modified GLP-1 is protected against degradation by DPP IV. While not wishing to be bound by theory, it is believed that N-methylation at positions other than 7, 8, 9, and/or 10 may disrupt the helicity of GLP-1 and thereby reduce its activity.

Introduction of N-terminal modifications to GLP-1 may be carried out as described by Gallwitz, B., et al., *Regulatory Peptides*, 86 (1-3), 103-111 (2000) or WO 2004/007427, which are incorporated herein by reference in their entireties. Illustrative GLP-1 analogues with alternations at the N-terminus include N-methylated GLP-1 (N-me-GLP-1), alpha-methylated GLP-1 (alpha-me-GLP-1), desamidated GLP-1 (desamino-GLP-1), and imidazole-lactic acid substituted GLP-1 (imi-GLP-1), among others, and are suitable for use in the present invention.

Methods for synthesizing various other analogues of GLP-1, including methyl-derivatives as described above, as well examples of such additional GLP-1 analogues are described in International Patent Publications WO 00/34332, WO 2004/074315, and WO 2005/058955.

Glycosylation

The GLP-1 moieties described herein may also contain one or more glycosides. Although any glycoside can be used, the GLP-1 moiety is preferably modified by introduction of either a monosaccharide, a disaccharide, or a trisaccharide. Although any site on the GLP-1 moiety may be modified by introduction of a saccharide, preferably, the saccharide is introduced at any one or more of positions 7, 8, or 9 to protect the peptide against DPP IV proteolysis. Further, additional glycosides may be introduced, e.g., at any one or more of positions 11, 13, 14, 17, 18, 21, 22, 23, 24, 26, and 34 to increase the helicity through the central portion of the peptide, as well as provide additional resistance to proteolysis. Glycosylation may occur on a naturally occurring amino acid. Alternatively, a saccharide may be covalently attached to one or more sites of the GLP-1 moiety, wherein the one or more sites each comprise one of Asp, Asn, Ser, and Thr that is substituted at one or more sites selected from the N-terminus (His7), Ala8, Glu9, Thr11, Thr13, Ser14, Ser17, Ser18, Glu21, Gly22, Gln23, Lys26, and Lys34.

Glycosylated GLP-1 moieties may be prepared using conventional Fmoc chemistry and solid phase peptide synthesis techniques, e.g., on resin, where the desired protected glycoamino acids are prepared prior to peptide synthesis and then introduced into the peptide chain at the desired position during peptide synthesis. Thus, the GLP-1 polymer conjugates may be conjugated in vitro. The glycosylation may occur before deprotection. Preparation of aminoacid glycosides is described in U.S. Pat. No. 5,767,254, WO 2005/097158, and Doores, K., et al., *Chem. Commun.*, 1401-1403, 2006, which are incorporated herein by reference in their entireties. For example, alpha and beta selective glycosylations of serine and threonine residues are carried out using the Koenigs-Knorr reaction and Lemieux's in situ anomerization methodology with Schiff base intermediates. Deprotection of the Schiff base glycoside is then carried out using mildly acidic conditions or hydrogenolysis. A composition, comprising a glycosylated and pegylated GLP-1 conjugate made by stepwise solid phase peptide synthesis involving contacting a growing peptide chain with protected amino acids in a stepwise manner, wherein at least one of the protected amino acids is glycosylated, followed by pegylation, may have a purity of at least about 95%, such as at least about 97%, or at least about 98%, of a single species of the glycosylated and pegylated GLP-1 conjugate.

Monosaccharides that may by used for introduction at one or more amino acid residues of GLP-1 include glucose (dextrose), fructose, galactose, and ribose. Additional monosaccharides suitable for use include glyceraldehydes, dihydroxyacetone, erythrose, threose, erythrulose, arabinose, lyxose, xylose, ribulose, xylulose, allose, altrose, mannose, as well as others. Glycosides, such as mono-, di-, and trisaccharides for use in modifying a GLP-1 moiety, may be naturally occurring or may be synthetic.

Disaccharides that may by used for introduction at one or more amino acid residues of GLP-1 include sucrose, lactose, maltose, trehalose, melibiose, and cellobiose, among others. Trisaccharides include acarbose, raffinose, and melezitose.

The Water-Soluble Polymer

A conjugate of the invention comprises a GLP-1 moiety attached, preferably but not necessarily releasably, to a water-soluble polymer. The water-soluble polymer is typically hydrophilic, nonpeptidic, nontoxic, non-naturally occurring and biocompatible. A substance is considered biocompatible if the beneficial effects associated with use of the substance alone or with another substance (e.g., an active agent such a GLP-1 moiety) in connection with living tissues (e.g., administration to a patient) outweighs any deleterious effects as evaluated by a clinician, e.g., a physician. A substance is considered nonimmunogenic if the intended use of the substance in vivo does not produce an undesired immune response (e.g., the formation of antibodies) or, if an immune response is produced, that such a response is not deemed clinically significant or important as evaluated by a clinician. Typically, the water-soluble polymer is hydrophilic, biocompatible and nonimmunogenic.

Further the water-soluble polymer is typically characterized as having from 2 to about 300 termini, preferably from 2 to 100 termini, and more preferably from about 2 to 50 termini. Examples of such polymers include, but are not limited to, poly(alkylene glycols) such as polyethylene glycol (PEG), polypropylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), and combinations of any of the foregoing, including copolymers and terpolymers thereof.

The water-soluble polymer is not limited to a particular structure and may possess a linear architecture (e.g., alkoxy PEG or bifunctional PEG), or a non-linear architecture, such as branched, forked, multi-armed (e.g., PEGs attached to a polyol core), or dendritic. Moreover, the polymer subunits can be organized in any number of different patterns and can be selected, e.g., from homopolymer, alternating copolymer, random copolymer, block copolymer, alternating tripolymer, random tripolymer, and block tripolymer.

One particularly preferred type of water-soluble polymer for use in the invention is a polyalkylene oxide, and in particular, polyethylene glycol (or PEGs). Generally, a PEG used to prepare a GLP-1 polymer conjugate of the invention is "activated" or reactive. That is to say, the activated PEG (and other activated water-soluble polymers collectively referred to herein as "polymeric reagents") used to form a GLP-1 conjugate comprises an activated functional group suitable for coupling to a desired site or sites on the GLP-1 moiety. Thus, a polymeric reagent for use in preparing a GLP-1 conjugate includes a functional group for reaction with the GLP-moiety.

Representative polymeric reagents and methods for conjugating such polymers to an active moiety are known in the art, and are, e.g., described in Harris, J. M. and Zalipsky, S., eds, *Poly(ethylene glycol), Chemistry and Biological Applications*, ACS, Washington, 1997; Veronese, F., and J. M Harris, eds., *Peptide and Protein PEGylation*, Advanced Drug Delivery Reviews, 54(4); 453-609 (2002); Zalipsky, S., et al., "*Use of Functionalized Poly(Ethylene Glycols) for Modification of Polypeptides*" in *Polyethylene Glycol Chemistry: Biotechnical and Biomedical Applications*, J. M. Harris, ed., Plenus Press, New York (1992); Zalipsky (1995) *Advanced Drug Reviews* 16:157-182, and in Roberts, et al., *Adv. Drug Delivery Reviews,* 54, 459-476 (2002).

Additional PEG reagents suitable for use in forming a conjugate of the invention, and methods of conjugation are described in the Nektar Advanced PEGylation Catalogs, 2005-2006; 2004; 2003; and in Shearwater Corporation, Catalog 2001; Shearwater Polymers, Inc., Catalogs, 2000 and 1997-1998, and in Pasut. G., et al., *Expert Opin. Ther. Patents* (2004), 14(5). PEG reagents suitable for use in the present invention also include those available from NOF Corporation, as described generally on the NOF website (2006) under Products, High Purity PEGs and Activated PEGs. Products listed therein and their chemical structures are expressly incorporated herein by reference. Additional PEGs for use in forming a GLP-1 conjugate of the invention include those available from Polypure (Norway) and from QuantaBioDesign LTD (Ohio), where the contents of their online catalogs (2006) with respect to available PEG reagents are expressly incorporated herein by reference.

Typically, the weight-average molecular weight of the water-soluble polymer in the conjugate is from about 100 Daltons to about 150,000 Daltons. Exemplary ranges, however, include weight-average molecular weights in the range of from about 250 Daltons to about 80,000 Daltons, from 500 Daltons to about 80,000 Daltons, from about 500 Daltons to about 65,000 Daltons, from about 500 Daltons to about 40,000 Daltons, from about 750 Daltons to about 40,000 Daltons, from about 1000 Daltons to about 30,000 Daltons.

For any given water-soluble polymer, a molecular weight in one or more of these ranges is typical. Generally, a GLP-1 conjugate in accordance with the invention, when intended for subcutaneous or intravenous administration, will comprise a PEG or other suitable water-soluble polymer having a weight average molecular weight of about 20,000 Daltons or greater, while a GLP-1 conjugate intended for pulmonary administration will generally, although not necessarily, comprise a PEG polymer having a weight average molecular weight of about 20,000 Daltons or less. For example, Examples 25 and 26 provide intratracheal instillation data in mice for an illustrative branched PEG having an overall molecular weight of about 8 kD.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons.

Branched versions of the water-soluble polymer (e.g., a branched 40,000 Dalton water-soluble polymer comprised of two 20,000 Dalton polymers or the like) having a total molecular weight of any of the foregoing can also be used. In one or more particular embodiments, depending upon the other features of the subject GLP-1 polymer conjugate, the conjugate is one that does not have one or more attached PEG moieties having a weight-average molecular weight of less than about 6,000 Daltons.

In instances in which the water-soluble polymer is a PEG, the PEG will typically comprise a number of $(OCH_2CH_2)$ monomers [or $(CH_2CH_2O)$ monomers, depending on how the PEG is defined]. As used herein, the number of repeat units is typically identified by the subscript "n" in, for example, "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. Preferred ranges of n include from about 10 to about 700, and from about 10 to about 1800. For any given polymer in which the molecular weight is known, it is possible to determine the number of repeating units (i.e., "n") by dividing the total weight-average molecular weight of the polymer by the molecular weight of the repeating monomer.

With regard to the molecular weight of the water-soluble polymer, in or more particular embodiments of the invention, depending upon the other features of the particular GLP-1 conjugate, the conjugate comprises a GLP-1 moiety covalently attached to a water-soluble polymer having a molecular weight greater than about 2,000 Daltons.

A polymer for use in the invention may be end-capped, that is, a polymer having at least one terminus capped with a relatively inert group, such as a lower alkoxy group (i.e., a $C_{1-6}$ alkoxy group) or a hydroxyl group. One frequently employed end-capped polymer is methoxy-PEG (commonly referred to as mPEG), wherein one terminus of the polymer is a methoxy (—$OCH_3$) group. The -PEG-symbol used in the foregoing generally represents the following structural unit: —$CH_2CH_2O$—$(CH_2CH_2O)_n$—$CH_2CH_2$—, where (n) generally ranges from about zero to about 4,000.

Multi-armed or branched PEG molecules, such as those described in U.S. Pat. No. 5,932,462, are also suitable for use in the present invention. For example, the PEG may be described generally according to the structure:

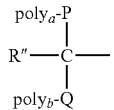

where $poly_a$ and $poly_b$ are PEG backbones (either the same or different), such as methoxy poly(ethylene glycol); R" is a non-reactive moiety, such as H, methyl or a PEG backbone; and P and Q are non-reactive linkages. In one embodiment, the branched PEG molecule is one that includes a lysine residue, such as the following reactive PEG suitable for use in forming a GLP-1 conjugate. See, e.g., the Shearwater Corporation Catalog, 2001, page 6. Although the branched PEG below is shown with a reactive succinimidyl group, this represents only one of a myriad of reactive functional groups suitable for reacting with a GLP-1 moiety.

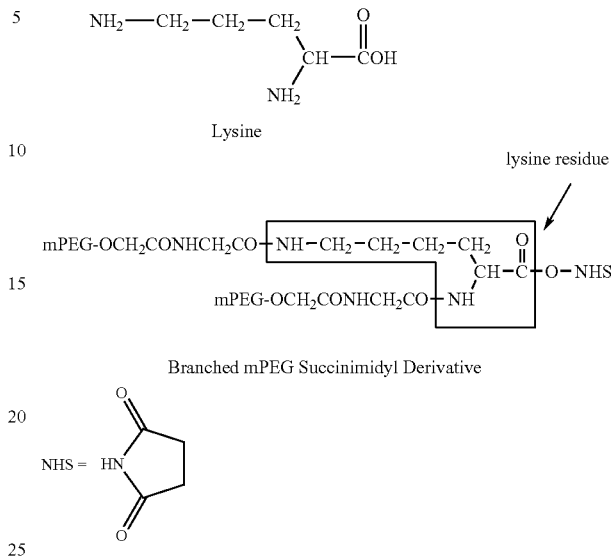

In some instances, the polymeric reagent (as well as the corresponding conjugate prepared from the polymeric reagent) may lack a lysine residue in which the polymeric portions are connected to amine groups of the lysine via a "—$OCH_2CONHCH_2CO$—" group. In still other instances, the polymeric reagent (as well as the corresponding conjugate prepared from the polymeric reagent) may lack a branched water-soluble polymer that includes a lysine residue (wherein the lysine residue is used to effect branching).

Additional branched PEGs for use in forming a GLP-1 conjugate of the present invention include those described in co-owned U.S. Patent Application Publication No. 2005/0009988. Representative branched polymers described therein include those having the following generalized structure:

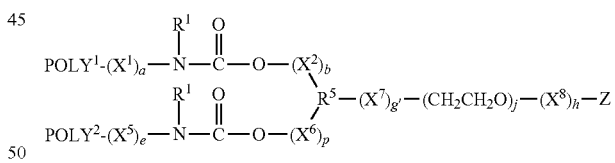

where POLY$^1$ is a water-soluble polymer; POLY$^2$ is a water-soluble polymer; (a) is 0, 1, 2 or 3; (b) is 0, 1, 2 or 3; (e) is 0, 1, 2 or 3; (f') is 0, 1, 2 or 3; (g') is 0, 1, 2 or 3; (h) is 0, 1, 2 or 3; (j) is 0 to 20; each R$^1$ is independently H or an organic radical selected from alkyl, substituted alkyl, alkenyl, substituted alkenyl, alkynyl, substituted alkynyl, aryl and substituted aryl; X$^1$, when present, is a spacer moiety; X$^2$, when present, is a spacer moiety; X$^5$, when present, is a spacer moiety; X$^6$, when present, is a spacer moiety; X$^7$, when present, is a spacer moiety; X$^8$, when present, is a spacer moiety; R$^5$ is a branching moiety; and Z is a reactive group for coupling to a GLP-1 moiety, optionally via an intervening spacer. POLY$^1$ and POLY$^2$ in the preceding branched polymer structure may be different or identical, i.e., are of the same polymer type (structure) and molecular weight.

A preferred branched polymer falling into the above classification suitable for use in the present invention is:

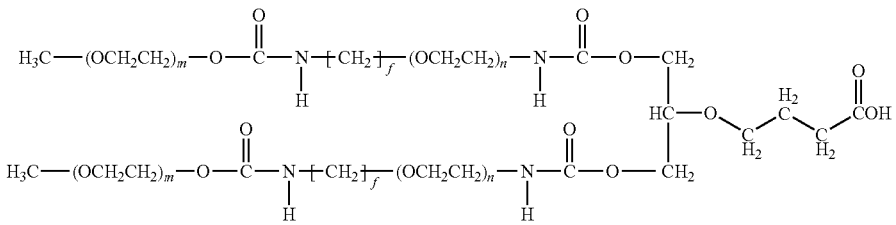

where (m) is 2 to 4000, and (l) is 0 to 6 and (n) is 0 to 20.

Branched polymers suitable for preparing a conjugate of the invention also include those represented more generally by the formula R(POLY)$_y$, where R is a central or core molecule from which extends 2 or more POLY arms such as PEG. The variable y represents the number of POLY arms, where each of the polymer arms can independently be end-capped or alternatively, possess a reactive functional group at its terminus. A more explicit structure in accordance with this embodiment of the invention possesses the structure, R(POLY-Z)$_y$, where each Z is independently an end-capping group or a reactive group, e.g., suitable for reaction with a GLP-1 moiety. In yet a further embodiment when Z is a reactive group, upon reaction with a GLP-1 moiety, the resulting linkage can be hydrolytically stable, or alternatively, may be degradable, i.e., hydrolyzable. Typically, at least one polymer arm possesses a terminal functional group suitable for reaction with, e.g., a GLP-1 moiety. Branched PEGs such as those represented generally by the formula, R(PEG)$_y$ above possess 2 polymer arms to about 300 polymer arms (i.e., n ranges from 2 to about 300). Preferably, such branched PEGs typically possess from 2 to about 25 polymer arms, such as from 2 to about 20 polymer arms, from 2 to about 15 polymer arms, or from 3 to about 15 polymer arms. Multi-armed polymers include those having 3, 4, 5, 6, 7 or 8 arms.

Core molecules in branched PEGs as described above include polyols, which are then further functionalized. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Typical polyols include glycerol, pentaerythritol, sorbitol, and trimethylolpropane.

As will be described in more detail in the linker section below, although any of a number of linkages can be used to covalently attach a polymer to a GLP-1 moiety, in certain instances, the linkage is degradable, designated herein as L$_D$, that is to say, contains at least one bond or moiety that hydrolyzes under physiological conditions, e.g., an ester, hydrolyzable carbamate, carbonate, or other such group.

Illustrative multi-armed PEGs having 3 arms, 4-arms, and 8 arms correspond to those in Nektar's Advanced PEGylation Catalog 2005-2006, page 26. Multi-armed activated polymers for use in the method of the invention include those corresponding to the following structure, where E represents a reactive group suitable for reaction with a reactive group on the GLP-1 moiety. In one or more embodiments, E is an —OH (for reaction with a GLP-1 carboxy group or equivalent), a carboxylic acid or equivalent (such as an active ester), a carbonic acid (for reaction with GLP-1 —OH groups), or an amino group.

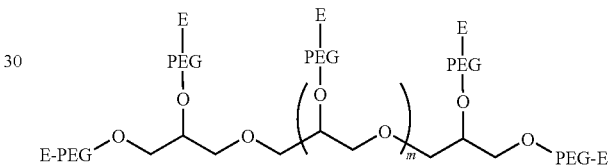

In the structure above, PEG is —(CH$_2$CH$_2$O)$_n$CH$_2$CH$_2$—, and m is selected from 3, 4, 5, 6, 7, and 8. In certain embodiments, typical linkages are ester, carboxyl and hydrolyzable carbamate, such that the polymer-portion of the conjugate is hydrolyzed in vivo to release the GLP-1 moiety from the intact polymer conjugate. In such instances, the linker L is designated as L$_D$.

Alternatively, the polymer may possess an overall forked structure as described in U.S. Pat. No. 6,362,254. This type of polymer segment is useful for reaction with two GLP-1 moieties, where the two GLP-1 moieties are positioned a precise or predetermined distance apart.

In any of the representative structures provided herein, one or more degradable linkages may additionally be contained in the polymer segment, POLY, to allow generation in vivo of a conjugate having a smaller PEG chain than in the initially administered conjugate. Appropriate physiologically cleavable (i.e., releasable) linkages include but are not limited to ester, carbonate ester, carbamate, sulfate, phosphate, acyloxyalkyl ether, acetal, and ketal. Such linkages when contained in a given polymer segment will often be stable upon storage and upon initial administration.

The PEG polymer used to prepare a GLP-1 polymer conjugate may comprise a pendant PEG molecule having reactive groups, such as carboxyl or amino, covalently attached along the length of the PEG rather than at the end of the PEG chain(s). The pendant reactive groups can be attached to the PEG directly or through a spacer moiety, such as an alkylene group.

Additional representative PEGs having either linear or branched structures for use in forming a conjugate of the invention may be purchased from Nektar Therapeutics (formerly Shearwater Corporation, Huntsville, Ala.). Illustrative PEG reagents are described in Nektar's 2005-2006 catalogue entitled, "Polyethylene Glycol and Derivatives for Advanced PEGylation," the contents of which is expressly incorporated herein by reference.

Releasable Linkage

Preferably, a GLP-1 polymer conjugate according to one aspect of the invention is one comprising a GLP-1 moiety releasably attached, preferably at its N-terminus, to a water-soluble polymer. Hydrolytically degradable linkages, useful not only as a degradable linkage within a polymer backbone, but also, in the case of certain preferred embodiments of the invention, for covalently attaching a water-soluble polymer to a GLP-1 moiety, include: carbonate; imine resulting, for example, from reaction of an amine and an aldehyde (see, e.g., Ouchi et al. (1997) *Polymer Preprints* 38(1):582-3); phosphate ester, formed, for example, by reacting an alcohol with a phosphate group; hydrazone, e.g., formed by reaction of a hydrazide and an aldehyde; acetal, e.g., formed by reaction of an aldehyde and an alcohol; orthoester, formed, for example, by reaction between a formate and an alcohol; and esters, and certain urethane (carbamate) linkages.

Illustrative PEG reagents for use in preparing a releasable GLP-1 conjugate in accordance with the invention are described in U.S. Pat. Nos. 6,348,558, 5,612,460, 5,840,900, 5,880,131, and 6,376,470.

Additional PEG reagents for use in the invention include hydrolyzable or releasable PEGs and linkers such as those described in U.S. patent application Ser. No. 11/454,971, filed Jun. 16, 2006. In the resulting conjugate, the GLP-1 moiety and the polymer are each covalently attached to different positions of the scaffold aromatic, e.g., Fmoc or FMS, structure, and are releasable under physiological conditions. Generalized structures corresponding to the polymers described therein are provided below.

For example, one such polymeric reagent comprises the following structure:

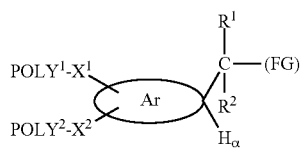

where $POLY^1$ is a first water-soluble polymer; $POLY^2$ is a second water-soluble polymer; $X^1$ is a first spacer moiety; $X^2$ is a second spacer moiety;

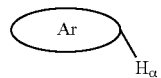

is an aromatic-containing moiety bearing an ionizable hydrogen atom, $H_\alpha$; $R^1$ is H or an organic radical; $R^2$ is H or an organic radical; and (FG) is a functional group capable of reacting with an amino group of an active agent to form a degradable linkage, such as a carbamate linkage (such as N-succinimidyloxy, 1-benzotriazolyloxy, oxycarbonylimidazole, —O—C(O)—Cl, O—C(O)—Br, unsubstituted aromatic carbonate radicals and substituted aromatic carbonate radicals). The polymeric reagent can include one, two, three, four or more electron altering groups attached to the aromatic-containing moiety.

Preferred aromatic-containing moieties are bicyclic and tricyclic aromatic hydrocarbons. Fused bicyclic and tricyclic aromatics include pentalene, indene, naphthalene, azulene, heptalene, biphenylene, as-indacene, s-indacene, acenaphthylene, fluorene, phenalene, phenanthrene, anthracene, and fluoranthene.

A preferred polymer reagent possesses the following structure,

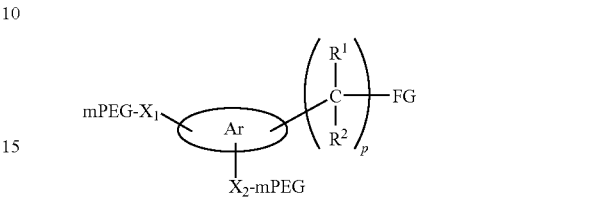

where mPEG corresponds to $CH_3O$—$(CH_2CH_2O)_n$ $CH_2CH_2$—, $X_1$ and $X$, are each independently a spacer moiety having an atom length of from about 1 to about 18 atoms, n ranges from 10 to 1800, p is an integer ranging from 1 to 8, $R_1$ is H or lower alkyl, $R_2$ is H or lower alkyl, and Ar is an aromatic hydrodrocarbon, preferably a bicyclic or tricyclic aromatic hydrocarbon. FG is as defined above. Preferably, FG corresponds to an activated carbonate ester suitable for reaction with an amino group on GLP-1. Preferred spacer moieties, $X_1$ and $X_2$, include —NH—C(O)—$CH_2$—O—, —NH—C(O)—$(CH_2)_q$—O—, —NH—C(O)—$(CH_2)_q$—C(O)—NH—, —NH—C(O)—$(CH_2)_q$—, and —C(O)—NH—, where q is selected from 2, 3, 4, and 5. Preferably, although not necessarily, the nitrogen in the preceding spacers is proximal to the PEG rather than to the aromatic moiety.

Another such branched (2-armed) polymeric reagent comprised of two electron altering groups comprises the following structure:

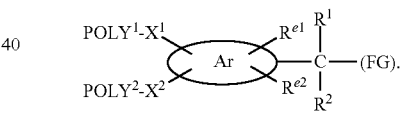

wherein each of $POLY^1$, $POLY^2$, $X^1$, $X^2$, $R^1$, $R^2$,

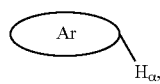

and (FG) is as defined immediately above, and $R^{e1}$ is a first electron altering group; and $R^{e2}$ is a second electron altering group. An electron altering group is a group that is either electron donating (and therefore referred to as an "electron donating group"), or electron withdrawing (and therefore referred to as an "electron withdrawing group"). When attached to the aromatic-containing moiety bearing an ionizable hydrogen atom, an electron donating group is a group having the ability to position electrons away from itself and closer to or within the aromatic-containing moiety. When attached to the aromatic-containing moiety bearing an ionizable hydrogen atom, an electron withdrawing group is a group having the ability to position electrons toward itself and away from the aromatic-containing moiety. Hydrogen is used as the standard for comparison in the determination of whether a given group positions electrons away or toward itself. Preferred electron altering groups include, but are not limited to, —CF$_3$, —CH$_2$CF$_3$, —CH$_2$C$_6$F$_5$, —CN, —NO$_2$, —S(O)R, —S(O)Aryl, —S(O$_2$)R, —S(O$_2$)Aryl, —S(O$_2$)OR, —S(O$_2$)OAryl, —S(O$_2$)NHR, —S(O$_2$)NHAryl, —C(O)R, —C(O)Aryl, —C(O)OR, —C(O)NHR, and the like, wherein R is H or an organic radical.

An additional branched polymeric reagent suitable for use in the present invention comprises the following structure:

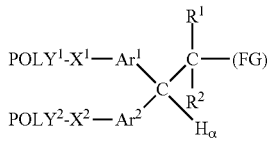

where POLY$^1$ is a first water-soluble polymer; POLY$^2$ is a second water-soluble polymer; X$^1$ is a first spacer moiety; X$^2$ is a second spacer moiety; Ar$^1$ is a first aromatic moiety; Ar$^2$ is a second aromatic moiety; H$_\alpha$ is an ionizable hydrogen atom; R$^1$ is H or an organic radical; R$^2$ is H or an organic radical; and (FG) is a functional group capable of reacting with an amino group of GLP-1 to form a degradable linkage, such as carbamate linkage.

Another exemplary polymeric reagent comprises the following structure:

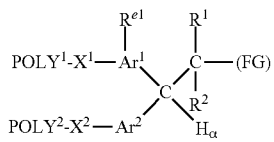

wherein each of POLY$^1$, POLY$^2$, X$^1$, X$^2$, Ar$^1$, Ar$^2$, H$_\alpha$, R$^1$, R$^2$, and (FG) is as previously defined, and R$^{e1}$ is a first electron altering group. While stereochemistry is not specifically shown in any structure provided herein, the provided structures contemplate both enantiomers, as well as compositions comprising mixtures of each enantiomer in equal amounts (i.e., a racemic mixture) and unequal amounts.

Yet an additional polymeric reagent for use in preparing a GLP-1 conjugate possesses the following structure:

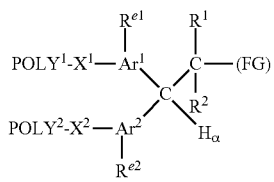

wherein each of POLY$^1$, POLY$^2$, X$^1$, X$^2$, Ar$^1$, Ar$^2$, H$_\alpha$, R$^1$, R$^2$, and (FG) is as previously defined, and R$^{e1}$ is a first electron altering group; and R$^{e2}$ is a second electron altering group.

A preferred polymeric reagent comprises the following structure:

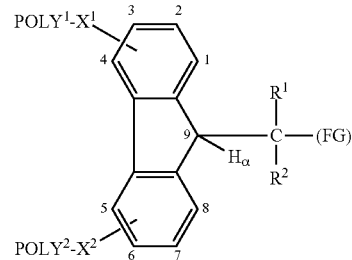

wherein each of POLY$^1$, POLY$^2$, X$^1$, X$^2$, R$^1$, R$^2$, H$_\alpha$ and (FG) is as previously defined, and, as can be seen from the structure above, the aromatic moiety is a fluorene. The POLY arms substituted on the fluorene can be in any position in each of their respective phenyl rings, i.e., POLY$^1$-X$^1$— can be positioned at any one of carbons 1, 2, 3, and 4, and POLY$^2$-X$^2$— can be in any one of positions 5, 6, 7, and 8.

Yet another preferred fluorene-based polymeric reagent comprises the following structure:

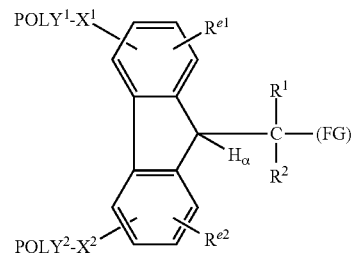

wherein each of POLY$^1$, POLY$^2$, X$^1$, X$^2$, R$^1$, R$^2$, H$_\alpha$ and (FG) is as previously defined, and R$^{e1}$ is a first electron altering group; and R$^{e2}$ is a second electron altering group as described above.

Yet another exemplary polymeric reagent for conjugating to a GLP-1 moiety comprises the following fluorene-based structure:

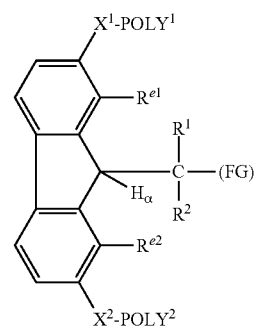

wherein each of POLY$^1$, POLY$^2$, X$^1$, X$^2$, R$^1$, R$^2$, H$_\alpha$ and (FG) is as previously defined, and R$^{e1}$ is a first electron altering group; and R$^{e2}$ is a second electron altering group.

Particular fluorene-based polymer reagents for forming a releasable GLP-1 polymer conjugate in accordance with the invention include the following:

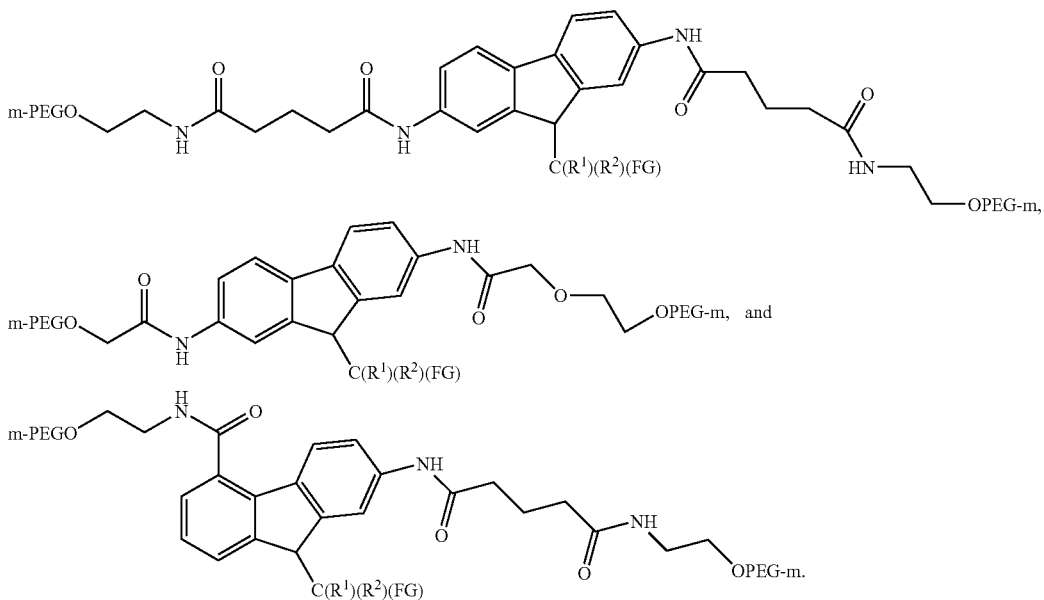

Still another exemplary polymeric reagent comprises the following structure:

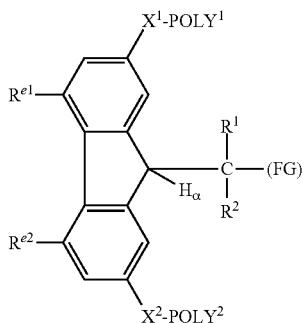

wherein each of POLY$^1$, POLY$^2$, X$^1$, X$^2$, R$^1$, R$^2$, H$_\alpha$ and (FG) is as previously defined, and R$^{e1}$ is a first electron altering group; and R$^{e2}$ is a second electron altering group. The syntheses and chemical structures of preferred branched releasable polymer reagents containing a fluorene scaffold, as well as their covalent attachment to GLP-1 are provided in Examples 1, 2, 3, 4, 5, 6, and 24. Such branched reagents suitable for preparing a releasable GLP-1 conjugate include N-{di(mPEG(20,000)oxymethylcarbonylamino)fluoren-9-ylmethoxycarbonyloxy}succinimide, N-[2,7 di(4 mPEG(10,000)aminocarbonylbutyrylamino)fluoren-9 ylmethoxycarbonyloxy]-succinimide ("G2PEG2Fmoc$_{20k}$-NHS"), and PEG2-CAC-Fmoc$_{4k}$-BTC (Example 24). Of course, PEGs of any molecular weight as set forth herein may be employed in the above structures, and the particular activating groups described above are not meant to be limiting in any respect, and may be substituted by any other suitable activating group suitable for reaction with a reactive group present on the GLP-1 moiety.

Those of ordinary skill in the art will recognize that the foregoing discussion describing water-soluble polymers for use in forming a GLP-1 conjugate is by no means exhaustive and is merely illustrative, and that all polymeric materials having the qualities described above are contemplated. As used herein, the term "polymeric reagent" generally refers to an entire molecule, which can comprise a water-soluble polymer segment, as well as additional spacers and functional groups.

GLP-1 Conjugates

As described above, a conjugate of the invention comprises a water-soluble polymer covalently attached (either directly or through a spacer or linker moiety) to a GLP-1 moiety. Typically, for any given conjugate, there will be one to four water-soluble polymers covalently attached to a GLP-1 moiety (wherein for each water-soluble polymer, the water-soluble polymer can be attached either directly to the GLP-1 moiety or through a spacer moiety).

That is to say, a GLP-1 conjugate of the invention typically has 1, 2, 3, or 4 water-soluble polymers individually attached to a GLP-1 moiety. That is to say, in certain embodiments, a conjugate of the invention will possess not more than 4 water-soluble polymers individually attached to a GLP-1 moiety, or not more than 3 water-soluble polymers individually attached to a GLP-1 moiety, or not more than 2 water-soluble polymers individually attached to a GLP-1 moiety, or not more than 1 water-soluble polymer attached to a GLP-1 moiety. Preferably, the structure of each of the water-soluble polymers attached to the GLP-1 moiety is the same. One particularly preferred GLP-1 conjugate in accordance with the invention is one having a water-soluble polymer releasably attached to the N-terminus of GLP-1. Additional water-soluble polymers may be releasably attached to other sites on the GLP-1 moiety, e.g., such as one or two additional sites. For example, a GLP-1 conjugate having a water-soluble polymer releasably attached to the N-terminus may additionally possess a water-soluble polymer releasably attached Lys26, and/or to Lys34. Another particular preferred conjugate of the present invention is a mono-GLP-1 polymer conjugate, i.e., a GLP-1 moiety having one water-soluble polymer covalently attached thereto. Even more preferably, the water-soluble polymer is one that is releasably attached to the GLP-1 moiety at its N-terminus.

Preferably, a GLP-1 polymer conjugate of the invention is absent a metal ion, i.e., the GLP-1 moiety is not chelated to a metal ion.

For the GLP-1 polymer conjugates described herein, the GLP-1 moiety may optionally possess one or more N-methyl substituents, e.g., at any one or more of positions 7-His, 8-Ala, and 9-Glutamic Acid. Alternatively, for the GLP-1 polymer conjugates described herein, the GLP-1 moiety may be glycosylated, e.g., having a mono- or disaccharide covalently described to one or more sites thereof. Particularly preferred glycosylation sites include the N-terminus, Ala8, Glu9, Thr11, Thr13, Ser14, Ser17, Ser18, Glu21, Gly22, Gln23, Lys26, and Lys34.

As discussed herein, the compounds of the present invention may be made by any of the various methods and techniques known and available to those skilled in the art.

The Linkage

The particular linkage between the GLP-1 moiety and the water-soluble polymer (or the spacer moiety that is attached to the water-soluble polymer) depends on a number of factors. Such factors include, for example, the particular linkage chemistry employed, the particular GLP-1 moiety, the available functional groups within the GLP-1 moiety (either for attachment to a polymer or conversion to a suitable attachment site), the possible presence of additional reactive functional groups within the GLP-1 moiety due to methylation and/or glycosylation, and the like.

In one or more embodiments of the invention, the linkage between the GLP-1 moiety and the water-soluble polymer is a releasable linkage. That is, the water-soluble polymer is cleaved (either through hydrolysis, an enzymatic processes, or otherwise), thereby resulting in the native or an unconjugated GLP-1 moiety. Preferably, the releasable linkage is a hydrolytically degradable linkage, where upon hydrolysis, the native GLP-1 moiety, or a slightly modified version thereof, is released. The releasable linkage may result in the water-soluble polymer (and any spacer moiety) detaching from the GLP-1 moiety in vivo (and in vitro) without leaving any fragment of the water-soluble polymer (and/or any spacer or linker moiety) attached to the GLP-1 moiety. Exemplary releasable linkages include carbonate, carboxylate ester, phosphate ester, thiolester, anhydrides, acetals, ketals, acyloxyalkyl ether, imines, carbamates, and orthoesters. Such linkages can be readily formed by reaction of the GLP-1 moiety and/or the polymeric reagent using coupling methods commonly employed in the art. Hydrolyzable linkages are often readily formed by reaction of a suitably activated polymer with a non-modified functional group contained within the GLP-1 moiety. Preferred positions for covalent attachment of a water-soluble polymer induce the N-terminal, the C-terminal, as well as the internal lysines. Preferred releasable linkages include carbamate and ester.

Generally speaking, a preferred GLP-1 conjugate of the invention will possess the following generalized structure:

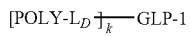

where POLY is a water-soluble polymer such as any of the illustrative polymer reagents provided in the tables herein, $L_D$ is a hydrolyzable linkage, and k is an integer selected from 1, 2, and 3. In the generalized structure above, $L_D$ refers to the hydrolyzable linkage per se (e.g., a carbamate or an ester linkage), while "POLY" is meant to include the polymer repeat units, e.g., $CH_3(OCH_2CH_2)_n$, as well as any additional linker or spacer atoms interposed between the polymer repeat units and the hyrolyzable linkage. In a preferred embodiment of the invention, at least one of the water-soluble polymer molecules is covalently attached to the N-terminus of GLP-1. In one embodiment of the invention, k equals 1 and $L_D$ is —O—C(O)—NH—, where the —NH— is part of the GLP-1 residue and represents an amino group thereof.

Although releasable linkages are preferred, the linkage between the GLP-1 moiety and the water-soluble polymer (or the linker moiety that is attached to the polymer) may be a hydrolytically stable linkage, such as an amide, a urethane (also known as carbamate), amine, thioether (also known as sulfide), or urea (also known as carbamide). One such embodiment of the invention comprises GLP-1 having a water-soluble polymer such as PEG covalently attached at the N-terminus of GLP-1. In such instances, alkylation of the N-terminal residue permits retention of the charge on the N-terminal nitrogen.

With regard to linkages, in one more embodiments of the invention, a conjugate is provided that comprises a GLP-1 moiety covalently attached at an amino acid residue, either directly or through a linker comprised of one or more atoms, to a water-soluble polymer.

The conjugates (as opposed to an unconjugated GLP-1 moiety) may or may not possess a measurable degree of GLP-1 activity. That is to say, a conjugate in accordance with the invention will typically possess anywhere from about 0% to about 100% or more of the bioactivity of the unmodified parent GLP-1 moiety. Typically, compounds possessing little or no GLP-1 activity contain a releasable linkage connecting the polymer to the GLP-1 moiety, so that regardless of the lack of activity in the conjugate, the active parent molecule (or a derivative thereof having GLP-1 activity) is released by degradation of the linkage (e.g., hydrolysis upon aqueous-induced cleavage of the linkage). Such activity may be determined using a suitable in vivo or in vitro model, depending upon the known activity of the particular moiety having GLP-1 activity employed.

Optimally, degradation of a linkage is facilitated through the use of hydrolytically cleavable and/or enzymatically degradable linkages such as urethane, amide, certain carbamate, carbonate or ester-containing linkages. In this way, clearance of the conjugate via cleavage of individual water-soluble polymer(s) can be modulated by selecting the polymer molecular size and the type of functional group for providing the desired clearance properties. In certain instances, a mixture of polymer conjugates is employed where the polymers possess structural or other differences effective to alter the release (hydrolysis rate) of the GLP-1 moiety, such that one can achieve a desired sustained delivery profile.

One of ordinary skill in the art can determine the proper molecular size of the polymer as well as the cleavable functional group, depending upon several factors including the mode of administration. For example, one of ordinary skill in the art, using routine experimentation, can determine a proper molecular size and cleavable functional group by first preparing a variety of polymer-(GLP-1) conjugates with different weight-average molecular weights, degradable functional groups, and chemical structures, and then obtaining the clearance profile for each conjugate by administering the conjugate to a patient and taking periodic blood and/or urine samples. Once a series of clearance profiles has been obtained for each tested conjugate, a conjugate or mixture of conjugates having the desired clearance profile(s) can be determined.

For conjugates possessing a hydrolytically stable linkage that couples the GLP-1 moiety to the water-soluble polymer, the conjugate will typically possess a measurable degree of GLP-1 activity. For instance, such conjugates are typically characterized as having a bioactivity satisfying one or more of the following percentages relative to that of the unconjugated GLP-1 moiety: at least about 2%, at least about 5%, at least about 10%, at least about 15%, at least about 25%, at least about 30%, at least about 40%, at least about 50%, at least about 60%, at least about 80%, at least about 85%, at least about 90%, at least about 95%, at least about 97%, at least about 100%, and more than 105% (when measured in a suitable model, such as those presented here and/or known in the art). Often, conjugates having a hydrolytically stable linkage (e.g., an amide linkage) will possess at least some degree of the bioactivity of the unmodified parent GLP-1 moiety. Due to their extended half-lives, Exemplary conjugates in accordance with the invention will now be described.

The GLP-1 moiety is expected to share (at least in part) an amino acid sequence similar or related to a human GLP-1. Thus, as previously indicated, while reference will be made to specific locations or atoms within a GLP-1 sequence, such a reference is for convenience only and one having ordinary skill in the art will be able to readily determine the corresponding location or atom in other moieties having GLP-1 activity. In particular, the description provided herein for a human GLP-1 is also often applicable not only to a human GLP-1, but to fragments, deletion variants, substation variants and addition variants of any of the foregoing.

Amino groups on a GLP-1 moiety provide a point of attachment between the GLP-1 moiety and the water-soluble polymer. For example, SEQ ID NOS. 1 and 2 each comprise two lysine residues, each lysine residue containing an ε-amino group that may be available for conjugation, as well as one amino terminus. See SEQ ID NO: 1 and SEQ ID NO: 2. Thus, exemplary attachment points include attachment at an amino acid (through the amine-containing side chain of a lysine residue) at either or both of positions 26 and 34. Typical attachment points of GLP-1 include attachment at any one of positions 26, 34, and the N-terminus. In one or more embodiments, attachment is a single attachment at one of positions 26, 34 or the N-terminus (His 7).

There are a number of examples of suitable water-soluble polymeric reagents useful for forming covalent linkages with available amines of a GLP-1 moiety. Certain specific examples, along with the corresponding conjugates, are provided in Table 1 below. In the table, the variable (n) represents the number of repeating monomeric units and "(GLP-1)" represents a GLP-1 moiety following conjugation to the water-soluble polymer. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefore.

As will be clearly understood by one skilled in the art, for conjugates such as those set forth below resulting from reaction with a GLP-1 amino group, the amino group extending from the GLP-1 designation "~NH-GLP-1" represents the residue of the GLP-1 moiety itself in which the ~NH— is an amino group of the GLP-1 moiety. One preferred site of attachment for the polymer reagents shown below is the N-terminus. Further, although the conjugates in the Tables herein illustrate a single water-soluble polymer covalently attached to a GLP-1 moiety, it will be understood that the conjugate structures on the right are meant to also encompass conjugates having more than one of such water-soluble polymer molecules covalently attached to GLP-1, e.g., 2, 3, or 4 water-soluble polymer molecules.

TABLE 1
Amine-Specific Polymeric Reagents and the GLP-1 Moiety Conjugate Formed Therefrom

TABLE 1-continued
Amine-Specific Polymeric Reagents and the GLP-1 Moiety Conjugate Formed Therefrom
| Polymeric Reagent | Corresponding Conjugate |
|---|---|
| 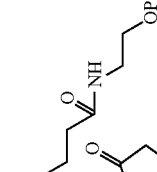 Fmoc-NHS Reagent | 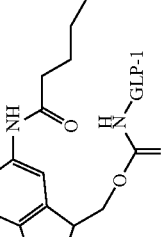 Carbamate Linkage |
| 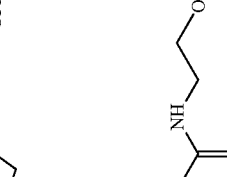 Fmoc-NHS Reagent | 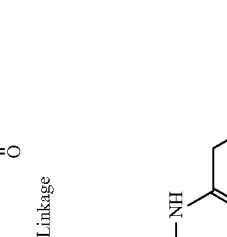 Carbamate Linkage |
| 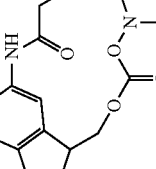 Fmoc-BTC Reagent | 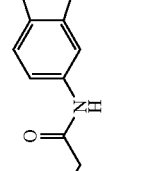 Carbamate Linkage |

TABLE 1-continued
Amine-Specific Polymeric Reagents and the GLP-1 Moiety Conjugate Formed Therefrom
| Polymeric Reagent | Corresponding Conjugate |
|---|---|
| 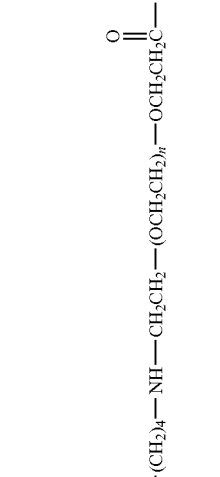 mPEG-Succinimidyl Reagent | 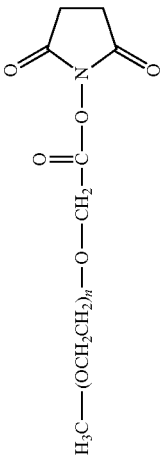 Amide Linkage |
| 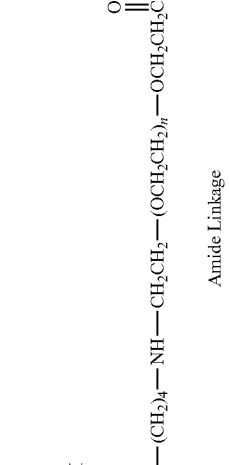 Homobifunctional PEG-Succinimidyl Reagent | 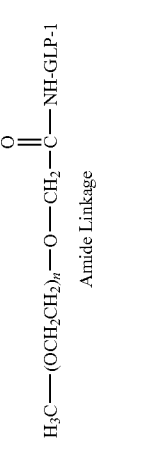 Amide Linkages |
| 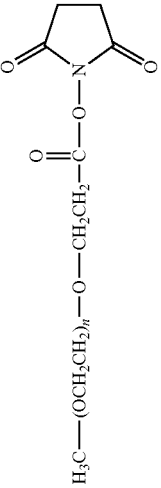 Heterobifunctional PEG-Succinimidyl Reagent | 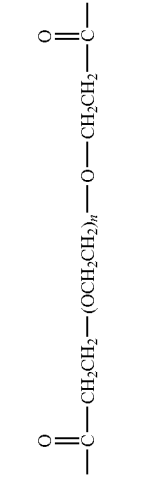 Amide Linkage |
| 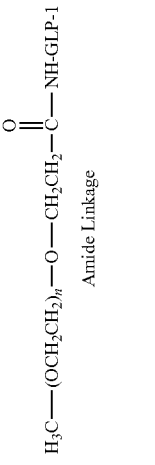 mPEG-Succinimidyl Reagent | 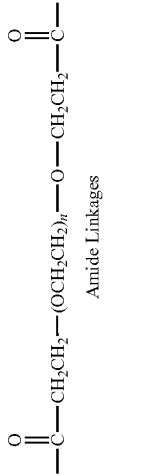 Amide Linkage |

TABLE 1-continued

Amine-Specific Polymeric Reagents and the GLP-1 Moiety Conjugate Formed Therefrom

| Polymeric Reagent | Corresponding Conjugate |
|---|---|
| $H_3CO-(CH_2CH_2O)_n-CH_2CH_2NH-C(=O)-CH_2CH_2-C(=O)-O-N(succinimidyl)$<br>mPEG-Succinimidyl Reagent | $H_3CO-(CH_2CH_2O)_n-CH_2CH_2NH-C(=O)-CH_2CH_2-C(=O)-NH-GLP-1$<br>Amide Linkage |
| $H_3CO-(CH_2CH_2O)_n-CH_2CH_2SH-CH_2CH_2-C(=O)-O-N(succinimidyl)$<br>mPEG Succinimidyl Reagent | $H_3CO-(CH_2CH_2O)_n-CH_2CH_2SH-CH_2CH_2-C(=O)-O-NH-GLP-1$<br>Amide Linkage |
| $H_3C-(OCH_2CH_2)_n-O-CH_2CH_2-C(=O)-O-N(succinimidyl)$<br>mPEG-Succinimidyl Reagent | $H_3C-(OCH_2CH_2)_n-O-CH_2CH_2-C(=O)-NH-GLP-1$<br>Amide Linkage |
| $H_3C-(OCH_2CH_2)_n-O-C(=O)-O-\text{benzotriazole}$<br>mPEG-Benzotriazole Carbonate Reagent | $H_3C-(OCH_2CH_2)_n-O-C(=O)-NH-GLP-1$<br>Carbamate Linkage |

TABLE 1-continued

Amine-Specific Polymeric Reagents and the GLP-1 Moiety Conjugate Formed Therefrom

| Polymeric Reagent | Corresponding Conjugate |
|---|---|
| H₃C—(OCH₂CH₂)ₙ—O—C(=O)—O—C₆H₄—C(=O)—O—N-succinimidyl<br>mPEG-Succinimidyl Reagent | H₃C—(OCH₂CH₂)ₙ—NH—C(=O)—O—C₆H₄—C(=O)—NH-GLP-1<br>Carbamate Linkage |
| H₃CO—(CH₂CH₂O)ₙ—C₆H₄—C(=O)—O—N-succinimidyl<br>mPEG-Succinimidyl Reagent | H₃CO—(CH₂CH₂O)ₙ—C₆H₄—C(=O)—NH-GLP-1<br>Amide Linkage |
| H₃CO—(CH₂CH₂O)ₙ—C(=O)—O—N-succinimidyl<br>mPEG-Succinimidyl Reagent | H₃CO—(CH₂CH₂O)ₙ—C(=O)—NH-GLP-1<br>Amide Linkage |
| H₃C—(OCH₂CH₂)ₙ—O—C(=O)—NH—CH₂—CH₂—CH₂—CH₂—CH(NH—C(=O)—O—(CH₂CH₂O)ₙ—CH₃)—C(=O)—O—N-succinimidyl<br>Branched mPEG2-N-Hydroxysuccinimide Reagent | H₃C—(OCH₂CH₂)ₙ—O—C(=O)—NH—CH₂—CH₂—CH₂—CH₂—CH(NH—C(=O)—O—(CH₂CH₂O)ₙ—CH₃)—C(=O)—NH-GLP-1<br>Amide Linkage |

TABLE 1-continued

Amine-Specific Polymeric Reagents and the GLP-1 Moiety Conjugate Formed Therefrom

| Polymeric Reagent | Corresponding Conjugate |
|---|---|
| Branched mPEG2-Aldehyde Reagent | Secondary Amine Linkage |
| mPEG-Succinimidyl Reagent | Amide Linkage |
| mPEG-Succinimidyl Reagent | Amide Linkage |
| Homobifunctional PEG-Succinimidyl Reagent | Amide Linkages |

TABLE 1-continued

Amine-Specific Polymeric Reagents and the GLP-1 Moiety Conjugate Formed Therefrom

| Polymeric Reagent | Corresponding Conjugate |
|---|---|
| 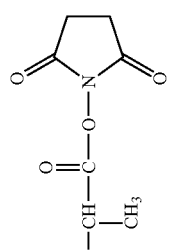<br>mPEG-Succinimidyl Reagent | 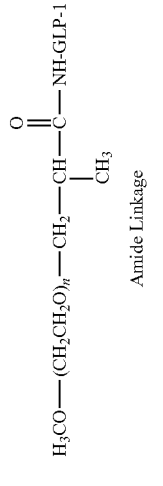<br>Amide Linkage |
| 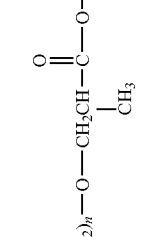<br>Homobifunctional PEG-Succinimidyl Propionate Reagent | 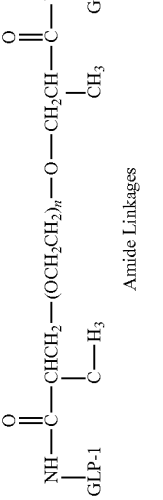<br>Amide Linkages |
| 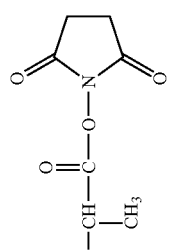<br>mPEG-Succinimidyl Reagent | 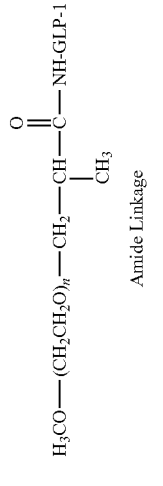<br>Amide Linkage |
| 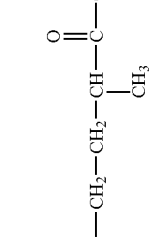<br>Branched mPEG2-N-Hydroxysuccinimide Reagent | 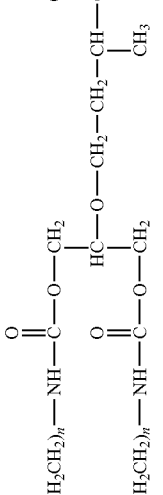<br>Amide Linkage |

TABLE 1-continued

Amine-Specific Polymeric Reagents and the GLP-1 Moiety Conjugate Formed Therefrom

| Polymeric Reagent | Corresponding Conjugate |
|---|---|
| $H_3C-(OCH_2CH_2)_n-NH-\overset{O}{\underset{\|}{C}}-CH_2-CH_2-\overset{O}{\underset{\|}{C}}-O-CH_2$<br>$\qquad HC-O-CH_2-CH_2-\overset{O}{\underset{\|}{C}}-O-N\underset{O}{\overset{O}{\diagup\diagdown}}$<br>$H_3C-(OCH_2CH_2)_n-NH-\overset{O}{\underset{\|}{C}}-CH_2-CH_2-\overset{O}{\underset{\|}{C}}-O-CH_2$<br>Branched mPEG2-N-Hydroxysuccinimide Reagent | $H_3C-(OCH_2CH_2)_n-NH-\overset{O}{\underset{\|}{C}}-CH_2-CH_2-\overset{O}{\underset{\|}{C}}-O-CH_2$<br>$\qquad HC-O-CH_2-CH_2-\overset{O}{\underset{\|}{C}}-NH-GLP-1$<br>$H_3C-(OCH_2CH_2)_n-NH-\overset{O}{\underset{\|}{C}}-CH_2-CH_2-\overset{O}{\underset{\|}{C}}-O-CH_2$<br>Amide Linkage |
| $H_3C-(OCH_2CH_2)_n-O-CH_2-CH_2-\overset{O}{\underset{\|}{C}}-S-\underset{\diagdown N\diagup}{\bigcirc}$<br>mPEG-Thioester Reagent | $H_3C-(OCH_2CH_2)_n-O-CH_2-CH_2-\overset{O}{\underset{\|}{C}}-NH-GLP-1$<br>Amide Linkage |
| $H-\overset{O}{\underset{\|}{C}}-CH_2CH_2-(OCH_2CH_2)_n-O-CH_2CH_2-\overset{O}{\underset{\|}{C}}-H$<br>Homobifunctional PEG Propionaldehyde Reagent | $\underset{GLP-1}{NH}-CH_2-CH_2CH_2-(OCH_2CH_2)_n-O-CH_2CH_2-CH_2-\underset{GLP-1}{NH}$<br>Secondary Amine Linkages |
| $H_3C-(OCH_2CH_2)_n-O-CH_2CH_2-\overset{O}{\underset{\|}{C}}-H$<br>mPEG Propionaldehyde Reagent | $H_3C-(OCH_2CH_2)_n-O-CH_2CH_2-CH_2-NH-GLP-1$<br>Secondary Amine Linkage |
| $\overset{O}{\underset{\|}{HC}}CH_2CH_2-(OCH_2CH_2)_n-O-CH_2CH_2-\overset{O}{\underset{\|}{C}}-H$<br>Homobifunctional PEG Butyraldehyde Reagent | $\underset{GLP-1}{NH}-CH_2-CH_2CH_2-(OCH_2CH_2)_n-O-CH_2CH_2-CH_2-\underset{GLP-1}{NH}$<br>Secondary Amine Linkages |
| $H_3C-(OCH_2CH_2)_n-O-CH_2CH_2-\overset{O}{\underset{\|}{C}}-H$<br>mPEG Butyraldehyde Reagent | $H_3C-(OCH_2CH_2)_n-O-CH_2CH_2-CH_2-NH-GLP-1$<br>Secondary Amine Linkage |
| $H_3C-(OCH_2CH_2)_n-O-\overset{O}{\underset{\|}{C}}-NH-(CH_2CH_2O)_4-CH_2CH_2CH_2CH$<br>mPEG Butyraldehyde Reagent | $H_3C-(OCH_2CH_2)_n-O-\overset{O}{\underset{\|}{C}}-NH-(CH_2CH_2O)_4-CH_2CH_2CH_2CH_2-\underset{GLP-1}{NH}$<br>Secondary Amine Linkage |

TABLE 1-continued

Amine-Specific Polymeric Reagents and the GLP-1 Moiety Conjugate Formed Therefrom

| Polymeric Reagent | Corresponding Conjugate |
|---|---|
| $H_3C-(OCH_2CH_2)_n-O-\overset{O}{\underset{\|}{C}}-NH-(CH_2CH_2O)_4-CH_2CH_2CH$ <br> Homobifunctional PEG Butyraldehyde Reagent | $\overset{O}{\underset{\|}{C}}-(OCH_2CH_2)_n-O-\overset{O}{\underset{\|}{C}}-NH-(CH_2CH_2O)_4-CH_2CH_2CH_2-NH\text{-}GLP\text{-}1$ <br> $HN-(CH_2CH_2O)_4-CH_2CH_2CH_2-NH\text{-}GLP\text{-}1$ <br> Secondary Amine Linkages |
| $H_3C-(OCH_2CH_2)_n-O-\overset{O}{\underset{\|}{C}}-NH-CH_2-CH_2-CH_2-CH_2$ <br> $\phantom{HHHHHH}CH-\overset{O}{\underset{\|}{C}}-NH-(CH_2CH_2O)_4-CH_2CH_2CH$ <br> $H_3C-(OCH_2CH_2)_n-O-\overset{O}{\underset{\|}{C}}-NH$ <br> Branched mPEG2 Butyraldehyde Reagent | $H_3C-(OCH_2CH_2)_n-O-\overset{O}{\underset{\|}{C}}-NH-CH_2-CH_2-CH_2-CH_2$ <br> $\phantom{HHHHHH}CH-$ <br> $\phantom{HHHHHH}\overset{O}{\underset{\|}{C}}-NH$ <br> $H_3C-(OCH_2CH_2)_n-O-\overset{O}{\underset{\|}{C}}-NH$ <br> Secondary Amine Linkage |
| $H_3C-(OCH_2CH_2)_n-NH-\overset{O}{\underset{\|}{C}}-O-CH_2$ <br> $\phantom{HHHHHHHH}HC-O-CH_2-CH_2-CH_2$ <br> $H_3C-(OCH_2CH_2)_n-NH-\overset{O}{\underset{\|}{C}}-O-CH_2$ <br> Branched mPEG2 Butyraldehyde Reagent | $H_3C-(OCH_2CH_2)_n-NH-\overset{O}{\underset{\|}{C}}-O-CH_2$ <br> $\phantom{HHHHHHHH}HC-O-CH_2-CH_2-CH_2-$ <br> $H_3C-(OCH_2CH_2)_n-NH-\overset{O}{\underset{\|}{C}}-O-CH_2$ <br> $\overset{O}{\underset{\|}{C}}-NH-(CH_2CH_2O)_4-CH_2CH_2CH_2-NH\text{-}GLP\text{-}1$ <br> Secondary Amine Linkage |
| $\phantom{HHHHH}OCH_2CH_3$ <br> $H_3C-(OCH_2CH_2)_n-O-CH_2-CH-OCH_2CH_3$ <br> mPEG Acetal Reagent | $H_3C-(OCH_2CH_2)_n-O-CH_2CH_2-NH\text{-}GLP\text{-}1$ <br> Secondary Amine Linkage |

TABLE 1-continued

Amine-Specific Polymeric Reagents and the GLP-1 Moiety Conjugate Formed Therefrom

| Polymeric Reagent | Corresponding Conjugate |
|---|---|
|  H$_3$C—(OCH$_2$CH$_2$)$_n$—O—CH$_2$CH$_2$—C(=O)—[piperidone]<br>mPEG Piperidone Reagent | 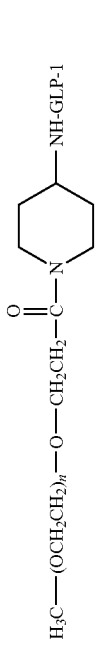 H$_3$C—(OCH$_2$CH$_2$)$_n$—O—CH$_2$CH$_2$—C(=O)—[piperidine]—NH-GLP-1<br>Secondary Amine Linkage<br>(to a secondary carbon) |
| 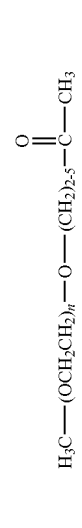 H$_3$C—(OCH$_2$CH$_2$)$_n$—O—(CH$_2$)$_{2-5}$—C(=O)—CH$_3$<br>mPEG Methylketone Reagent | H$_3$C—(OCH$_2$CH$_2$)$_n$—O—(CH$_2$)$_{2-5}$—CH(NH-GLP-1)—CH$_3$<br>secondary amine linkage<br>(to a secondary carbon) |
|  H$_3$CO—(CH$_2$CH$_2$O)$_n$—S(=O)$_2$—CH$_2$—CF$_3$<br>mPEG Tresylate Reagent | H$_3$CO—(CH$_2$CH$_2$O)$_n$—CH$_2$CH$_2$—NH-GLP-1<br>Secondary Amine Linkage |
| 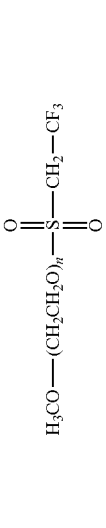 H$_3$C—(OCH$_2$CH$_2$)$_n$—O—CH$_2$CH$_2$—[maleimide]<br>mPEG Maleimide Reagent<br>(under certain reaction conditions such as pH > 8) |  H$_3$C—(OCH$_2$CH$_2$)$_n$—O—CH$_2$CH$_2$—[succinimide-NH-GLP-1]<br>Secondary Amine Linkage |
|  H$_3$C—(OCH$_2$CH$_2$)$_n$—O—CH$_2$CH$_2$—NH—C(=O)—CH$_2$CH$_2$—[maleimide]<br>mPEG Maleimide Reagent<br>(under certain reaction conditions such as pH > 8) |  H$_3$C—(OCH$_2$CH$_2$)$_n$—O—CH$_2$CH$_2$—NH—C(=O)—CH$_2$CH$_2$—[succinimide-NH-GLP-1]<br>Secondary Amine Linkage |

TABLE 1-continued

Amine-Specific Polymeric Reagents and the GLP-1 Moiety Conjugate Formed Therefrom

| Polymeric Reagent | Corresponding Conjugate |
|---|---|
| $H_3C-(OCH_2CH_2)_n-O-CH_2CH_2-C-NH-CH_2CH_2-NH-C-CH_2CH_2-$ [maleimide] <br> mPEG Maleimide Reagent <br> (under certain reaction conditions such as pH > 8) | $H_3C-(OCH_2CH_2)_n-O-CH_2CH_2-C-NH-CH_2CH_2-NH-C-CH_2CH_2-$ [succinimide-NH-GLP-1] <br> Secondary Amine Linkage |
| $H_3C-(OCH_2CH_2)_n-O-CH_2CH_2-C-NH-CH_2CH_2-C-NH$ <br> with forked $-NH-CH_2CH_2-C(=O)-CH_2-CH(-)-CH_2-C(=O)-NH-CH_2CH_2-$ branches to two maleimides <br> mPEG Forked Maleimide Reagent <br> (under certain reaction conditions such as pH > 8) | Corresponding conjugate with two succinimide-NH-GLP-1 groups <br> Secondary Amine Linkages |

TABLE 1-continued

Amine-Specific Polymeric Reagents and the GLP-1 Moiety Conjugate Formed Therefrom

| Polymeric Reagent | Corresponding Conjugate |
|---|---|

Branched mPEG2 Maleimide Reagent
(under certain reaction conditions such as pH > 8)

Secondary Amine Linkage

Amine Conjugation and Resulting Conjugates

Conjugation of a polymeric reagent to an amine group of a GLP-1 moiety can be accomplished by a variety of techniques. In one approach, a GLP-1 moiety is conjugated to a polymeric reagent functionalized with an active ester such as a succinimidyl derivative (e.g., an N-hydroxysuccinimide ester). In this approach, the polymeric reagent bearing the reactive ester is reacted with the GLP-1 moiety in aqueous media under appropriate pH conditions, e.g., from pHs ranging from about 3 to about 8, about 3 to about 7, or about 4 to about 6.5. Most polymer active esters can couple to a target protein such as GLP-1 at physiological pH, e.g., at 7.0. However, less reactive derivatives may require a higher pH. Typically, activated PEGs can be attached to a protein such as GLP-1 at pHs from about 7.0 to about 10.0 for covalent attachment to an internal lysine. Typically, lower pHs are used, e.g., 4 to about 5.75, for preferential covalent attachment to the N-terminus. Thus, different reaction conditions (e.g., different pHs or different temperatures) can result in the attachment of a water-soluble polymer such as PEG to different locations on the GLP-1 moiety (e.g., internal lysines versus the N-terminus). Coupling reactions can often be carried out at room temperature, although lower temperatures may be required for particularly labile GLP-1 moieties. Reaction times are typically on the order of minutes, e.g., 30 minutes, to hours, e.g., from about 1 to about 36 hours), depending upon the pH and temperature of the reaction. N-terminal PEGylation, e.g., with a PEG reagent bearing an aldehyde group, is typically conducted under mild conditions, pHs from about 5-10, for about 6 to 36 hours. Varying ratios of polymer reagent to GLP-1 moiety may be employed, e.g., from an equimolar ratio up to a 10-fold molar excess of polymer reagent. Typically, up to a 5-fold molar excess of polymer reagent will suffice.

In certain instances, it may be preferable to protect certain amino acids from reaction with a particular polymer reagent if site specific covalent attachment is desired using commonly employed protection/deprotection methodologies such as those well known in the art. Mono-GLP-1 conjugates selectively conjugated at the N-terminus of GLP-1 were prepared as described in detail in the Examples herein without the need to employ protection/deprotection strategies.

In an alternative approach to direct coupling reactions, the PEG reagent may be incorporated at a desired position of the GLP-1 moiety during peptide synthesis. In this way, site-selective introduction of one or more PEGs can be achieved. See, e.g., International Patent Publication No. WO 95/00162, which describes the site selective synthesis of conjugated peptides.

Exemplary conjugates that can be prepared using, for example, polymeric reagents containing a reactive ester for coupling to an amino group of GLP-1, comprise the following alpha-branched structure:

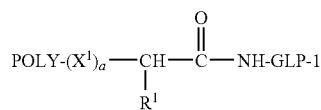

where POLY is a water-soluble polymer, (a) is either zero or one; $X^1$, when present, is a spacer moiety comprised of one or more atoms; $R^1$ is hydrogen an organic radical; and "~NH-GLP-1" represents a residue of a GLP-1 moiety, where the underlined amino group represents an amino group of the GLP-1 moiety.

With respect to the structure corresponding to that referred to in the immediately preceding paragraph, any of the water-soluble polymers provided herein can be defined as POLY, any of the spacer moieties provided herein can be defined as $X^1$ (when present), any of the organic radicals provided herein can be defined as $R^1$ (in instances where $R^1$ is not hydrogen), and any of the GLP-1 moieties provided herein can be defined as GLP-1. In one or more embodiments corresponding to the structure referred to in the immediately preceding paragraph, POLY is a poly(ethylene glycol) such as $H_3CO(CH_2CH_2O)_n$—, wherein (n) is an integer having a value of from 3 to 4000, more preferably from 10 to about 1800; (a) is one; $X^1$ is a $C_{1-6}$ alkylene, such as one selected from methylene (i.e., —$CH_2$—), ethylene (i.e., —$CH_2$—$CH_2$—) and propylene (i.e., —$CH_2$—$CH_2$—$CH_2$—); $R^1$ is H or lower alkyl such as methyl or ethyl; and GLP-1 corresponds to SEQ ID NO:1 or SEQ ID NO:2.

Typical of another approach for conjugating a GLP-1 moiety to a polymeric reagent is reductive amination. Typically, reductive amination is employed to conjugate a primary amine of a GLP-1 moiety with a polymeric reagent functionalized with a ketone, aldehyde or a hydrated form thereof (e.g., ketone hydrate and aldehyde hydrate). In this approach, the primary amine from the GLP-1 moiety (e.g., the N-terminus) reacts with the carbonyl group of the aldehyde or ketone (or the corresponding hydroxy-containing group of a hydrated aldehyde or ketone), thereby forming a Schiff base. The Schiff base, in turn, is then reductively converted to a stable conjugate through use of a reducing agent such as sodium borohydride or any other suitable reducing agent. Selective reactions (e.g., at the N-terminus are possible) are possible, particularly with a polymer functionalized with a ketone or an alpha-methyl branched aldehyde and/or under specific reaction conditions (e.g., reduced pH).

Exemplary conjugates that can be prepared using, for example, polymeric reagents containing an aldehyde (or aldehyde hydrate) or ketone or (ketone hydrate) possess the following structure:

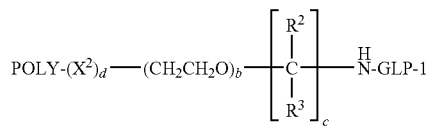

where POLY is a water-soluble polymer; (d) is either zero or one; $X^2$, when present, is a spacer moiety comprised of one or more atoms; (b) is an integer having a value of one through ten; (c) is an integer having a value of one through ten; $R^2$, in each occurrence, is independently H or an organic radical; $R^3$, in each occurrence, is independently H or an organic radical; and "~NH-GLP-1" represents a residue of a GLP-1 moiety, where the underlined amino group represents an amino group of the GLP-1 moiety.

Yet another illustrative conjugate of the invention possesses the structure:

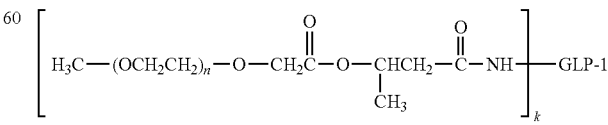

where k ranges from 1 to 3, and n ranges from 10 to about 1800.

With respect to the structure corresponding to that referred to in immediately preceding paragraph, any of the water-soluble polymers provided herein can be defined as POLY, any of the spacer moieties provided herein can be defined as $X^2$ (when present), any of the organic radicals provided herein can be independently defined as $R^2$ and $R^3$ (in instances where $R^2$ and $R^3$ are independently not hydrogen), and any of the GLP-1 moieties provided herein can be defined as GLP-1. In one or more embodiments of the structure referred to in the immediately preceding paragraph, POLY is a poly(ethylene glycol) such as $H_3CO(CH_2CH_2O)_n$—, wherein (n) is an integer having a value of from 3 to 4000, more preferably from 10 to about 1800; (d) is one; $X^1$ is amide [e.g., —C(O)NH—]; (b) is 2 through 6, such as 4; (c) is 2 through 6, such as 4; each of $R^2$ and $R^3$ are independently H or lower alkyl, such as methyl when lower alkyl; and GLP-1 is human GLP-1.

Another example of a GLP-1 conjugate in accordance with the invention has the following structure:

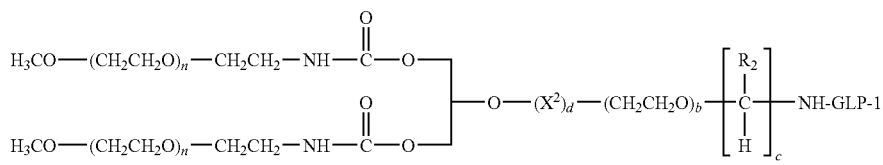

wherein each (n) is independently an integer having a value of from 3 to 4000, preferably from 10 to 1800; $X^2$ is as previously defined; (b) is 2 through 6; (c) is 2 through 6; $R^2$, in each occurrence, is independently H or lower alkyl; and "~NH—GLP-1" represents a residue of a GLP-1 moiety, where the underlined amino group represents an amino group of the GLP-1 moiety.

Additional GLP-1 polymer conjugates resulting from reaction of a water-soluble polymer with an amino group of GLP-1 are provided below. The following conjugate structures are releasable. One such structure corresponds to:

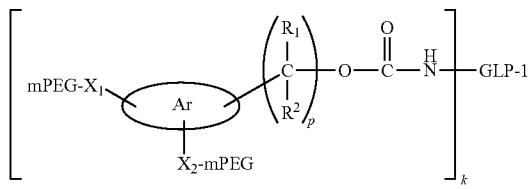

where mPEG is $CH_3O$—$(CH_2CH_2O)_n CH_2CH_2$—, n ranges from 10 to 1800, p is an integer ranging from 1 to 8, $R_1$ is H or lower alkyl, $R_2$ is H or lower alkyl, Ar is an aromatic hydrocarbon, such as a fused bicyclic or tricyclic aromatic hydrocarbon, $X_1$ and $X_2$ are each independently a spacer moiety having an atom length of from about 1 to about 18 atoms, ~NH-GLP-1 is as previously described, and k is an integer selected from 1, 2, and 3. The value of k indicates the number of water-soluble polymer molecules attached to different sites on the GLP-1 moiety. In a preferred embodiment, $R_1$ and $R_2$ are both H. The spacer moieties, $X_1$ and $X_2$, preferably each contain one amide bond. In a preferred embodiment, $X_1$ and $X_2$ are the same. Preferred spacers, i.e., $X_1$ and $X_2$, include —NH—C(O)—$CH_2$—O—, —NH—C(O)—$(CH_2)_q$—O—, —NH—C(O)—$(CH_2)_q$—C(O)—NH—, —NH—C(O)—$(CH_2)_q$—, and —C(O)—NH—, where q is selected from 2, 3, 4, and 5. Although the spacers can be in either orientation, preferably, the nitrogen is proximal to the PEG rather than to the aromatic moiety. Illustrative aromatic moieties include pentalene, indene, naphthalene, indacene, acenaphthylene, and fluorene.

Particularly preferred conjugates of this type are provided below.

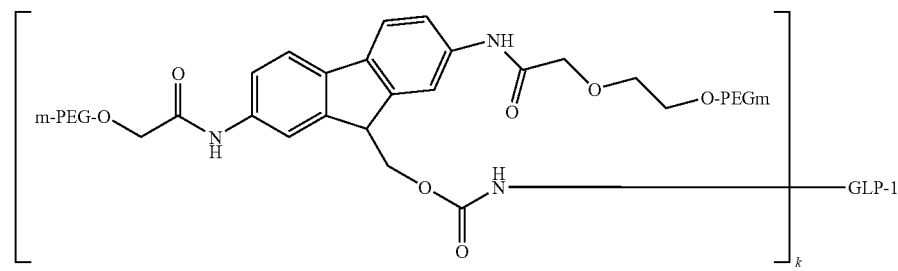

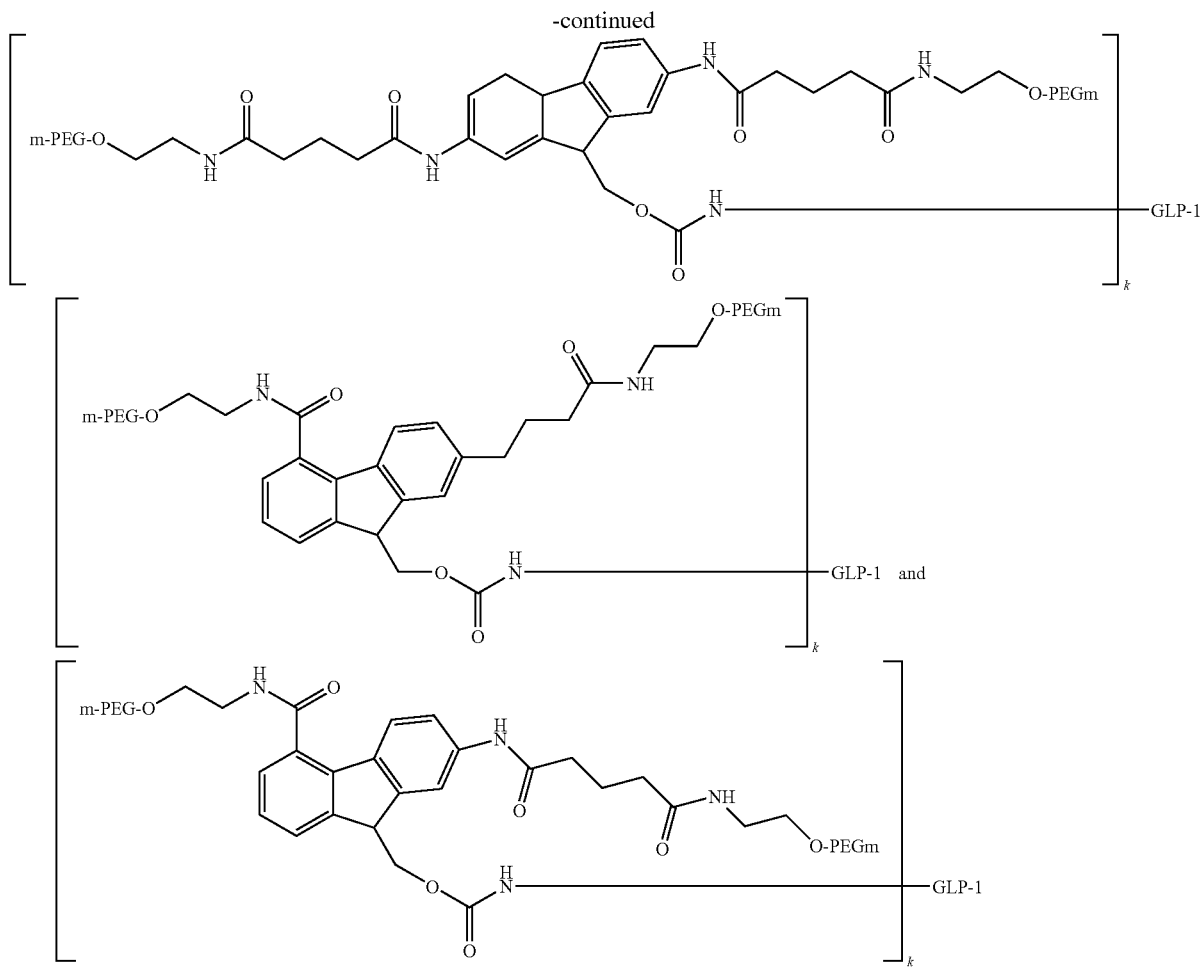

Additional GLP-1 conjugates resulting from covalent attachment to amino groups of GLP-1 that are also releasable include the following:

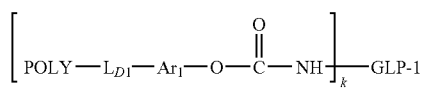

where $L_{D1}$ is either —O— or —NH—C(O)—, $Ar_1$ is an aromatic group, e.g., ortho, meta, or para-substituted phenyl, and k is an integer selected from 1, 2, and 3. Particular conjugates of this type include:

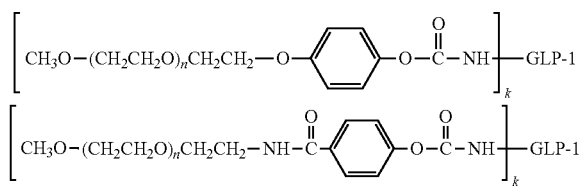

where n ranges from about 10 to about 1800.

Additional releasable conjugates in accordance with the invention are prepared using water-soluble polymer reagents such as those described in U.S. Pat. No. 6,214,966. Such water-soluble polymers are degradable, and possess at least one hydrolytically degradable ester linkage close to the covalent attachment to the active agent. The polymers generally possess the following structure, PEG-W—CO$_2$—NHS or an equivalent activated ester, where W=—O$_2$C—(CH$_2$)$_b$—O— b=1-5

—O—(CH$_2$)$_b$CO$_2$—(CH$_2$)$_c$— b=1-5, c=2-5

—O—(CH$_2$)$_b$—CO$_2$—(CH$_2$)$_c$—O— b=1-5, c=2-5 and NHS is N-hydroxysuccinimidyl. Upon hydrolysis, the resulting released active agent, e.g., GLP-1, will possess a short tag resulting from hydrolysis of the ester functionality of the polymer reagent. Illustrative releasable conjugates of this type include: mPEG-O—(CH$_2$)$_b$—COOCH$_2$C(O)—NH-GLP-1, and mPEG-O—(CH$_2$)$_b$—COO—CH(CH$_3$)—CH$_2$—C(O)—NH-GLP-1, where the number of water-soluble polymers attached to GLP-1 can be anywhere from 1 to 4, or more preferably, from 1 to 3.

Carboxyl Coupling and Resulting Conjugates

Carboxyl groups represent another functional group that can serve as a point of attachment to the GLP-1 moiety. Structurally, the conjugate will comprise the following:

(GLP-1)—C(O)—X-POLY where GLP-1-C(O)–corresponds to a residue of a GLP-1 moiety where the carbonyl is a carbonyl (derived from the carboxy group) of the GLP-1 moiety, X is a spacer moiety, such as a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing GLP-1 moiety. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linker structure.

ety, along with the corresponding conjugates, are provided in Table 2, below. In addition, any polymeric reagent comprising an activated ester (e.g., a succinimidyl group) can be converted to contain a hydrazide moiety by reacting the polymer activated ester with hydrazine ($NH_2$—$NH_2$) or tert-butyl carbazate [$NH_2NHCO_2C(CH_3)_3$]. In the table, the variable (n) represents the number of repeating monomeric units and "=C-(GLP-1)" represents a residue of a GLP-1 moiety following conjugation to the polymeric reagent were the underlined C is part of the GLP-1 moiety. Optionally, the hydrazone linkage can be reduced using a suitable reducing agent. While each polymeric portion [e.g., $(OCH_2CH_2)_n$ or $(CH_2CH_2O)_n$] presented in Table 2 terminates in a "$CH_3$" group, other groups (such as H and benzyl) can be substituted therefor.

TABLE 2

Carboxyl-Specific Polymeric Reagents and the GM-GLP-1 Moiety Conjugate Formed Therefrom

| Polymeric Reagent | Corresponding Conjugate |
|---|---|
| $H_3CO-(CH_2CH_2O)_nCH_2CH_2-C(=O)-NH-NH_2$<br>mPEG-Hydrazine Reagent | $H_3CO-(CH_2CH_2O)_nCH_2CH_2-C(=O)-NH-N=C\text{-GLP-1}$<br>Hydrazone Linkage |
| $H_3CO-(CH_2CH_2O)_nCH_2CH_2-O-CH_2-C(=O)-NH-NH_2$<br>mPEG-Hydrazine Reagent | $H_3CO-(CH_2CH_2O)_nCH_2CH_2-O-CH_2-C(=O)-NH-N=C\text{-GLP-1}$<br>Hydrazone Linkage |
| $H_3CO-(CH_2CH_2O)_nCH_2CH_2-NH-C(=O)-NH-NH_2$<br>mPEG-Hydrazine Reagent | $H_3CO-(CH_2CH_2O)_nCH_2CH_2-NH-C(=O)-NH-N=C\text{-GLP-1}$<br>Hydrazone Linkage |
| $H_3CO-(CH_2CH_2O)_nCH_2CH_2-NH-NH-C(=O)-NH-NH_2$<br>mPEG-Hydrazine Reagent | $H_3CO-(CH_2CH_2O)_nCH_2CH_2-NH-NH-C(=O)-NH-N=C\text{-GLP-1}$<br>Hydrazone Linkage |
| $H_3CO-(CH_2CH_2O)_nCH_2CH_2-NH-C(=S)-NH-NH_2$<br>mPEG-Hydrazine Reagent | $H_3CO-(CH_2CH_2O)_nCH_2CH_2-NH-C(=S)-NH-N=C\text{-GLP-1}$<br>Hydrazone Linkage |
| $H_3CO-(CH_2CH_2O)_nCH_2CH_2-NH-NH-C(=S)-NH-NH_2$<br>mPEG-Hydrazine Reagent | $H_3CO-(CH_2CH_2O)_nCH_2CH_2-NH-NH-C(=S)-NH-N=C\text{-GLP-1}$<br>Hydrazone Linkage |
| $H_3CO-(CH_2CH_2O)_nCH_2CH_2-NH-C(=O)-NH-NH-C(=O)-NH-NH_2$<br>mPEG-Hydrazine Reagent | $H_3CO-(CH_2CH_2O)_nCH_2CH_2-NH-C(=O)-NH-NH-C(=O)-NH-N=C\text{-GLP-1}$<br>Hydrazone Linkage |
| $H_3CO-(CH_2CH_2O)_nCH_2CH_2-O-C(=O)-NH-NH_2$<br>mPEG-Hydrazine Reagent | $H_3CO-(CH_2CH_2O)_nCH_2CH_2-O-C(=O)-NH-N=C\text{-GLP-1}$<br>Hydrazone Linkage |

Polymer reagents containing a hydrazide moiety are also suitable for conjugation at a carbonyl. To the extent that the GLP-1 moiety does not contain a carbonyl moiety, a carbonyl moiety can be introduced by reducing any carboxylic acid functionality (e.g., the C-terminal carboxylic acid). Specific examples of polymeric reagents comprising a hydrazide moi- Thiol Coupling and Resulting Conjugates Thiol groups contained within the GLP-1 moiety can serve as effective sites of attachment for the water-soluble polymer. The thiol groups contained in cysteine residues of the GLP-1 moiety can be reacted with an activated PEG that is specific for reaction with thiol groups, e.g., an N-maleimidyl polymer or other derivative, as described in, for example, U.S. Pat. No. 5,739,208, WO 01/62827, and in Table 3 below. GLP-1 moieties for use in this embodiment of the invention include those described in WO 2004/093823.

Specific examples of the reagents themselves, along with the corresponding conjugates, are provided in Table 3 below. In the table, the variable (n) represents the number of repeating monomeric units and "—S-(GLP-1)" represents a residue of a GLP-1 moiety following conjugation to the water-soluble polymer, where the S represents the residue of a GLP-1 thiol group, While each polymeric portion [e.g., $(OCH_2CH_2)_n$ or $(CH_2CH_2O)_n$] presented in Table 3 terminates in a "$CH_3$" group, other end-capping groups (such as H and benzyl) or reactive groups may be used as well.

TABLE 3
Thiol-Specific Polymeric Reagents and the GLP-1 Moiety Conjugate Formed Therefrom
| Polymeric Reagent | Corresponding Conjugate |
|---|---|
| 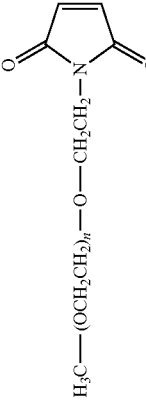<br>mPEG Maleimide Reagent | 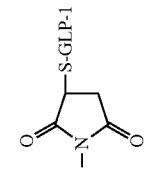<br>Thioether Linkage |
| <br>mPEG Maleimide Reagent | 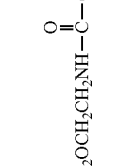<br>Thioether Linkage |
| <br>mPEG Maleimide Reagent | <br>Thioether Linkage |
| 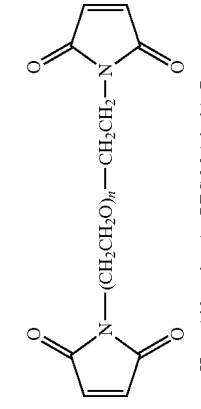<br>Homobifunctional mPEG Maleimide Reagent | <br>Thioether Linkages |

TABLE 3-continued

Thiol-Specific Polymeric Reagents and the GLP-1 Moiety Conjugate Formed Therefrom

| Polymeric Reagent | Corresponding Conjugate |
|---|---|
| $H_3C-(OCH_2CH_2)_n-O-CH_2CH_2-NH-C(=O)-CH_2CH_2$–maleimide<br>mPEG Maleimide Reagent | $H_3C-(OCH_2CH_2)_n-O-CH_2CH_2-NH-C(=O)-CH_2CH_2$–succinimide-S-GLP-1<br>Thioether Linkage |
| $H_3C-(OCH_2CH_2)_n-O-CH_2CH_2-NH-C(=O)-C(=O)-NH-CH_2CH_2$–maleimide<br>mPEG Maleimide Reagent | $H_3C-(OCH_2CH_2)_n-O-CH_2CH_2-NH-C(=O)-C(=O)-NH-CH_2CH_2$–succinimide-S-GLP-1<br>Thioether Linkage |
| $H_3C-(OCH_2CH_2)_n-O-CH_2CH_2$–[forked linker with two maleimides]<br>mPEG Forked Maleimide Reagent | $H_3C-(OCH_2CH_2)_n-O-CH_2CH_2$–[forked linker with two succinimide-S-GLP-1]<br>Thioether Linkage |

TABLE 3-continued

Thiol-Specific Polymeric Reagents and the GLP-1 Moiety Conjugate Formed Therefrom

| Polymeric Reagent | Corresponding Conjugate |
|---|---|
| Branched mPEG2 Maleimide Reagent | Thioether Linkage |
| Branched mPEG2 Maleimide Reagent | Thioether Linkage |

TABLE 3-continued

Thiol-Specific Polymeric Reagents and the GLP-1 Moiety Conjugate Formed Therefrom

| Polymeric Reagent | Corresponding Conjugate |
|---|---|
| Branched mPEG2 Forked Maleimide Reagent | Thioether Linkages |

TABLE 3-continued

Thiol-Specific Polymeric Reagents and the GLP-1 Moiety Conjugate Formed Therefrom

| Polymeric Reagent | Corresponding Conjugate |
|---|---|

Branched mPEG2 Forked Maleimide Reagent

Thioether Linkages mPEG Vinyl Sulfone Reagent $H_3C-(OCH_2CH_2)_n-O-CH_2CH_2-S(=O)_2-CH=CH_2$ $H_3C-(OCH_2CH_2)_n-O-CH_2CH_2-S(=O)_2-CH_2-CH_2-S-GLP-1$ Thioether Linkage mPEG Thiol Reagent $H_3C-(OCH_2CH_2)_n-O-CH_2CH_2-C(=O)-NH-CH_2-CH_2-SH$ $H_3C-(OCH_2CH_2)_n-O-CH_2CH_2-C(=O)-NH-CH_2-CH_2-S-S-GLP-1$ Disulfide Linkage TABLE 3-continued
Thiol-Specific Polymeric Reagents and the GLP-1 Moiety Conjugate Formed Therefrom

With respect to conjugates formed from water-soluble polymers bearing one or more maleimide functional groups (regardless of whether the maleimide reacts with an amine or thiol group on the GLP-1 moiety), the corresponding maleamic acid form(s) of the water-soluble polymer can also react with the GLP-1 moiety. Under certain conditions (e.g., a pH of about 7-9 and in the presence of water), the maleimide ring will "open" to form the corresponding maleamic acid. The maleamic acid, in turn, can react with an amine or thiol group of a GLP-1 moiety. Exemplary maleamic acid-based reactions are schematically shown below. POLY represents the water-soluble polymer, and ~S-GLP-1 represents a residue of a GLP-1 moiety, where the S is derived from a thiol group of the GLP-1.

substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess reagents, unconjugated reac-

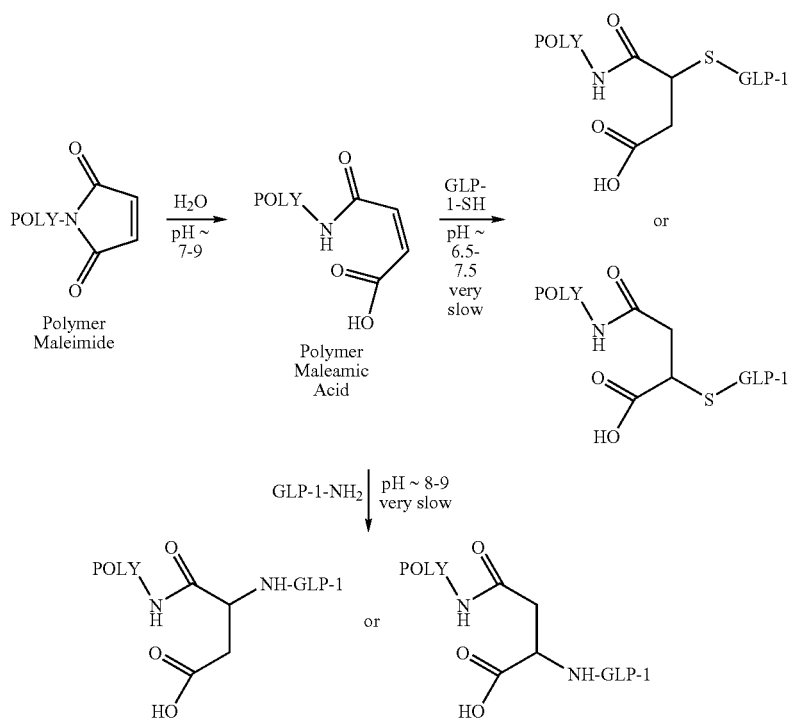

Thiol PEGylation is specific for free thiol groups on the GLP-1 moiety. Typically, a polymer maleimide is conjugated to a sulfhydryl-containing GLP-1 at pHs ranging from about 6-9 (e.g., at 6, 6.5, 7, 7.5, 8, 8.5, or 9), more preferably at pHs from about 7-9, and even more preferably at pHs from about 7 to 8. Generally, a slight molar excess of polymer maleimide is employed, for example, a 1.5 to 15-fold molar excess, preferably a 2-fold to 10 fold molar excess. Reaction times generally range from about 15 minutes to several hours, e.g., 8 or more hours, at room temperature. For sterically hindered sulfhydryl groups, required reaction times may be significantly longer. Thiol-selective conjugation is preferably conducted at pHs around 7. Temperatures for conjugation reactions are typically, although not necessarily, in the range of from about 0° C. to about 40° C.; conjugation is often carried out at room temperature or less. Conjugation reactions are often carried out in a buffer such as a phosphate or acetate buffer or similar system.

With respect to reagent concentration, an excess of the polymeric reagent is typically combined with the GLP-1 moiety. The conjugation reaction is allowed to proceed until tants (e.g., GLP-1) undesired multi-conjugated species, and free or unreacted polymer. The resulting conjugates can then be further characterized using analytical methods such as MALDI, capillary electrophoresis, gel electrophoresis, and/or chromatography.

An illustrative GLP-1 conjugate formed by reaction with one or more GLP-1 thiol groups may possess the following structure:

POLY-$L_{0,1}$-C(O)Z—Y—S—S-(GLP-1)

where POLY is a water-soluble polymer, L is an optional linker, Z is a heteroatom selected from the group consisting of O, NH, and S, and Y is selected from the group consisting of $C_{2-10}$alkyl, $C_{2-10}$ substituted alkyl, aryl, and substituted aryl, and S-GLP-1 is a residue of a GLP-1 moiety, where the S represents the residue of a GLP-1 thiol group. Such polymeric reagents suitable for reaction with a GLP-1 moiety to result in this type of conjugate are described in U.S. Patent Application Publication No. 2005/0014903, which is incorporated herein by reference.

With respect to polymeric reagents suitable for reacting with a GLP-1 thiol group, those described here and elsewhere can be obtained from commercial sources (e.g., Nektar Therapeutics, Huntsville Ala.). In addition, methods for preparing polymeric reagents are described in the literature.

Additional Conjugates and Features Thereof

As is the case for any GLP-1 polymer conjugate of the invention, the attachment between the GLP-1 moiety and water-soluble polymer can be direct, wherein no intervening atoms are located between the GLP-1 moiety and the polymer, or indirect, wherein one or more atoms are located between the GLP-1 moiety and polymer. With respect to the indirect attachment, a "spacer or linker moiety" serves as a link between the GLP-1 moiety and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties (including "X", $X^1$, $X^2$, and $X^3$) include those selected from the group consisting of —O—, —S—, —S—S—, —C(O)—, —C(O)—NH—, —NH—C(O)—NH—, —O—C(O)—NH—, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—, —C(O)—O—$CH_2$—, —$CH_2$—C(O)—O—$CH_2$—, —$CH_2$—$CH_2$—C(O)—O—$CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, —$CH_2$—$CH_2$—NH—C(O)—$CH_2$—, —$CH_2$—$CH_2$—$CH_2$— C(O)—NH—$CH_2$—$CH_2$—NH—C(O)—$CH_2$—$CH_2$—, —O—C(O)—NH—[$CH_2$]$_h$—(OCH2CH2)$_j$—, bivalent cycloalkyl group, —O—, —S—, an amino acid, —N($R^6$)—, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—($CH_2$)$_{1-6}$—NH—C(O)—, —NH—C(O)—NH—($CH_2$)$_{1-6}$—NH—C(O)—, and —O—C(O)—NH—($CH_2$)$_{1-6}$—NH—C(O)—, wherein the subscript values following each methylene indicate the number of methylenes contained in the structure, e.g., ($CH_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —($CH_2CH_2O$)$_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

As indicated above, in some instances the water-soluble polymer-(GLP-1) conjugate will include a non-linear water-soluble polymer. Such a non-linear water-soluble polymer encompasses a branched water-soluble polymer (although other non linear water-soluble polymers are also contemplated). Thus, in one or more embodiments of the invention, the conjugate comprises a GLP-1 moiety comprising an internal or N-terminal amine covalently attached, either directly or through a spacer moiety comprised of one or more atoms, to a branched water-soluble polymer. As used herein, an internal amine is an amine that is not part of the N-terminal amino acid (meaning not only the N-terminal amine, but any amine on the side chain of the N-terminal amino acid).

Although such conjugates include a branched water-soluble polymer attached (either directly or through a spacer moiety) to a GLP-1 moiety at an internal amino acid of the GLP-1 moiety, additional branched water-soluble polymers can also be attached to the same GLP-1 moiety at other locations' as well. Thus, for example, a conjugate including a branched water-soluble polymer attached (either directly or through a spacer moiety) to a GLP-1 moiety at an internal amino acid of the GLP-1 moiety, can further include an additional branched water-soluble polymer covalently attached, either directly or through a spacer moiety comprised of one or more atoms, to the N-terminal amino acid residue, such as at the N-terminal amine.

As stated above, in some instances, the branched water-soluble polymer may lack a lysine residue in which the polymeric portions are connected to amine groups of the lysine via a "—OCH$_2$CONHCH$_2$CO—" group. In still other instances, the branched water-soluble polymer lacks a lysine residue (wherein the lysine residue is used to effect branching).

One preferred branched water-soluble polymer comprises the following structure:

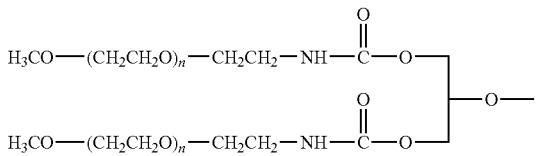

wherein each (n) is independently an integer having a value of from 3 to 4000, or more preferably, from about 10 to 1800.

Also forming part of the invention are multi-armed polymer conjugates comprising a polymer scaffold having 3 or more polymer arms each suitable for capable of covalent attachment of a GLP-1 moiety.

Exemplary conjugates in accordance with this embodiment of the invention will generally comprise the following structure:

R—(POLY-L$_D$-GLP-1)$_y$ wherein R is a core molecule as previously described, POLY is a water-soluble polymer, $L_D$ is a degradable, e.g., hydrolyzable linkage, and y ranges from about 3 to 15.

More particularly, such a conjugate may comprise the structure:

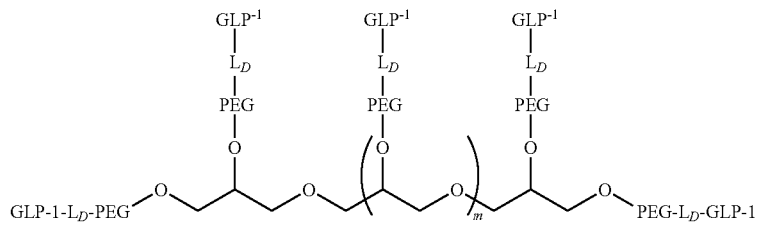

where m is selected from 3, 4, 5, 6, 7, and 8.

In yet a related embodiment, the GLP-1 conjugate may correspond to the structure:

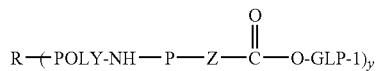

where R is a core molecule as previously described, P is a spacer, Z is —O—, —NH—, or —CH$_2$—, —O-GLP-1 is a hydroxyl residue of a GLP-1 moiety, and y is 3 to 15. Preferably, —NH—P-Z-C(O)— is a residue of a naturally or non-naturally occurring amino acid.

Additional exemplary conjugates in accordance with the invention are provided in Examples 4-26 herein.

Purification

The GLP-1 polymer conjugates described herein can be purified to obtain/isolate different conjugate species. Specifically, a product mixture can be purified to obtain an average of anywhere from one, two, or three or even more PEGs per GLP-1 moiety. In one embodiment of the invention, preferred GLP-1 conjugates are mono-conjugates. The strategy for purification of the final conjugate reaction mixture will depend upon a number of factors, including, for example, the molecular weight of the polymeric reagent employed, the GLP-1 moiety, and the desired characteristics of the product—e.g., monomer, dimer, particular positional isomers, etc.

If desired, conjugates having different molecular weights can be isolated using gel filtration chromatography and/or ion exchange chromatography. Gel filtration chromatography may be used to fractionate different GLP-1 conjugates (e.g., 1-mer, 2-mer, 3-mer, and so forth, wherein "1-mer" indicates one polymer molecule per GLP-1, "2-mer" indicates two polymers attached to GLP-1, and so on) on the basis of their differing molecular weights (where the difference corresponds essentially to the average molecular weight of the water-soluble polymer. While this approach can be used to separate PEG and other GLP-1 polymer conjugates having different molecular weights, this approach is generally ineffective for separating positional isomers having different polymer attachment sites within the GLP-1 moiety. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) or other functional groups of the GLP-1 moiety.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) Anal. Biochem, 107:60-63), and (iv) sodium dodecyl sulfate polyacrylamide gel electrophoresis (SDS PAGE), followed by staining with barium iodide.

Separation of positional isomers is typically carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-GLP-1 isomers having the same molecular weight (positional isomers).

The resulting purified compositions are preferably substantially free of the non-conjugated GLP-1 moiety. In addition, the compositions preferably are substantially free of all other non-covalently attached water-soluble polymers.

Compositions

Compositions of Conjugate Isomers

Also provided herein are compositions comprising any one or more of the GLP-1 polymer conjugates described herein. In certain instances, the composition will comprise a plurality of GLP-1 polymer conjugates. For instance, such a composition may comprise a mixture of GLP-1 polymer conjugates having one, two, three and/or even four water-soluble polymer molecules covalently attached to sites on the GLP-1 moiety. That is to say, a composition of the invention may comprise a mixture of monomer, dimer, and possibly even trimer or 4-mer. Alternatively, the composition may possess only mono-conjugates, or only di-conjugates, etc. A mono-conjugate GLP-1 composition will typically comprise GLP-1 moieties having only a single polymer covalently attached thereto, e.g., preferably releasably attached. A mono-conjugate composition may comprise only a single positional isomer, or may comprise a mixture of different positional isomers having polymer covalently attached to different sites within the GLP-1 moiety. For example, a mono-conjugate GLP-1 composition may contain a mixture of mono-conjugated GLP-1 species having water-soluble polymer attached to either lysine-26 or lysine-34. Alternately, a mono-conjugate composition may possess the water-soluble polymer attached to only lysine 26, or only lysine-34, or only the N-terminus.

In yet another embodiment, a GLP-1 conjugate may possess multiple GLP-1 moieties covalently attached to a single multi-armed polymer having 3 or more polymer arms. Typically, the GLP-1 moieties are each attached at the same GLP-1 amino acid site, e.g., the N-terminus.

With respect to the conjugates in the composition, the composition will typically satisfy one or more of the following characteristics: at least about 85% of the conjugates in the composition will have from one to four polymers attached to the GLP-1 moiety; at least about 85% of the conjugates in the composition will have from one to three polymers attached to the GLP-1 moiety; at least about 85% of the conjugates in the composition will have from one to two polymers attached to the GLP-1 moiety; or at least about 85% of the conjugates in the composition will have one polymer attached to the GLP-1 moiety (i.e., be monoPEGylated); at least about 95% of the conjugates in the composition will have from one to four polymers attached to the GLP-1 moiety; at least about 95% of the conjugates in the composition will have from one to three polymers attached to the GLP-1 moiety; at least about 95% of the conjugates in the composition will have from one to two polymers attached to the GLP-1 moiety; at least about 95% of the conjugates in the composition will have one polymers attached to the GLP-1 moiety; at least about 99% of the conjugates in the composition will have from one to four polymers attached to the GLP-1 moiety; at least about 99% of the conjugates in the composition will have from one to three polymers attached to the GLP-1 moiety; at least about 99% of the conjugates in the composition will have from one to two polymers attached to the GLP-1 moiety; and at least about 99% of the conjugates in the composition will have one polymer attached to the GLP-1 moiety (i.e., be monoPEGylated).

In one or more embodiments, the conjugate-containing composition is free or substantially free of albumin.

In one or more embodiments of the invention, a pharmaceutical composition is provided comprising a conjugate comprising a GLP-1 moiety covalently attached, e.g., releasably, to a water-soluble polymer, wherein the water-soluble polymer has a weight-average molecular weight of greater than about 2,000 Daltons; and a pharmaceutically acceptable excipient.

Control of the desired number of polymers for covalent attachment to GLP-1 is achieved by selecting the proper polymeric reagent, the ratio of polymeric reagent to the GLP-1 moiety, temperature, pH conditions, and other aspects of the conjugation reaction. In addition, reduction or elimination of the undesired conjugates (e.g., those conjugates having four or more attached polymers) can be achieved through purification mean as previously described.

For example, the water-soluble polymer-(GLP-1) moiety conjugates can be purified to obtain/isolate different conjugated species. Specifically, the product mixture can be purified to obtain an average of anywhere from one, two, three, or four PEGs per GLP-1 moiety, typically one, two or three PEGs per GLP-1 moiety. In one or more embodiments, the product mixture contains one PEG per GLP-1, where PEG is releasably (via hydrolysis) attached to PEG polymer, e.g., a branched or straight chain PEG polymer.

Pharmaceutical Compositions

Optionally, a GLP-1 conjugate composition of the invention will comprise, in addition to the GLP-1 conjugate, a pharmaceutically acceptable excipient. More specifically, the composition may further comprise excipients, solvents, stabilizers, membrane penetration enhancers, etc., depending upon the particular mode of administration and dosage form.

Pharmaceutical compositions of the invention encompass all types of formulations and in particular those that are suited for injection, e.g., powders or lyophilates that can be reconstituted as well as liquids, as well as for inhalation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Compositions suitable for pulmonary administration will be described in greater detail below.

Exemplary pharmaceutically acceptable excipients include, without limitation, carbohydrates, inorganic salts, antimicrobial agents, antioxidants, surfactants, buffers, acids, bases, and combinations thereof.

Representative carbohydrates for use in the compositions of the present invention include sugars, derivatized sugars such as alditols, aldonic acids, esterified sugars, and sugar polymers. Exemplary carbohydrate excipients suitable for use in the present invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like. Preferred, in particular for formulations intended for inhalation, are non-reducing sugars, sugars that can form a substantially dry amorphous or glassy phase when combined with the composition of the present invention, and sugars possessing relatively high glass transition temperatures, or Tgs (e.g., Tgs greater than 40° C., or greater than 50° C., or greater than 60° C., or greater than 70° C., or having Tgs of 80° C. and above). Such excipients may be considered glass-forming excipients.

Additional excipients include amino acids, peptides and particularly oligomers comprising 2-9 amino acids, or 2-5 mers, and polypeptides, all of which may be homo or hetero species. Representative amino acids include glycine (gly), alanine (ala), valine (val), leucine (leu), isoleucine (ile), methionine (met), proline (pro), phenylalanine (phe), tryptophan (trp), serine (ser), threonine (thr), cysteine (cys), tyrosine (tyr), asparagine (asp), glutamic acid (glu), lysine (lys), arginine (arg), histidine (his), norleucine (nor), and modified forms thereof.

Also useful as excipients, e.g., in inhalable compositions, are di- and tripeptides containing two or more leucyl residues, as described in Nektar Therapeutics' International patent application WO 01/32144, incorporated herein by reference in its entirety.

Also preferred are di- and tripeptides having a glass transition temperature greater than about 40° C., or greater than 50° C., or greater than 60° C., or greater than 70° C.

Although less preferred due to their limited solubility in water, additional stability and aerosol performance-enhancing peptides for use in compositions for pulmonary administration include 4-mers and 5-mers containing any combination of amino acids as described above. The 4-mer or 5-mer may comprise two or more leucine residues. The leucine residues may occupy any position within the peptide, while the remaining (i.e., non-leucyl)amino acids positions are occupied by any amino acid as described above, provided that the resulting 4-mer or 5-mer has a solubility in water of at least about 1 mg/ml. In some embodiments, the non-leucyl amino acids in a 4-mer or 5-mer are hydrophilic amino acids such as lysine, to thereby increase the solubility of the peptide in water.

Exemplary protein excipients include albumins such as human serum albumin (HSA), recombinant human albumin (rHA), gelatin, casein, hemoglobin, and the like. The compositions may also include a buffer or a pH-adjusting agent, typically but not necessarily a salt prepared from an organic acid or base. Representative buffers include organic acid salts of citric acid, ascorbic acid, gluconic acid, carbonic acid, tartaric acid, succinic acid, acetic acid, or phthalic acid. Other suitable buffers include Tris, tromethamine hydrochloride, borate, glycerol phosphate, and phosphate. Amino acids such as glycine are also suitable.

The compositions of the present invention may also include one or more additional polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin.

The compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80," and pluronics such as F68 and F88, available from BASF), sorbitan esters, lipids (e.g., phospholipids such as lecithin and other phosphatidylcholines, phosphatidylethanolamines, although preferably not in liposomal form), fatty acids and fatty esters, steroids (e.g., cholesterol), and chelating agents (e.g., zinc and other such suitable cations). The use of certain di-substituted phosphatidylcholines for producing perforated microstructures (i.e., hollow, porous microspheres) may also be employed.

Other pharmaceutical excipients and/or additives suitable for use in the compositions according to the present invention are listed in "Remington: The Science & Practice of Pharmacy," 21$^{st}$ ed., Williams & Williams, (2005), and in the "Physician's Desk Reference," 60th ed., Medical Economics, Montvale, N.J. (2006).

The amount of the GLP-1 conjugate (i.e., the conjugate formed between the active agent and the polymeric reagent) in the composition will vary depending on a number of factors, but will optimally be a therapeutically effective amount when the composition is stored in a unit dose container (e.g., a vial). In addition, a pharmaceutical preparation, if in solution form, can be housed in a syringe. A therapeutically effective amount can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient or excipients will be present in the composition in an amount of about 1% to about 99% by weight, from about 5% to about 98% by weight, from about 15 to about 95% by weight of the excipient, or with concentrations less than 30% by weight. In general, a high concentration of the GLP-1 moiety is desired in the final pharmaceutical formulation.

Combination of Actives

A composition of the invention may also comprise a mixture of water-soluble polymer-(GLP-1) moiety conjugates and unconjugated GLP-1, to thereby provide a mixture of fast-acting and long-acting GLP-1. Alternatively, the composition may also comprise, in addition to a GLP-1 water-soluble polymer conjugate, insulin, e.g., a basal insulin such as an acylated basal insulin or a pI-shifted basal insulin. Generally, a basal insulin is one exhibiting a prolonged time of action of greater than about 8 hours in a standard model of diabetes. Exemplary basal insulins include NPH, NPL, PZI, Ultralente, and insulin glargine.

Additional pharmaceutical compositions in accordance with the invention include those comprising, in addition to an extended-action GLP-1 water-soluble polymer conjugate as described herein, a rapid acting GLP-1 polymer conjugate where the water-soluble polymer is releasably attached to the side-chain of the terminal histidine (His7) at the imidazole nitrogen.

Compositions for Pulmonary Administration

Compositions comprising a GLP-1 polymer conjugate include those suitable for pulmonary administration. The preparation and features of such inhalable compositions will now be described.

One embodiment of the present invention provides dry powder compositions suitable for pulmonary delivery. Dry powder compositions of the present invention may be prepared by any of a number of drying techniques, including by spray drying. Spray drying of the compositions is carried out, for example, as described generally in the "Spray Drying Handbook," 5$^{th}$ ed., K. Masters, John Wiley & Sons, Inc., NY, N.Y. (1991), and in Platz, R., et al., International Patent Publication Nos. WO 97/41833 (1997) and WO 96/32149 (1996).

A suspension or solution comprising a GLP-1 conjugate of the present invention can be spray-dried in a conventional spray drier, such as those available from commercial suppliers such as Niro A/S (Denmark), Buchi (Switzerland) and the like, resulting in a dispersible, dry powder. Desirable conditions for spray drying will vary depending upon the composition components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause degradation of the pharmaceutical protein in the sprayed material. Such temperatures are typically determined experimentally, although in general the inlet temperature will range from about 50° C. to about 200° C., while the outlet temperature will range from about 30° C. to about 150° C. Parameters may include atomization pressures ranging from about 20-150 psi, or from about 30-100 psi. Typically the atomization pressure employed will be one of the following (psi): 20, 30, 40, 50, 60, 70, 80, 90, 100, 110, or 120 or above.

Respirable compositions of the present invention having the features described herein may also be produced by drying certain composition components, which result in formation of a perforated microstructure powder as described in WO 99/16419. The perforated microstructure powders typically comprise spray-dried, hollow microspheres having a relatively thin porous wall defining a large internal void. The perforated microstructure powders may be dispersed in a selected suspension media (such as a non-aqueous and/or fluorinated blowing agent) to provide stabilized dispersions prior to drying. The use of relatively low density perforated (or porous) microstructures or microparticulates significantly reduces attractive forces between the particles, thereby lowering the shear forces, increasing the flowability and dispersibility of the resulting powders, and reducing the degradation by flocculation, sedimentation or creaming of the stabilized dispersions thereof.

Alternatively, powders may be prepared by lyophilization, vacuum drying, spray freeze drying, super critical fluid processing (e.g., as described in Hanna, et al., U.S. Pat. No. 6,063,138), air drying, or other forms of evaporative drying.

Dry powders may also be prepared by blending, grinding, sieving, or jet milling composition components in dry powder form.

Once formed, the dry powder compositions are preferably maintained under dry (i.e., relatively low humidity) conditions during manufacture, processing, and storage. Irrespective of the drying process employed, the process will preferably result in inhalable, highly dispersible particles comprising the GLP-1 conjugates of the present invention.

In one or more embodiments, powders of the present invention may be characterized by several features, most notably, (i) consistently high dispersibilities, which are maintained, even upon storage, (ii) small aerodynamic particles sizes (MMADs), (iii) improved fine particle dose values, i.e., powders having particles sized less than 10 microns, all of which contribute to the improved ability of the powder to penetrate to the tissues of the lower respiratory tract (i.e., the alveoli) for delivery to the systemic circulation. These physical characteristics of the inhalable powders of the present invention, to be described more fully below, play a role in maximizing the efficiency of aerosolized delivery of such powders to the deep lung.

The particles of the present invention may generally have a mass median diameter (MMD), or volume median geometric diameter (VMGD), or mass median envelope diameter (MMED), or a mass median geometric diameter (MMGD), of less than about 20 μm, or less than about 10 μm, or less than about 7.5 μm, or less than about 4 μm, or less than about 3.3 μm, and usually are in the range of 0.1 μm to 5 μm in diameter. Preferred powders are composed of particles having an MMD, VMGD, MMED, or MMGD from about 1 to 5 μm. In some cases, the powder will also contain non-respirable carrier particles such as lactose, where the non-respirable particles are typically greater than about 40 microns in size.

The powders of the present invention may also be characterized by an aerosol particle size distribution—mass median aerodynamic diameter (MMAD)—typically having MMADs less than about 10 μm, such as less than 5 μm, less than 4.0 μm, less than 3.3 μm, or less than 3 μm. The mass median aerodynamic diameters of the powders will typically range from about 0.1-5.0 μm, or from about 0.2-5.0 μm MMAD, or from about 1.0-4.0 μM MMAD, or from about 1.5 to 3.0 μm. Small aerodynamic diameters may be achieved by a combination of optimized spray drying conditions and choice and concentration of excipients.

The powders of the present invention may also be characterized by their densities. The powder will generally possess a bulk density from about 0.1 to 10 g/cubic centimeter, or from about 0.1-2 g/cubic centimeter, or from about 0.15-1.5 g/cubic centimeter. In one embodiment of the present invention, the powders have big and fluffy particles with a density of less than about 0.4 g/cubic centimeter and an MMD between 5 and 30 microns. It is worth noting that the relationship of diameter, density and aerodynamic diameter can be determined by the following formula (Gonda, "Physicochemical principles in aerosol delivery," in Topics in Pharmaceutical Sciences 1991, Crommelin, D. J. and K. K. Midha, Eds., Medpharm Scientific Publishers, Stuttgart, pp. 95-117, 1992).

The powders may have a moisture content below about 20% by weight, usually below about 10% by weight, or below about 5% by weight. Such low moisture-containing solids tend to exhibit a greater stability upon packaging and storage.

Additionally, the spray drying methods and stabilizers described herein are generally effective to provide highly dispersible compositions. Generally, the emitted dose (ED) of these powders is greater than 30%, and usually greater than 40%. In some embodiments, the ED of the powders of the present invention is greater than 50%, 60%, 70%, or higher.

A particular characteristic which usually relates to improved dispersibility and handling characteristics is the product rugosity. Rugosity is the ratio of the specific area (e.g., as measured by BET, molecular surface adsorption, or other conventional technique) and the surface area calculated from the particle size distribution (e.g., as measured by centrifugal sedimentary particle size analyzer, Horiba Capa 700) and particle density (e.g., as measured by pycnometry), assuming non-porous spherical particles. Rugosity may also be measured by air permeametry. If the particles are known to be generally nodular in shape, as is the case in spray drying, rugosity is a measure of the degree of convolution or folding of the surface. This may be verified for powders made by the present invention by SEM analysis. A rugosity of 1 indicates that the particle surface is spherical and non-porous. Rugosity values greater than 1 indicate that the particle surface is non-uniform and convoluted to at least some extent, with higher numbers indicating a higher degree of non-uniformity. The powders of the present invention typically have a rugosity of at least about 2, such as at least about 3, at least about 4, or at least about 5, and may range from 2 to 10, such as from 4 to 8, or from 4 to 6.

In some embodiments of the invention, powder surface area, measured by nitrogen adsorption, typically ranges from about 6 $m^2/g$ to about 13 $m^2/g$, such as from about 7 $m^2/g$ to about 10 $m^2/g$. The particles often have a convoluted "raisin" structure rather than a smooth spherical surface.

A particularly preferred embodiment of the present invention is one where at least the outermost regions, including the outer surface, of the powder particles are in an amorphous glassy state. It is thought that when the particles have a high $T_g$ material at their surfaces, the powder will be able to take up considerable amounts of moisture before lowering the $T_g$ to the point of instability ($T_g$-$T_s$ of less than about 10° C.).

The compositions described herein typically possess good stability with respect to both chemical stability and physical stability, i.e., aerosol performance over time. Generally, with respect to chemical stability, the GLP-1 conjugate contained in the composition will degrade by no more than about 10% upon spray drying. That is to say, the powder will generally possess at least about 90%, or about 95%, or at least about 97% or greater of the intact pharmaceutical protein.

With respect to aerosol performance, compositions of the present invention are generally characterized by a drop in emitted dose of no more than about 20%, or no more than about 15%, or no more than about 10%, when stored under ambient conditions for a period of three months.

Alternatively, the GLP-1 polymer conjugates of the present invention can be formulated into perforated microstructures. Such microstructures, and methods of their manufacture, are described in U.S. Pat. No. 6,565,885.

Briefly, such perforated microstructures generally comprise a structural matrix that exhibits, defines, or comprises voids, pores, defects, hollows, spaces, interstitial spaces, apertures, perforations, or holes. The absolute shape (as opposed to the morphology) of the perforated microstructure is generally not critical and any overall configuration that provides the desired characteristics is contemplated as being within the scope of the invention. Accordingly, some embodiments comprise approximately microspherical shapes.

Administration

The GLP-1 conjugates of the invention can be administered by any of a number of routes including without limitation, oral, rectal, nasal, topical (including transdermal, aerosol, buccal and sublingual), vaginal, parenteral (including subcutaneous, intramuscular, intravenous and intradermal), intrathecal, and pulmonary. Preferred forms of administration include parenteral and pulmonary. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

In-vivo data provided in Example 8 demonstrates the blood glucose lowering effect of an exemplary releasable GLP-1 conjugate of the invention, as well as its ability to provide such an effect over an extended period of time, i.e., for more than 48 hours, when administered by injection. In contrast, native GLP-1 underwent rapid clearance. See, for example, FIGS. 13 and 14.

In some preferred embodiments of the invention, the GLP-1 polymer conjugate compositions are administered pulmonarily, preferably by inhalation. In vivo data in support of this aspect of the invention are provided in Examples 25 and 26, in which certain exemplary releasable GLP-1 conjugates were administered by intratracheal administration. Both sets of data indicate that pulmonary administration of a releasable GLP-1 polymer conjugate is effective to result in suppression of blood glucose levels over a period of time substantially extended over that observed for unconjugated GLP-1.

The dry powder compositions as described herein may be delivered pulmonarily using any suitable dry powder inhaler (DPI), i.e., an inhaler device that utilizes the patient's inhaled breath as a vehicle to transport the dry powder drug to the lungs. Included are Nektar Therapeutics' dry powder inhalation devices as described in Patton, J. S., et al., U.S. Pat. No. 5,458,135, Oct. 17, 1995; Smith, A. E., et al., U.S. Pat. No. 5,740,794, Apr. 21, 1998; and in Smith, A. E., et al., U.S. Pat. No. 5,785,049, Jul. 28, 1998, incorporated herein by reference. When administered using a device of this type, the powdered medicament is contained in a receptacle having a puncturable lid or other access surface, preferably a blister package or cartridge, where the receptacle may contain a single dosage unit or multiple dosage units. Convenient methods for filling large numbers of cavities (i.e., unit dose packages) with metered doses of dry powder medicament are described, e.g., in Parks, D. J., et al., International Patent Publication WO 97/41031, Nov. 6, 1997, incorporated herein by reference.

Other dry powder dispersion devices for pulmonary administration of dry powders include those described, for example, in Newell, R. E., et al, European Patent No. EP 129985, Sep. 7, 1988); in Hodson, P. D., et al., European Patent No. EP472598, Jul. 3, 1996; in Cocozza, S., et al., European Patent No. EP 467172, Apr. 6, 1994, and in Lloyd, L. J. et al., U.S. Pat. No. 5,522,385, Jun. 4, 1996, incorporated herein by reference. Also suitable for delivering the dry powders of the present invention are inhalation devices such as the Astra-Draco "TURBUHALER." This type of device is described in detail in Virtanen, R., U.S. Pat. No. 4,668,218, May 26, 1987; in Wetterlin, K., et al., U.S. Pat. No. 4,667,668, May 26, 1987; and in Wetterlin, K., et al., U.S. Pat. No. 4,805,811, Feb. 21, 1989, all of which are incorporated herein by reference. Other suitable devices include dry powder inhalers such as Rotahaler™ (Glaxo), Discus™ (Glaxo), Spiros™ inhaler (Dura Pharmaceuticals), and the Spinhaler™ (Fisons). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in Mulhauser, P., et al, U.S. Pat. No. 5,388,572, Sep. 30, 1997, incorporated herein by reference.

The compositions of the present invention may also be delivered using a pressurized, metered dose inhaler (MDI), e.g., the Ventolin™ metered dose inhaler, containing a solution or suspension of drug in a pharmaceutically inert liquid propellant, e.g., a chlorofluorocarbon or fluorocarbon, as described in Laube, et al., U.S. Pat. No. 5,320,094, and in Rubsamen, R. M., et al, U.S. Pat. No. 5,672,581.

Alternatively, the compositions described herein may be dissolved or suspended in a solvent, e.g., water or saline, and administered by nebulization. Nebulizers for delivering an aerosolized solution include the AERx™ (Aradigm), the Ultravent™ (Mallinkrodt), the Pari LC Plus™ or the Pari LC Star™ (Pari GmbH, Germany), the DeVilbiss Pulmo-Aide, and the Acorn II™ (Marquest Medical Products).

In one or more embodiments of the invention, a method is provided, the method comprising delivering a conjugate to a patient, the method comprising the step of administering to the patient a pharmaceutical composition comprising a GLP-1 polymer conjugate as provided herein. Administration can be effected by any of the routes herein described. The method may be used to treat a patient suffering from a condition that is responsive to treatment with GLP-1 by administering a therapeutically effective amount of the pharmaceutical composition.

As previously stated, the method of delivering a GLP-1 polymer conjugate as provided herein may be used to treat a patient having a condition that can be remedied or prevented by administration of GLP-1. Subjects in need of treatment with GLP-1 or a GLP-1 conjugate of the invention include those with non-insulin dependent diabetes, insulin dependent diabetes, stroke, myocardial infarction, obesity, catabolic changes after surgery, functional dyspepsia, and irritable bowel syndrome. Also included are subjects requiring prophylactic treatment, e.g., subjects at risk for developing non-insulin dependent diabetes. Additional subjects include those with impaired glucose tolerance or impaired fasting glucose.

Certain conjugates of the invention, e.g., releasable conjugates, include those effective to release the GLP-1 moiety, e.g., by hydrolysis, over a period of several hours or even days (e.g., 2-7 days, 2-6 days, 3-6 days, 3-4 days) when evaluated in a suitable in-vivo model. Releasable conjugates of the invention include those effective to lower blood glucose levels over an extended period of time, e.g., for at least about 8 hours, for at least about 10 hours, for about 1-3 days or so, or for about 1-2.5 days.

In view of the above, the blood glucose of the patient may reach a minimum at a time ranging from about 2 hours to about 30 hours, such as about 4 hours to about 24 hours, 6 hours to about 18 hours, or about 8 hours to about 12 hours, after administration. In the case of pulmonary administration, the blood glucose of the patient may reach a minimum at a time ranging from about 2 hours to about 12 hours, such as about 4 hours to about 10 hours or about 6 hours to about 8 hours. In the case of subcutaneous administration, the blood glucose of the patient reaches a minimum at a time ranging from about 2 hours to about 30 hours, such as about 4 hours to about 24 hours, 6 hours to about 18 hours, or about 8 hours to about 12 hours.

The blood glucose of the patient may reach a minimum that ranges from about 25% to about 60%, such as about 30% to about 55%, 35% to about 50%, or about 40% to about 45%, of blood glucose before administration, e.g., by subcutaneous or pulmonary administration. As an example, the patient may have a blood glucose level of less than about 126 mg/dl, such as less than about 120 mg/dl, less than about 110 mg/dl, or less than 100 mg/dl, after administration, e.g., by subcutaneous or pulmonary administration.

The patient may have reduced blood glucose up to about 160 hours, such as up to about 140 hours, up to about 120 hours, up to about 100 hours, up to about 80 hours, up to about 60 hours, up to about 40 hours, up to about 24 hours, or up to about 12 hours, after administration. In the case of pulmonary administration, the patient may have reduced blood glucose up to about 60 hours, up to about 50 hours, up to about 40 hours, up to about 30 hours, up to about 24 hours, or up to about 12 hours.

The actual dose of the GLP-1 conjugate to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a conjugate of the invention will be delivered such that plasma levels of a GLP-1 moiety are within a range of about 5 picomoles/liter to about 200 picomoles/liter.

On a weight basis, a therapeutically effective dosage amount of a GLP-1 conjugate as described herein will range from about 0.01 mg per day to about 1000 mg per day for an adult. For example, dosages may range from about 0.1 mg per day to about 100 mg per day, or from about 1.0 mg per day to about 10 mg/day. On an activity basis, corresponding doses based on international units of activity can be calculated by one of ordinary skill in the art.

The unit dosage of any given conjugate (again, such as provided as part of a pharmaceutical composition) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis and the like, which are within the skill of the art. Such techniques are fully explained in the literature. Reagents and materials are commercially available unless specifically stated to the contrary. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

Although other abbreviations known by one having ordinary skill in the art will be referenced, other reagents and materials will be used, and other methods known by one having ordinary skill in the art will be used, the following list and methods description is provided for the sake of convenience.

Abbreviations mPEG-SPA mPEG-succinimidyl propionate mPEG-SBA mPEG-succinimidyl butanoate mPEG-OPSS mPEG-orthopyridyl-disulfide mPEG-MAL mPEG-maleimide, $CH_3O-(CH_2CH_2O)_n-CH_2CH_2-MAL$ mPEG-SMB mPEG-succinimidyl α-methylbutanoate, $CH_3O-(CH_2CH_2O)_n-CH_2CH_2-CH(CH_3)-C(O)-O$-succinimide mPEG-ButyrALD $H_3O-(CH_2CH_2O)_n-CH_2CH_2-O-C(O)-NH-(CH_2CH_2O)_4-CH_2CH_2CH_2C(O)H$ mPEG-PIP $CH_3O-(CH_2CH_2O),-CH_2CH_2-C(O)$-piperidin-4-one mPEG-CM $CH_3O-(CH_2CH_2O),-CH_2CH_2-O-CH_2-C(O)-OH)$ anh. Anhydrous CV column volume Fmoc 9-fluorenylmethoxycarbonyl $NaCNBH_3$ sodium cyanoborohydride HCl hydrochloric acid HEPES 4-(2-hydroxyethyl)-1-piperazineethanesulfonic acid NMR nuclear magnetic resonance DCC 1,3-dicyclohexylcarbodiimide DMF dimethylformamide DMSO dimethyl sulfoxide DI deionized MW molecular weight K or kDa kilodaltons SEC Size exclusion chromatography HPLC high performance liquid chromatography FPLC fast protein liquid chromatography SDS-PAGE sodium dodecyl sulfate-polyacrylamide gel electrophoresis MALDI-TOF Matrix Assisted Laser Desorption Ionization Time-of-Flight TLC Thin Layer Chromatography THF Tetrahydrofuran MATERIALS: All PEG reagents referred to in the appended examples are commercially available unless otherwise indicated. Glucagon-like Peptide-1 (GLP-1(7-36)$NH_2$), "GLP-1") used in these Examples was purchased from American Peptide Company (Sunnyvale, Calif.).

Example 1
Preparation of N-{di(mPEG(20,000)oxymethylcarbonylamino)fluoren-9-ylmethoxycarbonyloxy}succinimide for Reversible PEGylation of GLP-1
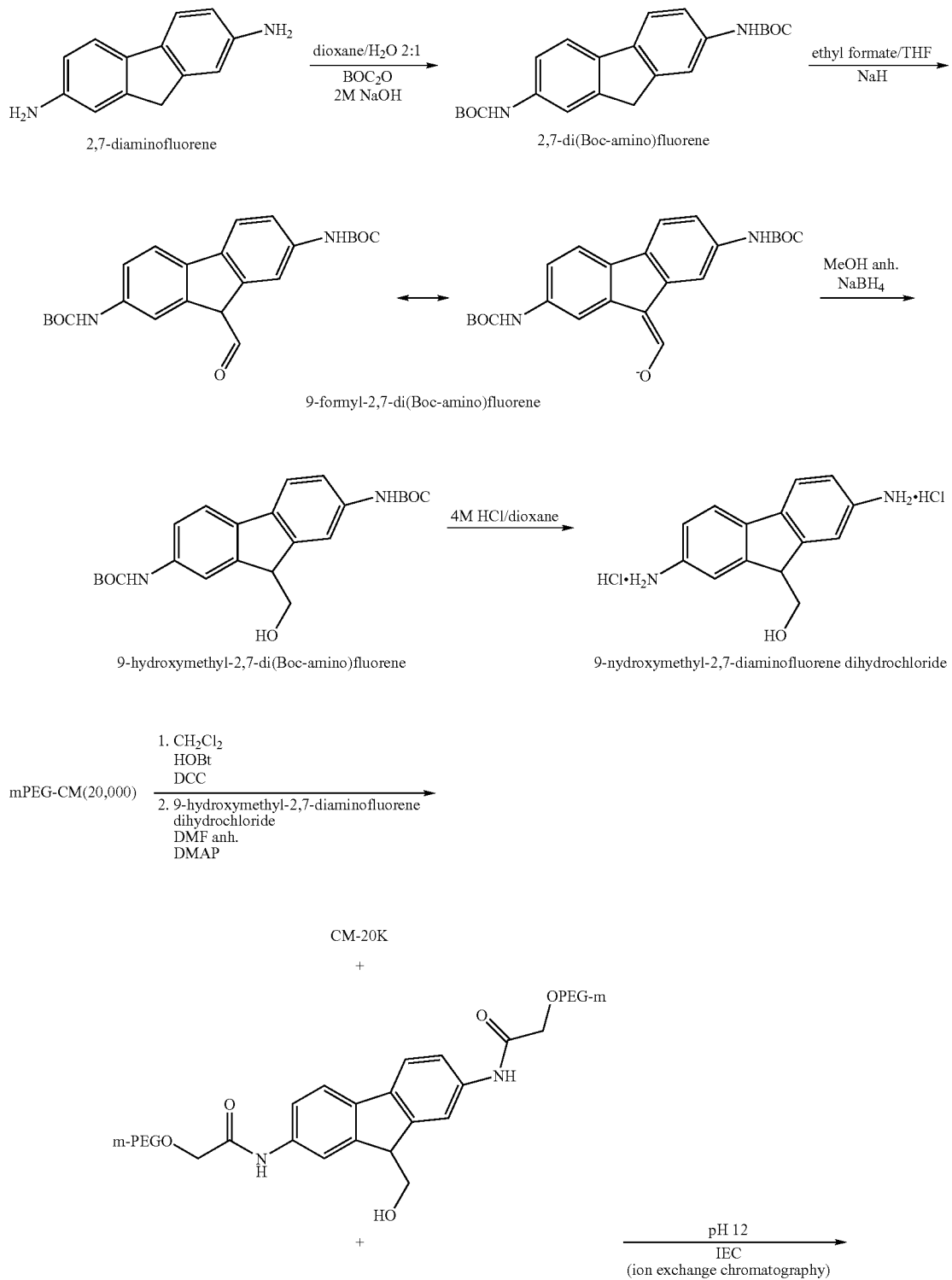

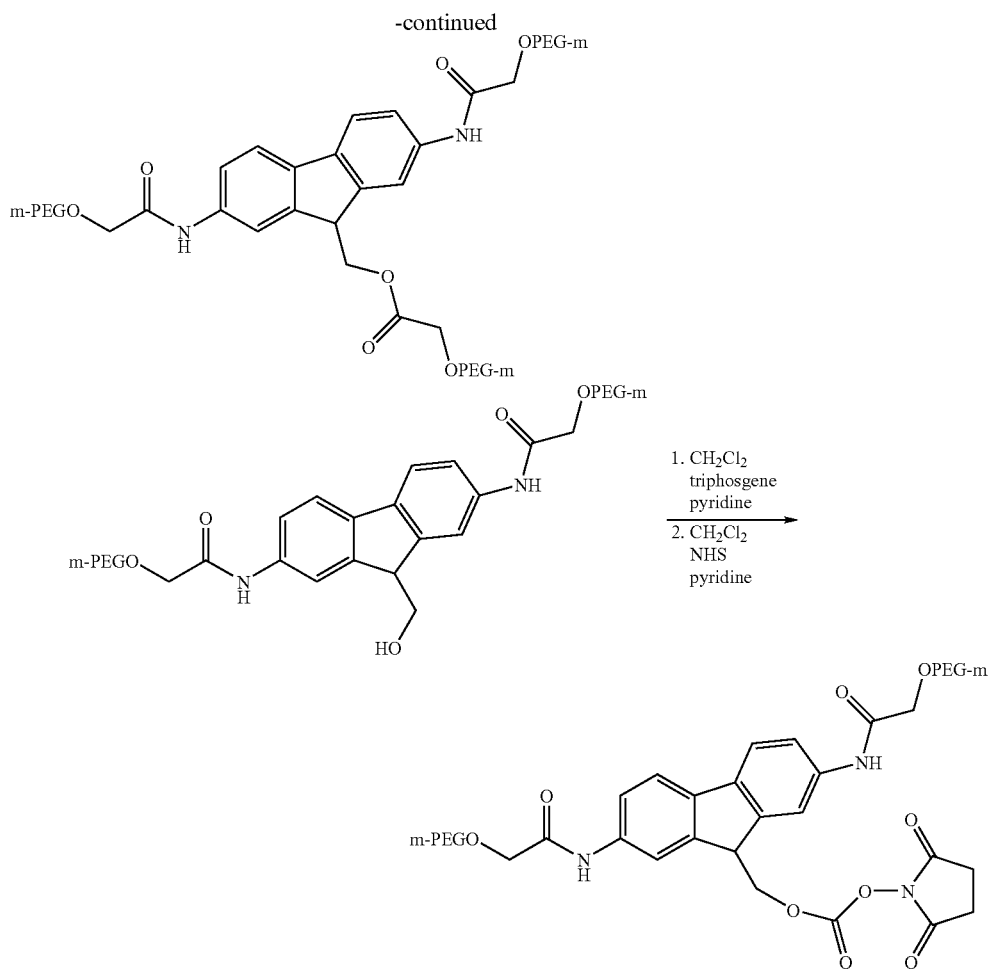

A. Preparation of 2,7-di(Boc-amino)fluorene

Under an argon atmosphere, 2,7-diaminofluorene (2.45 g, 12.5 mmol) was dissolved in 1,4-dioxane (28 mL). Deionized water (14 mL), NaOH 2M (2.2 eq, 27.5 mmol, 13.8 mL) and di-tert-butyldicarbonate (BOC$_2$O) (2.5 eq, 31.3 mmol, 6.82 g) were added successively. The reaction was stirred vigorously for 20 hours at room temperature. Product precipitated as a brown solid. The reaction was quenched by the addition of water and acidification to pH 3 with KHSO$_4$ 1M. Product was extracted with chloroform (3×400 mL) and the combined organic layers were washed with ½ saturated brine, dried over Na$_2$SO$_4$ and evaporated. Product was purified by flash chromatography: silica gel 60 Å eluted with 1% methanol in chloroform. The purified yellow solid (5.1 g, ~99%) was pure by TLC (ninhydrin stain). $^1$H-NMR (CDCl$_3$): δ (ppm) 7.7 (bs, 2H, NH urethane); 7.6 (d, 2H, Ar); 7.2 (d, 2H, Ar); 6.5 (s, 2H, Ar); 3.8 (s, 2H, CH$_2$); 1.5 (s, 18H, Boc).

B. Preparation of 9-formyl-2,7-di(Boc-amino)fluorene

Purified 2,7-di(Boc-amino)fluorene (5 g, 12.5 mmol) (prepared from step A, above), was dissolved in ethyl formate (50 mL) and anhydrous THF (60 mL) with gentle heating. (Note: ethyl formate was stored over K$_2$CO$_3$ to remove formic acid.) The solution was cooled in an ice bath and sodium hydride 60% in mineral oil was added portion-wise (5.5 eq, 69 mmol, 2.75 g). The reaction was slowly warmed to room temperature and then heated to 50° C. after fitting with a reflux condenser. After two hours, the reaction was cooled in an ice bath and quenched by the slow addition of deionized water (50 mL). The aqueous layer was adjusted to pH 5 with glacial acetic acid and extracted with ethyl acetate (2×400 mL). The combined organic layers were dried with Na$_2$SO$_4$, filtered and evaporated under reduced pressure. The crude product (dark brown solid) was purified by flash chromatography: silica gel 60 Å step-wise gradient elution 1-5% methanol in chloroform. Yield (4.8 g, ~90%) of a yellow to brown solid, depending on purity. $^1$H-NMR (d$_6$-DMSO): δ (ppm) 11.0 (s, 0.9H, enol); 9.3 (2 s, 1.9H, NH urethane); 7.2-8.3 (m, Ar, C$^{10}$ H enol); 6.5 (2 s, 0.1H, NH urethane); 4.1 (m, 0.3H, CH); 1.5 (s, 18H, Boc).

C. Preparation of 9-hydroxymethyl-2,7-di(Boc-amino)fluorene

9-Formyl-2,7-di(Boc-amino)fluorene (0.47 g, 1.1 mmol) was dissolved in anhydrous methanol (MeOH) (5 mL) under an argon atmosphere. NaBH$_4$ (1.2 eq, 1.3 mmol, 0.05 g) was added and the reaction was stirred at room temperature for five hours. The reaction was diluted with deionized water and acidified to pH 5 with glacial acetic acid. The reaction was extracted with ethyl acetate (2×100 mL) and the organic layers were washed with saturated NaHCO$_3$ (4×20 mL) and brine (3×20 mL). The organic layers were dried over MgSO$_4$, filtered and evaporated. The crude product, orange solid, was purified by flash chromatography: silica gel 60 Å gradient elution 1-5% methanol in chloroform (alternative gradient elution with 15-20% ethyl acetate in dichloromethane). Product was a yellow solid (0.39, 83%). $^1$H-NMR (CD$_3$OD): δ (ppm) 7.9 (s, 0.5H, NH urethane); 7.7 (s, 2H, Ar); 7.6 (d, 2H, Ar); 7.4 (d, 2H, Ar); 4.0 (m, 1H, CH); 3.9 (m, 2H, CH$_2$); 1.6 (s, 18H, Boc).

D. Preparation of 9-hydroxymethyl-2,7-diaminofluorene dihydrochloride

9-Hydroxymethyl-2,7-di(Boc-amino)fluorene (0.39 g, 0.9 mmol) was dissolved in 1,4-dioxane. At 0° C. concentrated HCl (2.5 mL) was added and the reaction was stirred for two hours at 0° C. and for one hour at room temperature. The reaction solvents were removed at reduced pressure (45° C.). The product was dissolved in methanol and evaporated (2 times). The product was dissolved in methanol (8 mL) and precipitated by the slow addition of diethyl ether and cooling (repeat). The product was a red-orange solid (0.25 g, 91%) that showed a single spot by TLC (chloroform/methanol/acetic acid 85:15:3, ninhydrin stain). $^1$H-NMR (CD$_3$OD): δ (ppm) 8.1 (d, 2H, Ar); 7.8 (s, 2H, Ar); 7.5 (d, 2H, Ar); 4.3 (t, 1H, CH); 4.0 (d, 2H, CH$_2$)

E. Preparation of 9-hydroxymethyl-2,7-di(mPEG(20,000), oxymethylcarbonylamino)fluorene mPEG-CM(20,000) (mPEG-CM having MW=19,458; 20 g, 1.03 mmol, 3.5 eq), in anhydrous toluene (80 mL) was azeotropically distilled under reduced pressure at 60° C. on a rotary evaporator. The solids were dissolved in anhydrous dichloromethane (40 mL) under an argon atmosphere followed by addition of N-hydroxybenzotriazole (HOBt) anhydrous (3.5 eq, 1.03 mmol, 139 mg) and 1,3-dicyclohexylcarbodiimide (DCC) (3.7 eq, 1.09 mmol, 224 mg). In a separate flask 9-hydroxymethyl-2,7-diaminofluorene dihydrochloride (1 eq, 0.294 mmol, 88 mg) and 4-dimethylaminopyridine (2.2 eq, 0.65 mmol, 79 mg) were dissolved in anhydrous DMF (2.5 mL). After stirring the DCC reaction for several minutes (5-15 minutes), the DMF solution of 9-hydroxymethyl-2,7-diaminofluorene was quantitatively transferred to the DCC reaction. The reaction was stirred at room temperature for 27 hours before solvent was evaporated at reduced pressure. The thick syrup was dissolved in dry isopropyl alcohol (400 mL, slow addition) with gentle heating. The PEG product precipitated on standing at room temperature. Additional isopropyl alcohol was (100 mL) added while stirring at 0° C. for 30 minutes. The precipitate was filtered and washed with cold isopropyl alcohol/diethyl ether 7:3 (80 mL) and diethyl ether. The crude product (pale yellow powder, 9-(mPEG(20,000) methylester)-methyl-2,7-di(mPEG(20,000)-methylamide) fluorene) was dried under hi-vacuum (yield 18.3 g).

Under an argon atmosphere, the crude product (18.3 g) was dissolved in deionized water and adjusted to pH 12±0.1 with NaOH 1M. The hydrolysis reaction mixture was stirred at room temperature for three hours. The pH was adjusted to 3.0 with 10% phosphoric acid. (The aqueous solution was filtered through a bed of celite and rinsed with water.) NaCl (60 g) was dissolved into the aqueous solution and then extracted with dichloromethane (2×150 mL). The combined organic layers were dried over MgSO$_4$, filtered and evaporated at reduced pressure. The crude product was dissolved in deionized water and desalted with ion exchange resin. Ion exchange chromatography of the PEG solution was preformed on DEAE sepharose (0.9 L) eluting with water. Fractions containing PEG were collected. The purified product (pale yellow powder) was absent of mPEG-CM(20,000) (HPLC analysis). Yield 7.3 g, 64% (representing the total amount of PEG material recovered), substitution 75% or better (representing the percentage of PEG, of the amount recovered, having the desired functionality). $^1$H-NMR (CD$_2$Cl$_2$): δ (ppm) 8.9 (s, 2H, NH amide); 7.9 (s, 2H, Ar); 7.7 (m, 4H, Ar); 4.1 (m, 5H, CH$_2$C=O, CH); 4.0 (d, 2H, CH$_2$); 3.6 (s, PEG backbone); 3.3 (s, 3H, —OCH$_3$).

F. N-{di(mPEG(20,000)oxymethylcarbonylamino) fluoren-9-ylmethoxycarbonyloxy}succinimide 9-Hydroxymethyl-2,7-di(mPEG(20,000)-methylamide) fluorene (0.5 g, 0.013 mmol) in anhydrous acetonitrile (10 mL) was azeotropically distilled under reduced pressure at 50° C. on a rotary evaporator. The solid was dissolved in anhydrous dichloromethane (2 mL, "CH$_2$Cl$_2$") followed by addition of triphosgene. (Care was used to trap excess phosgene gas from reaction with base trap) (1.4 eq, 0.018 mmol, 5 mg). After several minutes, anhydrous pyridine (2 eq, 0.026 mmol, 2 μL of pyridine in dichlormethane [2 μL pyridine/50 μL dichloromethane]) was added. At one and one-half hours most of the reaction solvent and excess phosgene (use base trap on vent) was evaporated with gentle warming (40° C.). The syrup was dissolved in anhydrous dichloromethane (2 mL) followed by addition of N-hydroxysuccinimide (5.3 eq, 0.068 mmol, 8 mg, "NHS") and anhydrous pyridine (3.2 eq, 0.041 mmol, 83 μL of the above (2:50) solution in dichloromethane). After hour hours, the solvent was evaporated under an argon stream. The syrup was dissolved in anhydrous isopropyl alcohol and precipitated at room temperature. The precipitate was filtered and washed with cold isopropyl alcohol and diethyl ether. Residual solvents were evaporated under vacuum to give a very pale yellow powder. Yield 0.4 g, 80%, substitution 73% NHS carbonate by HPLC. $^1$H-NMR (CD$_2$Cl$_2$): δ (ppm) 8.9 (s, 2H, NH amide); 7.9 (s, 2H, Ar); 7.7 (m, 4H, Ar); 4.7 (d, 2H, CH$_2$); 4.3 (t, 1H, CH); 4.1 (s, 4H, CH$_2$C=O); 2.8 (s, 4H, CH$_2$CH$_2$ NHS).

Using this same procedure, polymeric reagents having other molecular weights can be prepared by substituting an mPEG-CM polymeric reagent having a molecular weight other than 20,000 daltons.

Example 2

Preparation of N-[2,7 di(4 mPEG(10,000)aminocarbonylbutyrylamino)fluoren-9-ylmethoxycarbonyloxy]succinimide ("G2PEG2Fmoc$_{20k}$-NHS")

The synthesis of mPEG(10,000)aminocarbonylbutyrylamino)fluoren-9-ylmethoxycarbonyloxy]succinimide is represented schematically in Scheme 2 below.

Scheme 2.
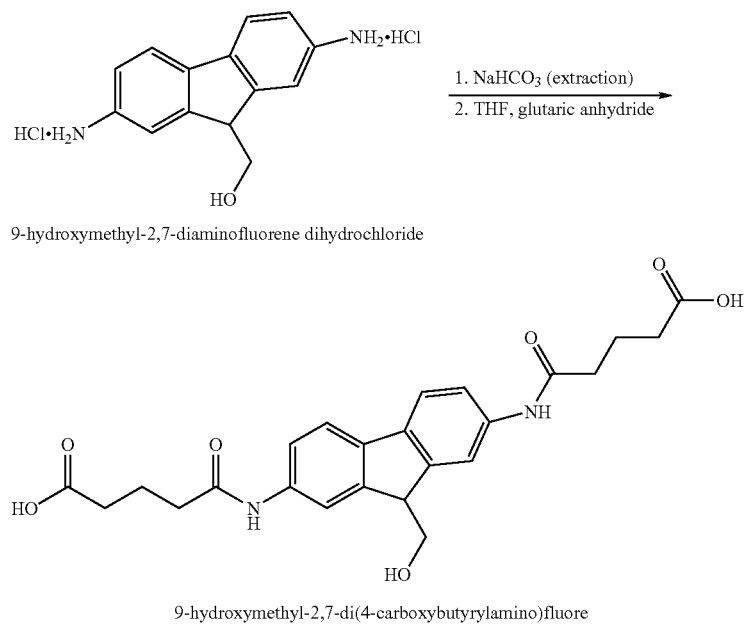
9-hydroxymethyl-2,7-diaminofluorene dihydrochloride
9-hydroxymethyl-2,7-di(4-carboxybutyrylamino)fluore
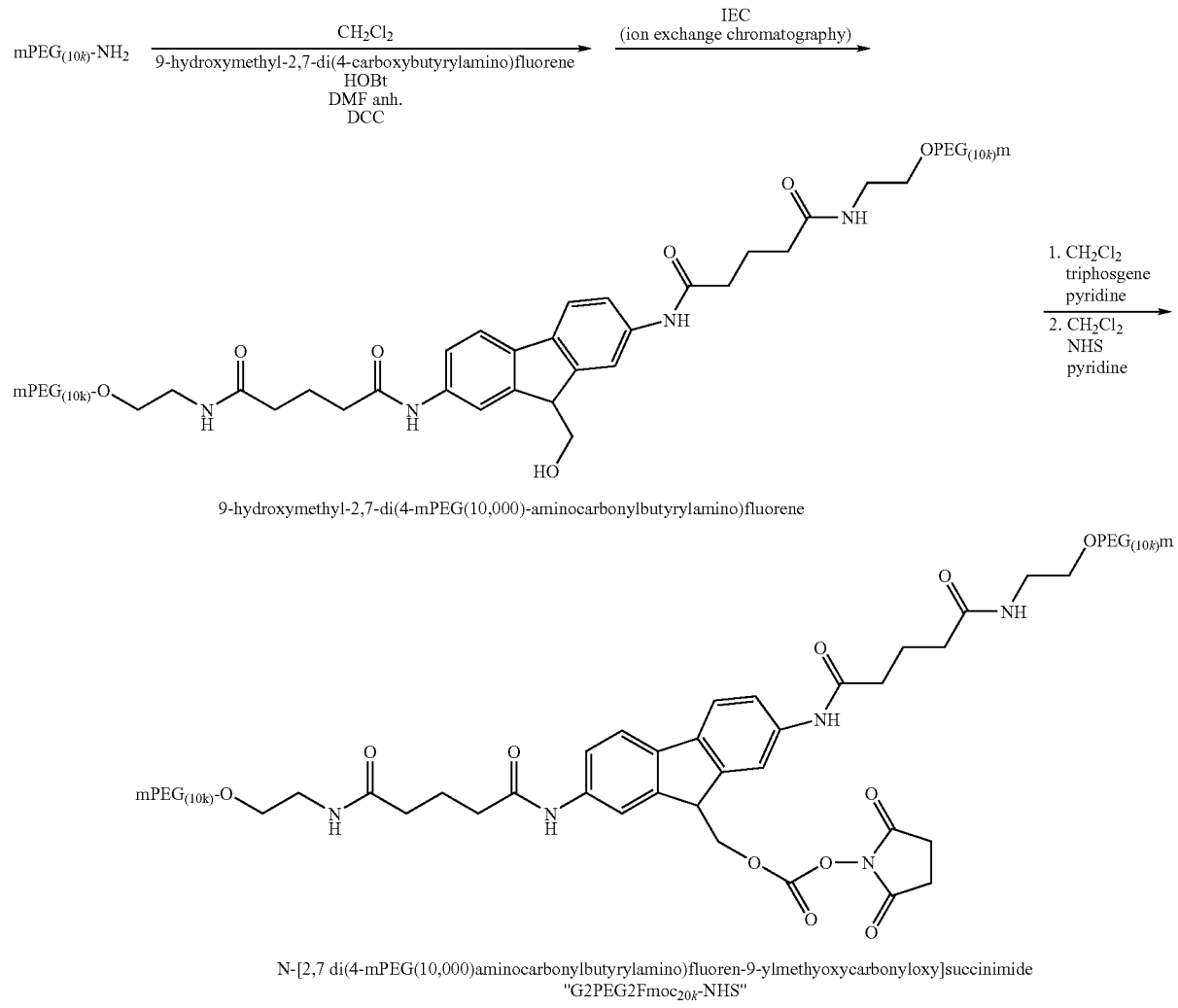
9-hydroxymethyl-2,7-di(4-mPEG(10,000)-aminocarbonylbutyrylamino)fluorene
N-[2,7 di(4-mPEG(10,000)aminocarbonylbutyrylamino)fluoren-9-ylmethyoxycarbonyloxy]succinimide
"G2PEG2Fmoc$_{20k}$-NHS"

A. 9-Hydroxymethyl-2,7-di(4-carboxybutyrylamino) fluorene

Under an argon atmosphere, 9-hydroxymethyl-2,7-diaminofluorene dihydrochloride (preparation described in steps A through D in Example 1) was dissolved in deionized water and adjusted to pH 8 with saturated NaHCO$_3$. The mixture was diluted in half with brine and the precipitate was extracted with ethyl acetate. The ethyl acetate layers were dried over Na$_2$SO$_4$, filtered and evaporated for 9-hydroxymethyl-2,7-diaminofluorene (brown powder, 84% isolated yield).

9-Hydroxymethyl-2,7-diaminofluorene (0.38 g, 1.7 mmol) was dissolved in anhydrous tetrahydrofuran (THF) (10 mL) and glutaric anhydride (97%, 2.2 eq, 3.7 mmol, 0.435 g) was added. The reaction was stirred for 4.5 hours and absence of amine was confirmed by TLC (ninhydrin stain, 90:10:3 ethyl acetate/methanol/acetic acid). The reaction mixture was diluted with hexanes (10 mL), filtered and washed with 1:1 THF/hexanes then hexanes. The crude product was dissolved in a minimal amount of methanol (1 mL) and THF (10 mL) and precipitated with addition of hexanes (10 mL). The mixture was cooled (4° C.), filtered and washed with 1:1 THF/Hexanes then hexanes. Yield was 0.59 g (77%) of yellow-orange powder. 1H-NMR (CD$_3$OD): δ (ppm) 7.9 (s, 2H, Ar); 7.7 (d, 2H, Ar); 7.5 (dd, 2H, Ar); 4.0 (t, 1H, CH); 3.9 (d, 2H, CH2); 2.5 (t, 4H, CH2); 2.4 (t, 4H, CH2); 2.0 (m, 4H, CH2).

B. 9 Hydroxymethyl-2,7-di(4 mPEG(10,000)-aminocarbonylbutyrylamino)fluorene mPEG-NH2(10,000) (Mn=10,200; chromatographically purified, 12.75 g, 1.25 mmol) in anhydrous toluene (100 mL) was azeotropically distilled under reduced pressure at 50° C. on a rotary evaporator. The solids were dissolved in anhydrous dichloromethane (50 mL) under an argon atmosphere. A solution of 9-hydroxymethyl-2,7-di(amidoglutaric acid) fluorene (1 eq., 0.5 mmol, 0.225 g) and N-hydroxybenzotriazole (HOBt) anhydrous (2.2 eq, 1.1 mmol, 149 mg) in anhydrous DMF (5 mL) was quantitatively added to the PEG solution (2.5 mL DMF to rinse). 1,3-Dicyclohexylcarbodiimide (DCC) (2.4 eq, 1.2 mmol, 248 mg) was then added to the reaction solution. The reaction was stirred at room temperature for 24 hours before solvent was evaporated at reduced pressure. The thick syrup was dissolved in dry isopropyl alcohol (500 mL, slow addition) with gentle heating. The PEG product precipitated on standing at room temperature. The precipitate was cooled to 10° C. for ten minutes, filtered and washed with cold isopropyl alcohol (200 mL) and then diethyl ether (200 mL). The crude product (off-white powder) was dried under hi-vacuum and then dissolved in deionized water. Ion exchange chromatography of the PEG solution was preformed on POROS media (0.1 L, Boehringer-Mannheim, GmbH, Mannheim Germany) eluting with water. Fractions containing neutral PEG were collected. The purified product contained no mPEG-NH2(10,000) (HPLC analysis). Yield 5.5 g, 53%, substitution 85% or better. 1H-NMR (CD2C12): δ (ppm) 8.6 (s, 2H, ArNH amide); 7.9 (s, 2H, Ar); 7.6 (m, 4H, Ar); 6.4 (bs, 2H, NH amide); 4.1 (m, 1H, CH); 4.0 (d, 2H, CH2); 3.6 (s, PEG backbone); 3.3 (s, 3H, —OCH3); 2.4 (t, 4H, CH2); 2.3 (t, 4H, CH2); 2.0 (m, 4H, CH2).

C. N-[2,7 di(4 mPEG(10,000)aminocarbonylbutyrylamino)fluoren-9-yl methoxycarbonyloxy]succinimide 9-Hydroxymethyl-2,7-di(4 mPEG(10,000)-aminocarbonylbutyrylamino)fluorene (5.3 g, 0.25 mmol) in anhydrous acetonitrile (100 mL) was azeotropically distilled under reduced pressure at 50° C. on a rotary evaporator. The solid was dissolved in anhydrous dichloromethane (27 mL) followed by addition of triphosgene (1.4 eq, 0.36 mmol, 106 mg). (Care was used to trap excess phosgene gas from reaction with base trap.). After several minutes, anhydrous pyridine (2 eq, 0.51 mmol, 41 µL) was added. After one and one-half hours, most of the reaction solvent and excess phosgene (use base trap on vent) was evaporated with gentle warming (40° C.). The syrup was dissolved in anhydrous dichloromethane (15 mL) followed by addition of N-hydroxysuccinimide (5.3 eq, 1.35 mmol, 155 mg, "NHS"). After 15 minutes anhydrous pyridine (3.2 eq, 0.81 mmol, 66 µL) was added. The reaction was stirred for two hours and the solvent was evaporated under reduced pressure. The syrup was dissolved in anhydrous isopropyl alcohol (200 mL) and precipitated at room temperature. The precipitate was filtered and washed with cold isopropyl alcohol and diethyl ether (150 mL containing 10 mg BHT). Residual solvents were evaporated under vacuum to provide an off-white powder. Yield 5.1 g, 95%, substitution ~70% NHS carbonate by HPLC.

Another polymeric reagent was prepared using this same approach except mPEG-NH$_2$ (chromatographically purified) having a weight average molecular weight of about 20,000 was substituted for mPEG-NH$_2$(10,000). The resulting polymeric reagent had a total molecular weight of about 40,000 Daltons. The name of polymeric reagent so prepared is 9-yy-droxymethyl-2,7-di(4 mPEG(20,000)-aminocarbonylbutyrylamino)fluorene (or "G2PEG2Fmoc$_{40k}$-NHS").

Another polymeric reagent was prepared using this same approach except mPEG-NH$_2$ (prepared in high purity using conventional methods) having a weight average molecular weight of about 30,000 was substituted for mPEG-NH$_2$(10,000). The resulting polymeric reagent had a total molecular weight of about 60,000 Daltons. The name of polymeric reagent so prepared is 9-hydroxymethyl-2,7-di(4 mPEG(30,000)-aminocarbonylbutyrylamino)fluorene (or "G2PEG2Fmoc$_{60k}$-NHS").

Example 3

Preparation of an Exemplary GLP-1-Polymer Conjugate Having a Releasable PEG Moiety Attached to GLP-1

Preparation of G2PEG2Fmoc$_{20k}$-N$^{ter}$-GLP-1

An illustrative polymeric reagent, G2PEG2Fmoc20k-NHS, was covalently attached to the N-terminus of GLP-1, to provide a prodrug form of the protein wherein the PEG-moiety is releasably attached. The two-arm nature of the polymeric reagent provides increased stability to the GLP-1 moiety subsequent to administration, to thereby provide a sustained release formulation whereby GLP-1 is released from the conjugate via hydrolysis to provide the native or unmodified GLP-1 precursor. The structure of G2PEG2Fmoc$_{20k}$-N$^{ter}$-GLP-1 is provided below (in the structure, "GLP-1" represents a residue of GLP-1).

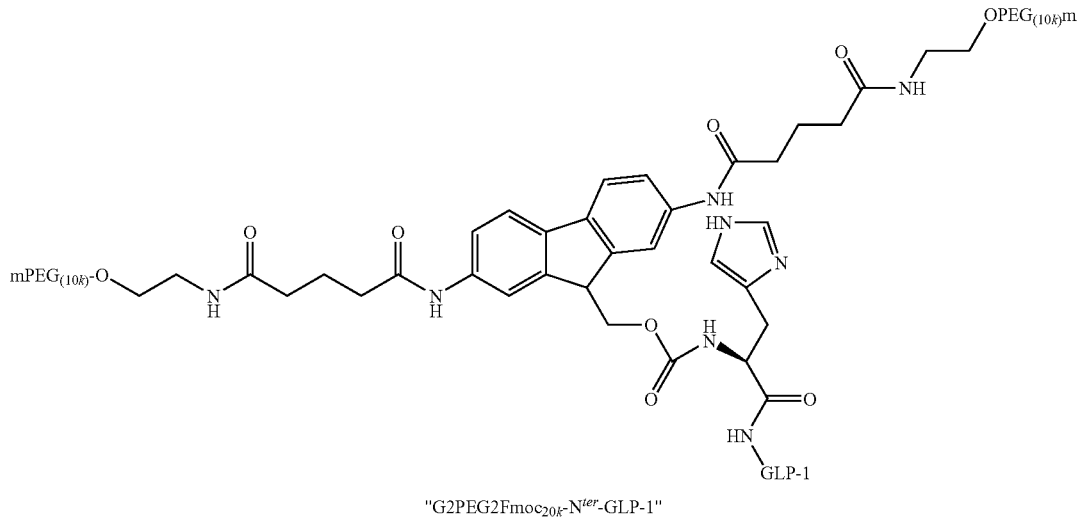

"G2PEG2Fmoc$_{20k}$-N$^{ter}$-GLP-1"

The polymeric reagent, G2PEG2Fmoc$_{20K}$-NHS, was prepared as described above in Example 2.

A solution of 50 mg GLP-1 (nominally 1.2276×10$^{-5}$ mol) (actual purity of GLP-1 was 98.5% (by HPLC), and the peptide content was 82.2%) in 25 mL of 20 mM sodium acetate buffer at pH 5.50 was prepared, followed by addition of 876.8 mg of G2PEG2Fmoc$_{20k}$-NHS (3.0692×10$^{-5}$ mol) with stirring. The solution was allowed to stir for 16 hours at room temperature, thereby allowing for the formation of G2PEG2Fmoc$_{20k}$-N$^{ter}$-GLP-1, a PEGylated GLP-1 conjugate. The reaction mixture was then acidified to pH 4.30 by 20 mM HAc. The reaction was monitored by SDS-PAGE analysis (FIG. 1).

Figure 2:
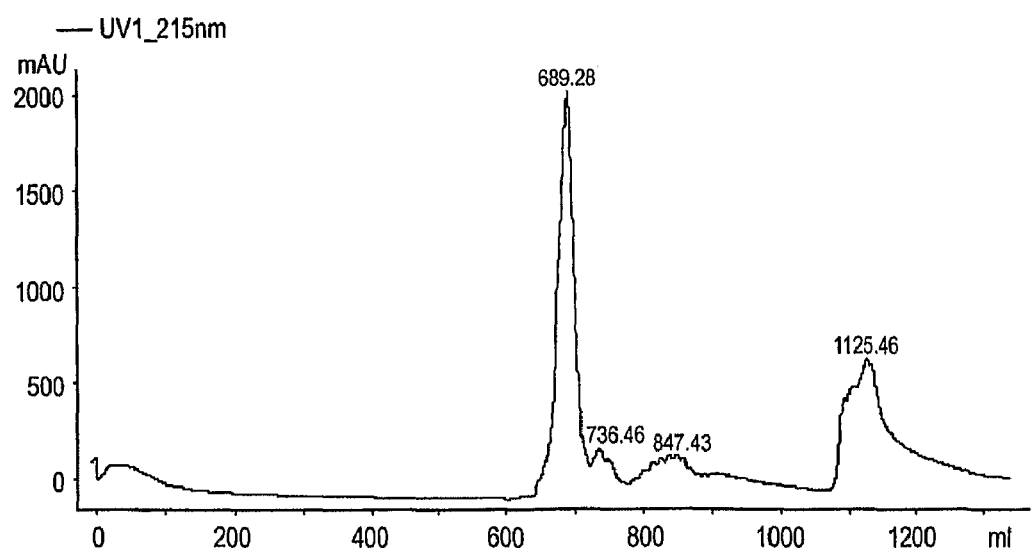
FIG. 2 demonstrates the results of purification of monoPEGylated G2PEG2Fmoc$_{20k}$-N$^{ter}$-GLP-1 by cation exchange chromatography as described in Example 3.

The G2PEG2Fmoc$_{20k}$-N$^{ter}$-GLP-1 was purified to obtain the monoPEGylated conjugate of GLP-1 by cation exchange chromatography on an ÄKTA Basic System (FIG. 2) using a mobile phase of 20 mM sodium acetate buffer at pH 4.30 (Solution A) and 20 mM sodium acetate buffer with 1 M NaCl at pH 4.30 (Solution B). The column was a Vantage L Laboratory Column VL (Milllipore) packed with SP Sepharose High Performance ion exchange media available from Amersham Biosciences. The flow rate was 14 mL/min. The solution to be purified was first loaded onto the column. The loaded product was then eluted by the mobile phase using a gradient. The following gradient was used: for retention volumes 0 mL to 550 mL, 0% of the mobile phase contained solution B; for retention volumes 550 mL to 1041 mL, 0% of the mobile phase contained solution B; for retention volumes 1041 mL to 1093 mL, 10% of the mobile phase contained solution B; for retention volumes 1093 mL to 1338 mL, 100% of the mobile phase contained solution B; for retention volumes 1338 mL to 1486 mL, 100% of the mobile phase contained solution B; for retention volumes 1486 mL and higher, 0% of the mobile phase contained solution B. The UV absorbance of the eluent was monitored at 215 nm. The fraction corresponding to the G2PEG2Fmoc$_{20k}$-N$^{ter}$-GLP-1 (monoPEGylated form) peak at a retention volume of 689.3 mL was collected (FIG. 2) and lyophilized. The lyophilized powder was dissolved in 25 mL 20 mM sodium acetate buffer at pH 4.3, and the purification process was repeated again under the same cation exchange chromatographic conditions. Yield: 179.4 mg.

Figure 3:
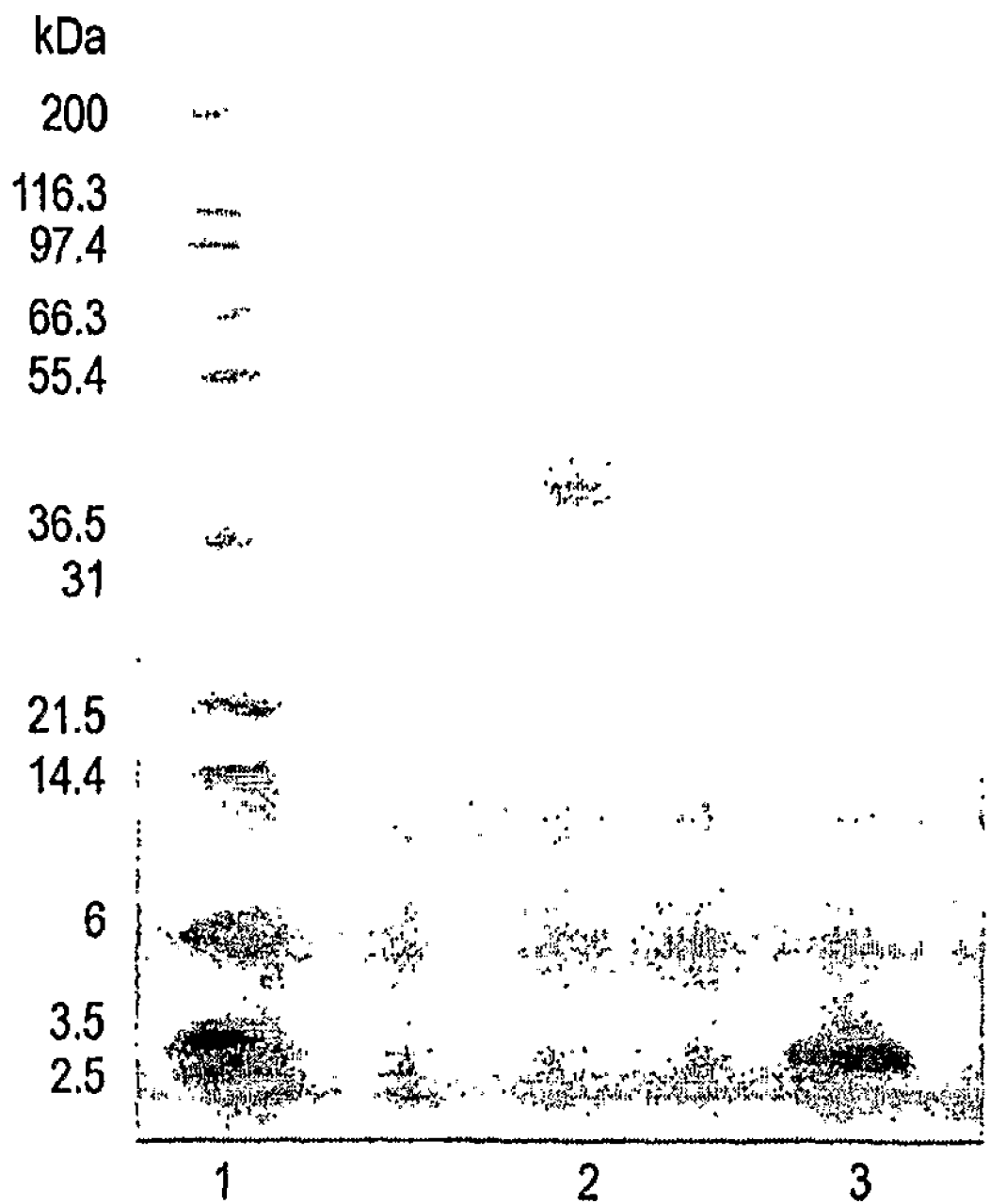
FIG. 3 corresponds to an SDS-PAGE analysis of monoPEGylated G2PEG2Fmoc$_{20k}$-N$^{ter}$-GLP-1 before and after the release of GLP-1 (Example 3). Lane 1: Invitrogen Mark 12 unstained standard. Lane 2: MonoPEGylated G2PEG2-Fmoc$_{20k}$-N$^{ter}$-GLP-1 conjugate following purification by ion exchange chromatography. Lane 3: Following complete release of GLP-1 from the G2PEG2Fmoc$_{20k}$-N$^{ter}$-GLP-1 conjugate.
Figure 4A:
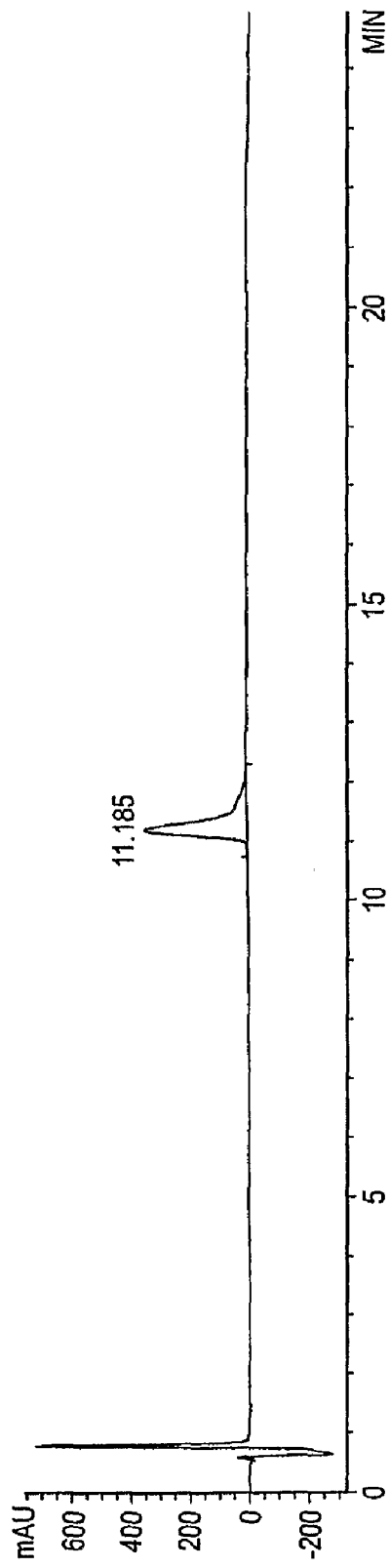
FIGS. 4A, 4B demonstrate a reverse phase HPLC analysis of monoPEGylated G2PEG2Fmoc$_{20k}$-N$^{ter}$-GLP-1 conjugate following purification by ion exchange chromatography (FIG. 4A) and after release of GLP-1 from the G2PEG2Fmoc$_{20k}$-N$^{ter}$-GLP-1 conjugate (FIG. 4B), as described in Example 3.
Figure 4B:
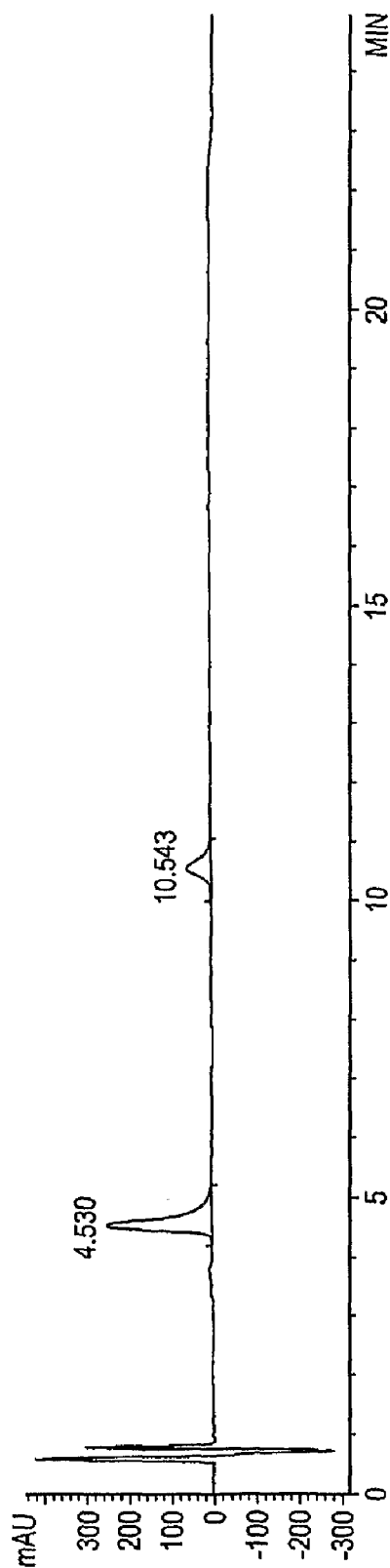

The purified G2PEG2Fmoc$_{20k}$-N$^{ter}$-GLP-1 was analyzed by SDS-PAGE (FIG. 3, Lane 2) and reverse phase HPLC (FIG. 4A). The cleavable nature of the G2PEG2Fmoc$_{20k}$-N$^{ter}$-GLP-1 conjugate in aqueous media [50 mM tris(hydroxymethyl)aminomethane (Tris) solution, pH 10, overnight at 50° C.] was also studied by both SDS-PAGE analysis (FIG. 3, Lane 3) and reverse phase HPLC (FIG. 4B), from which the complete release of GLP-1 from the conjugate was observed. The column was a 100 mm×2.1 mm ID Betasil C18 column with 5 μm particles, available from Thermo Electron Corp. Reverse phase HPLC used a mobile phase of 0.1% TFA in deionized water (solution C) and 0.1% TFA in acetonitrile (solution D) conducted at 37° C. The gradient used for reverse phase HPLC was as follows: for time 0.00 to 20.00 minutes, 35% of the mobile phase contained solution D; for time 20.00 to 21.00 minutes, 55% of the mobile phase contained solution D; for time 21.00 to 23.00 minutes, 80% of the mobile phase contained solution D; for time 23.00 to 24.00 minutes, 80% of the mobile phase contained solution D; for time 24.00 to 25.00 minutes, 35% of the mobile phase contained solution D; for time 25.00 and above, 35% of mobile phase contained solution D.

The N-terminal PEGylation site (His$^7$) of the G2PEG2Fmoc$_{20k}$-N$^{ter}$-GLP-1 conjugate (a monoPEGylated species) was confirmed by MALDI-TOF analysis following protease digestion of the conjugate using Endoproteinase Glu-C from *Staphylococcus aureus* V8.

Example 4

Preparation of an Exemplary GLP-1-Polymer Conjugate Having a Releasable PEG Moiety Attached to GLP-1

Preparation of G2PEG2Fmoc$_{40k}$-N$^{ter}$-GLP-1

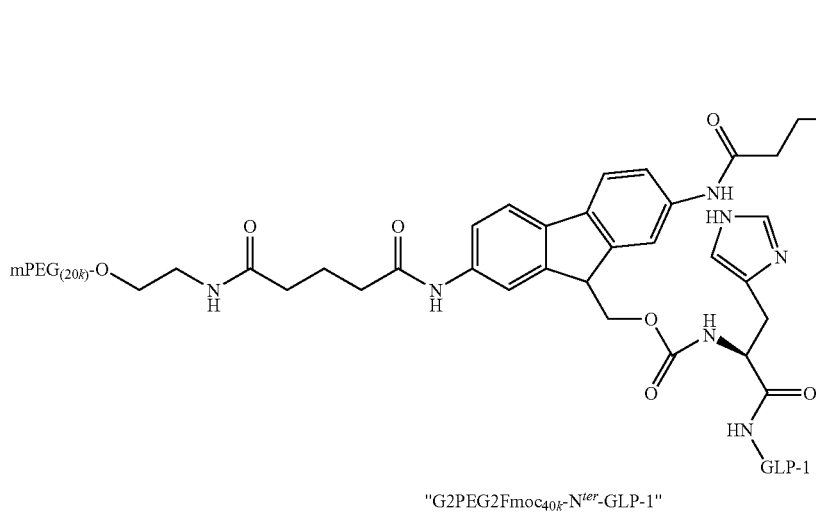

"G2PEG2Fmoc$_{40k}$-N$^{ter}$-GLP-1"

The polymeric reagent, G2PEG2Fmoc$_{40k}$-NHS, was prepared as described above in Example 2.

A solution of 50 mg GLP-1 (nominally 1.2276×10$^{-5}$ mol) (actual purity of GLP-1 was 98.5% (by HPLC), and the peptide content was 82.2%) in 25 mL of 20 mM sodium acetate buffer at pH 5.50 was prepared, followed by addition of 1.4971 gm of G2PEG2Fmoc$_{40k}$-NHS (3.0692×10$^{-5}$ mol) with stirring. The solution was allowed to stir for 15 hours at room temperature, thereby allowing for the formation of G2PEG2Fmoc$_{40k}$-N$^{ter}$-GLP-1, a PEGylated GLP-1 conjugate. The reaction mixture was acidified to pH 4.00 by 2 N HAc, followed by dilution to 50 mL with 20 mM sodium acetate buffer at pH 4.00.

Figure 5:
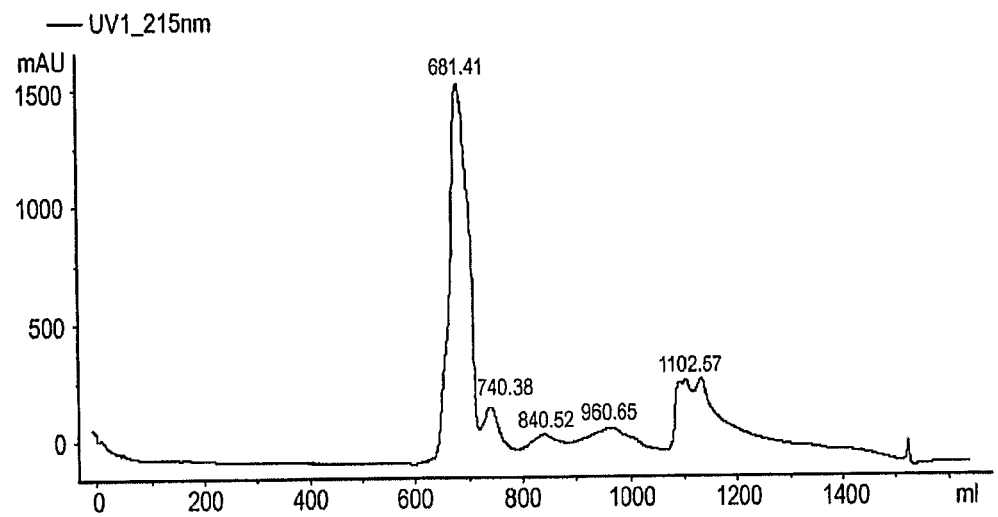
FIG. 5 illustrates the results of purification of monoPEGylated G2PEG2Fmoc$_{40k}$-N$^{ter}$-GLP-1 by cation exchange chromatography as described in Example 4.

The G2PEG2Fmoc$_{40k}$-N$^{ter}$-GLP-1 was purified to obtain the monoPEGylated conjugate of GLP-1 by cation exchange chromatography on an ÄKTA Basic System (FIG. 5). The column was a Vantage L Laboratory Column VL (Millipore) packed with SP Sepharose High Performance ion exchange media (Amersham Biosciences). The flow rate in the column was 14 mL/min. The mobile phase used for the purification consisted 20 mM sodium acetate buffer at pH 4.00 (solution A) and 20 mM sodium acetate buffer with 1 M NaCl at pH 4.00 (solution B). The solution to be purified was first loaded onto the column. The loaded product was then eluted by the mobile phase using a gradient. The following gradient was used: for retention volumes 0 mL to 550 mL, 0% of the mobile phase contained solution B; for retention volumes 550 mL to 1041 mL, 0% of the mobile phase contained solution B; for retention volumes 1041 mL to 1093 mL, 10% of the mobile phase contained solution B; for retention volumes 1093 mL to 1338 mL, 100% of the mobile phase contained solution B; for retention volumes 1338 mL to 1486 mL, 100% of the mobile phase contained solution B; for retention volumes 1486 mL and higher, 0% of the mobile phase contained solution B. The UV absorbance of the eluent was monitored at 215 nm. The fraction corresponding to mono G2PEG2Fmoc$_{40k}$-N$^{ter}$-GLP-1 peak at retention volume of 668.4 mL was collected (FIG. 5) and lyophilized. The lyophilized powder was dissolved in 25 mL 20 mM sodium acetate buffer at pH 4.0, and the purification process was repeated again under the same cation exchange chromatographic conditions. The collection fraction at 668 mL was lyophilized.

Figure 6:
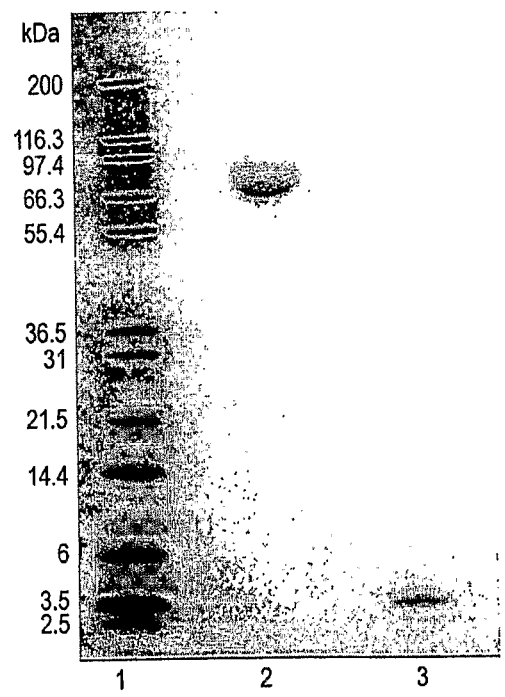
FIG. 6 shows the results of an SDS-PAGE analysis of monoPEGylated G2PEG2Fmoc$_{40k}$-N$^{ter}$-GLP-1 before and after release of GLP-1 (Example 4). Lane 1: Invitrogen Mark 12 unstained standard. Lane 2: MonoPEGylated G2PEG2Fmoc$_{40k}$-N$^{ter}$-GLP-1 conjugate following purification by ion exchange chromatography. Lane 3: Following release of GLP-1 from the G2PEG2-Fmoc$_{40k}$-N$^{ter}$-GLP-1 conjugate.

The purified G2PEG2Fmoc$_{40k}$-N$^{ter}$-GLP-1 was analyzed by SDS-PAGE (FIG. 6, Lane 2). The cleavable nature of the G2PEG2Fmoc$_{40k}$-N$^{ter}$-GLP-1 conjugate in aqueous media The cleavable nature of the G2PEG2Fmoc$_{20k}$-N$^{ter}$-GLP-1 conjugate in aqueous media [50 mM tris(hydroxymethyl) aminomethane (Tris) solution, pH 10, overnight at 50° C.] was also studied by SDS-PAGE analysis (FIG. 6, Lane 3), from which the complete release of GLP-1 from the conjugate was observed.

Example 5

Preparation of an Exemplary GLP-1-Polymer Conjugate Having a Releasable PEG Moiety Attached to GLP-1

Preparation of G2PEG2Fmoc$_{20k}$-Lys-GLP-1

The exemplary releasable polymeric reagent, G2PEG2Fmoc$_{20k}$-NHS, was covalently and releasably attached to a lysine position of GLP-1, referred to herein as "internal" PEGylation of GLP-1.

A solution of 30 mg GLP-1 (nominally 7.3658×10$^{-6}$ mol) (actual purity of GLP-1 was 98.5% (by HPLC), and the peptide content was 82.2%) in 24.5 mL of 20 mM sodium carbonate-bicarbonate buffer at pH 10.0 was prepared, followed by addition of 276.3 mg of G2PEG2Fmoc$_{20k}$-NHS (1.1049× 10$^{-5}$ mol, prepared as described above in Example 2) with stirring. The solution was allowed to stir for ten minutes at room temperature. The reaction mixture was then acidified to pH 4.30 by 2 N HAc.

Figure 7:
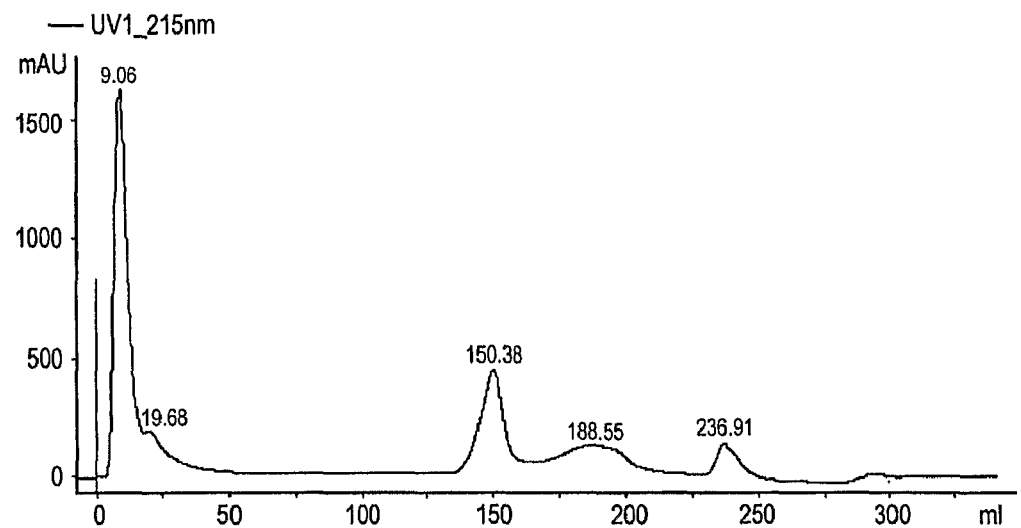
FIG. 7 demonstrates purification of monoPEGylated G2PEG2Fmoc$_{20k}$-Lys-GLP-1 by cation exchange chromatography (Example 5).
Figure 8:
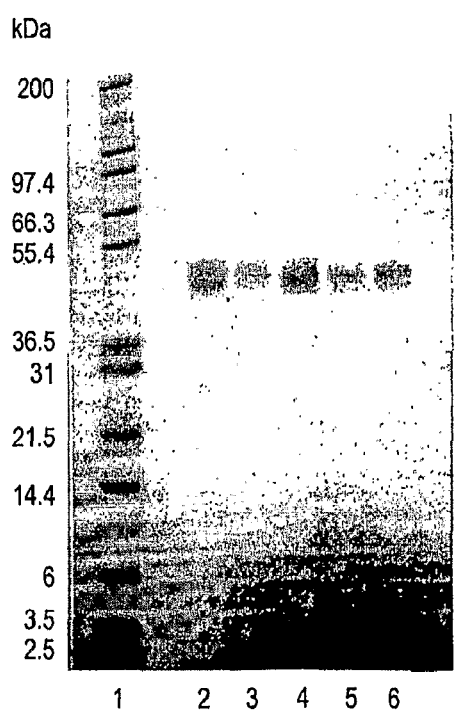
FIG. 8 corresponds to an SDS-PAGE analysis of monoPEGylated G2PEG2Fmoc$_{20k}$-Lys-GLP-1 purified by cation exchange chromatography (Example 5). Lane 1: Invitrogen Mark 12 unstained standard. Lanes 2 through 6: Fractions containing monoPEGylated G2PEG2Fmoc$_{20k}$-Lys-GLP-1 conjugate following five individual purifications by ion exchange chromatography.

To obtain the G2PEG2Fmoc$_{20k}$-Lys-GLP-1 in mono-PEGylated form, the reaction mixture was divided into five aliquots, and each aliquot was individually purified by cation exchange chromatography on an ÄKTA Basic System. The column was a 5 mL resin-packed HiTrap™ SP HP, available from Amersham Biosciences, and the flow rate in the column was 5 mL/min. The mobile phase used for the purification was 20 mM sodium acetate buffer at pH 4.30 (solution A) and 20 mM sodium acetate buffer with 1 M NaCl at pH 4.30 (solution B). The mobile phase was run using a gradient. The following gradient was used: 0 mL to 118.6 mL, 0% of the mobile phase contained solution B; for retention volumes 118.6 mL to 219.1 mL, 0% of the mobile phase contained solution B; for retention volumes 219.1 mL to 229.2 mL, 10% of the mobile phase contained solution B; for retention volumes 229.2 mL to 269.4 mL, 100% of the mobile phase contained solution B; for retention volumes 269.4 mL to 279.4 mL, 100% of the mobile phase contained solution B; for retention volumes 279.4 mL and higher, 0% of the mobile phase contained solution B. The UV absorbance of the eluent was monitored at 215 nm. The monoPEGylated GLP-1 fraction corresponding to the G2PEG2-Fmoc$_{20k}$-Lys-GLP-1 peak at a retention volume of 150.4 mL was collected (FIG. 7) during each purification run. The purified G2PEG2Fmoc$_{20k}$-Lys-GLP-1 (in the monoPEGylated GLP-1 form) from each purification run was then analyzed by SDS-PAGE (FIG. 8). The collected fractions were combined and lyophilized. Yield: 41 mg.

Example 6

Preparation of an Exemplary GLP-1-Polymer Conjugate Having a Releasable PEG Moiety Attached to GLP-1

Preparation of G2PEG2Fmoc$_{40k}$-Lys-GLP-1

The exemplary releasable polymeric reagent, G2PEG2Fmoc$_{40k}$-NHS, was covalently and releasably attached to a lysine position of GLP-1, referred to herein as "internal" PEGylation of GLP-1.

A solution of 50 mg GLP-1 (nominally 1.2276×10$^{-5}$ mol) (actual purity of GLP-1 was 98.5% (by HPLC), and the peptide content was 82.2%) in 45 mL of 20 mM sodium carbonate-bicarbonate buffer at pH 10.0 was prepared, followed by addition of 898.0 mg of G2PEG2Fmoc$_{40k}$-NHS (1.8414×10$^{-5}$ mol, prepared as described in Example 2) with stirring. The solution was allowed to stir for ten minutes at room temperature. The reaction mixture was then acidified to pH 4.00 by 2 N HAc.

Figure 9:
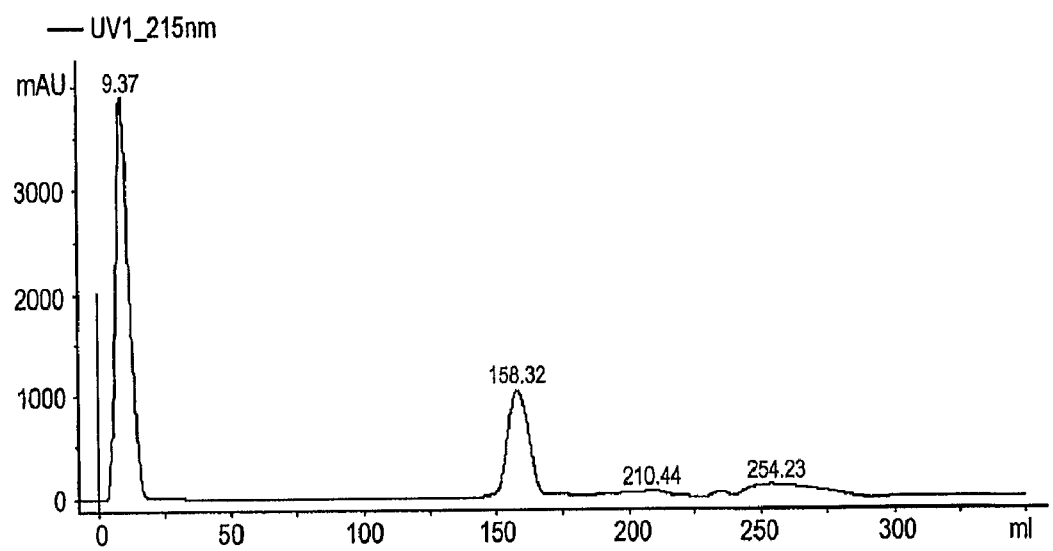
FIG. 9 illustrates the results of purification of monoPEGylated G2PEG2Fmoc$_{40k}$-Lys-GLP-1 by cation exchange chromatography (Example 6).
Figure 10:
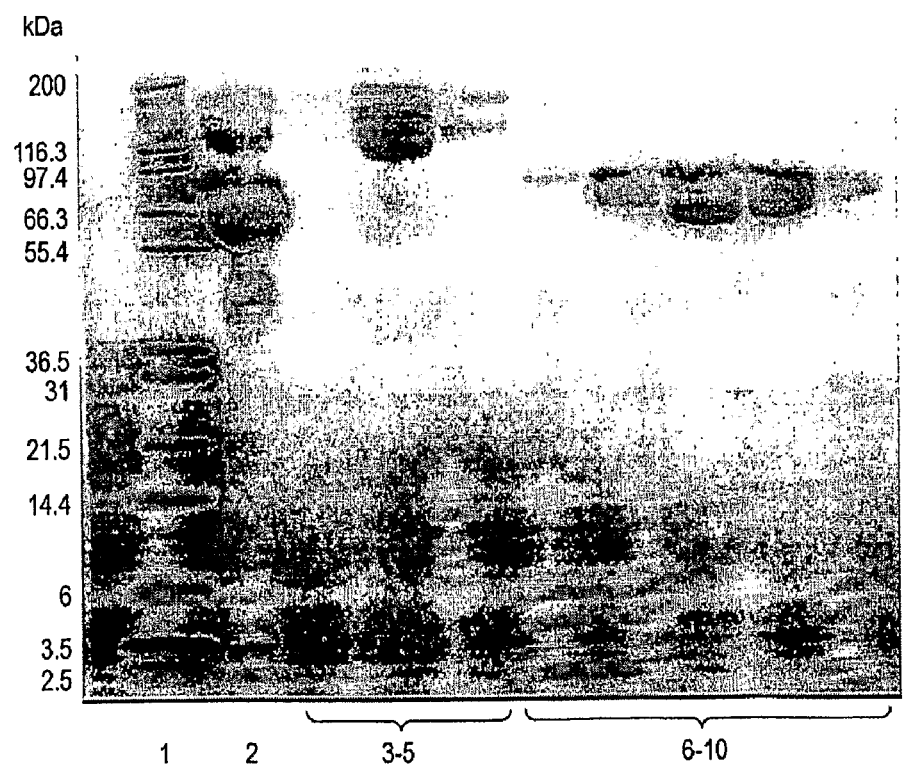
FIG. 10 represents an SDS-PAGE analysis of G2PEG2Fmoc$_{40k}$-Lys-GLP-1 reaction mixture and fractions from one cation exchange chromatographic purification as described in Example 6. Lane 1: Invitrogen Mark 12 unstained standard. Lane 2: Reaction mixture of G2PEG2Fmoc$_{40k}$-Lys-GLP-1. Lanes 3-5: Fractions from the peak at retention volume of 9.37 mL. Lanes 6-10: Fractions of monoPEGylated G2PEG2Fmoc$_{40k}$-Lys-GLP-1 collected from the peak at retention volume of 158.3 mL.

To obtain the G2PEG2Fmoc$_{40k}$-Lys-GLP-1 in monoPEGylated form, the acidified reaction mixture (50 mL), was divided into 10 aliquots, and each 5 mL aliquot was purified by cation exchange chromatography on an ÄKTA Basic System. The column was a 5 mL resin-packed HiTrap™ SP HP, available from Amersham Biosciences, and the flow rate in the column was 5 mL/min. The mobile phase used for the purification was 20 mM sodium acetate buffer at pH 4.00 (A) and 20 mM sodium acetate buffer with 1 M NaCl at pH 4.00 (B). The mobile phase was run using a gradient. The following gradient was used: 0 mL to 118.6 mL, 0% of the mobile phase contained solution B; for retention volumes 118.6 mL to 219.1 mL, 0% of the mobile phase contained solution B; for retention volumes 219.1 mL to 229.2 mL, 10% of the mobile phase contained solution B; for retention volumes 229.2 mL to 269.4 mL, 100% of the mobile phase contained solution B; for retention volumes 269.4 mL to 279.4 mL, 100% of the mobile phase contained solution B; for retention volumes 279.4 mL and higher, 0% of the mobile phase contained solution B. The UV absorbance of the eluent was monitored at 215 nm. The monoPEGylated GLP-1 fraction corresponding to the G2PEG2-Fmoc$_{40k}$-Lys-GLP-1 peak at a retention volume of 158.3 mL was collected (FIG. 9) during each purification run. The purified G2PEG2Fmoc$_{40k}$-Lys-GLP-1 (in the mono-PEGylated GLP-1 form) from each purification run was analyzed by SDS-PAGE (FIG. 10). The collected fractions were combined, concentrated by ultrafiltration and lyophilized. Yield: 187.5 mg.

Example 7

Preparation of an Exemplary GLP-1-Polymer Conjugate Having PEG Stably Attached to GLP-1

Preparation of mPEG$_{2k}$-O—CH$_2$CH$_2$C(O)—HN-Lys-GLP-1

Unlike the monoPEGylated GLP-1 conjugates described in Examples 3 to 6, which are cleavable under physiological conditions to release GLP-1, the monoPEGylated mPEG$_{2k}$-Lys-GLP-1 described in this example is an mPEG-GLP-1 conjugate formed by a stable amide stable linkage on one GLP-1's lysine residues. A preparation method is described below.

A solution of 100 mg GLP-1 (nominally 2.4553×le mol) (actual purity of GLP-1 was 98.5% (by HPLC), and the peptide content was 82.2%) in 90 mL of 20 mM sodium carbonate bicarbonate buffer at pH 10.0 was prepared, followed by addition of 90.7 mg of mPEG-SPA 2K (3.6829×10$^{-5}$ mol) with stirring. The solution was allowed to stir for ten minutes at room temperature. The reaction mixture was then acidified to pH 4.30 by 2 N HAc to a final volume of 100 mL. The solution was diluted to 200 mL by addition of deionized water, and the diluted solution had a pH of 4.30.

Figure 11:
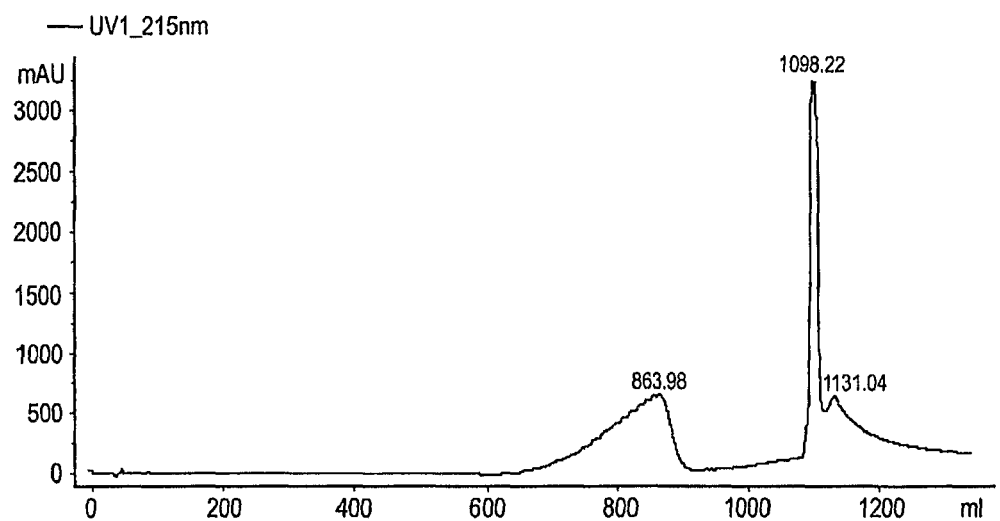
FIG. 11 demonstrates the results of purification of monoPEGylated mPEG$_{2k}$-Lys-GLP-1 by cation exchange chromatography as described in Example 7.

This monoPEGylated form of GLP-1 so formed, designated "mPEG$_{2k}$-Lys-GLP-1," was purified by cation exchange chromatography on an ÄKTA Basic System. The column was a Vantage L Laboratory Column VL (Millipore) packed with SP Sepharose High Performance ion exchange media (Amersham Biosciences). The flow rate was 14 mL/min. The mobile phase used for the purification was 20 mM sodium acetate buffer at pH 4.30 (solution A) and 20 mM sodium acetate buffer with 1 M NaCl at pH 4.30 (solution B). The solution to be purified was first loaded onto the column. The loaded product was then eluted using a gradient mobile phase. The following gradient was used: for retention volumes 0 mL to 550 mL, 0% of the mobile phase contained solution B; for retention volumes 550 mL to 1041 mL, 0% of the mobile phase contained solution B; for retention volumes 1041 mL to 1093 mL, 10% of the mobile phase contained solution B; for retention volumes 1093 mL to 1338 mL, 100% of the mobile phase contained solution B; for retention volumes 1338 mL to 1486 mL, 100% of the mobile phase contained solution B; for retention volumes 1486 mL and higher, 0% of the mobile phase contained solution B. The UV absorbance of the eluent was monitored at 215 nm. The fraction corresponding to the monoPEGylated mPEG$_{2k}$-Lys-GLP-1 peak at a retention volume of 1098.2 mL was collected (FIG. 11), buffer exchanged into deionized water, and lyophilized. Yield: 23 mg.

Figure 12:
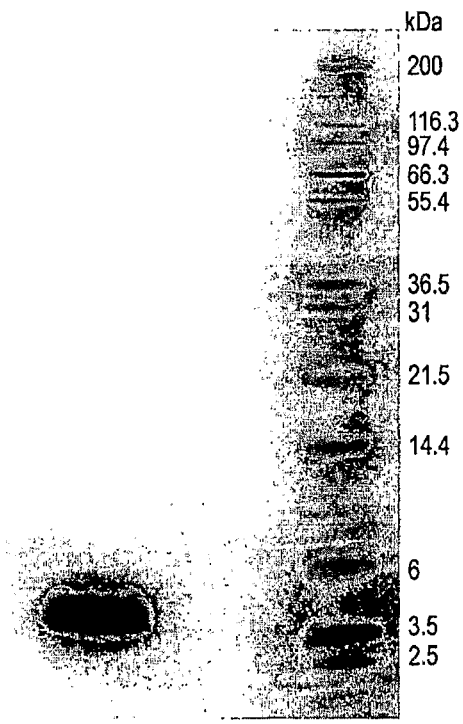
FIG. 12 corresponds to an SDS-PAGE analysis of purified mPEG$_{2k}$-Lys-GLP-1 (Example 7). Lane 1: MonoPEGylated mPEG$_{2k}$-Lys-GLP-1 after chromatographic purification. Lane 2: Invitrogen Mark 12 unstained standard.

The purified monoPEGylated mPEG$_{2k}$-Lys-GLP-1 was analyzed by SDS-PAGE (FIG. 12, Lane 1). Its molecular weight was determined by MALDI-TOF as 5499 Da.

The PEGylation site of the monoPEGylated mPEG$_{2k}$-Lys-GLP-1 conjugate at lysine residues (Lys$^{26}$ or Lys$^{34}$) and not at the N-terminus (H is) was confirmed by MALDI-TOF analysis following protease digestion of the conjugate using Endoproteinase LYS-C.

Example 8

In-Vivo Study in Mice to Examine the Blood-Glucose Lowering Effects of Illustrative GLP-1 Polymer Conjugates Male diabetic mice (BKS.Cg-+Lepr db/+Lepr db/01aHsd) were purchased from Harlan Laboratories, Ltd. (Jerusalem, Israel). The 8-9 week old animals (30-40 gm) were placed in mouse cages (two animals per cage), and allowed at least 48 hours of acclimatization before the start of the study.

The preparation of G2PEG2Fmoc$_{20k}$-N$^{ter}$-GLP-1 (Example 3), G2PEG2Fmoc$_{40k}$-N$^{ter}$-GLP-1 (Example 4), G2PEG2Fmoc$_{20k}$-Lys-GLP-1 (Example 5), and G2PEG2Fmoc$_{40k}$-Lys-GLP-1 (Example 6), is described in the preceding examples. Each compound was accurately weighed into a glass vial and dissolved in normal saline in order to prepare a concentration that would accommodate for the dose (based on GLP-1 equivalents) and the injection volume of 100 μL.

The study was divided into two phases: a feasibility phase and an evaluation phase.

In the feasibility phase, the feasibility of using diabetic db/db mice to test the effectiveness of GLP-1 was first evaluated. In carrying out the feasibility phase, several groups of mice were used wherein four mice were used in each group. Data on the baseline glucose levels were gathered for each mouse for 2-3 days prior to drug dosing. This was performed to identify any outliers in the group of animals. On the day of treatment (Day 0) each animal was weighed. A time 0 day blood sample (5 to 10 μl) was collected from the tail vein. The glucose level (mg/dL) was measured using a glucose analyzer. Each animal was then dosed subcutaneously (SC) below the skin on the back. The amount of test article and the dose (60 and 120 μg/mouse) administered was based on the average body weight of the animal, and the total volume of the dose did not exceed 10 mL/kg. The animals were then allowed to return into their cages. Blood samples of 5 to 10 μL (<0.5% of 2 mL blood volume for a 35 g mouse) were removed through a needle prick/capillary tube at the following time points: −3, −2, −1, 0, 0.04, 0.16, 0.33, 1.0, 1.16 days. Each collected blood sample was tested for its glucose level. At the end of the study, the animals were humanely euthanized by carbon-dioxide asphyxiation.

In the evaluation phase, the results from the feasibility phase were used to select the appropriate doses required to attain a sustained delivery of GLP-1 for a 3-5 day effect. In carrying out the evaluation phase, eight mice were used in each group. Data on the baseline glucose levels were gathered for each mouse three days prior to drug dosing. On the day of treatment (Day 0) each animal was weighed. A time 0 day blood sample (5 to 10 pt) was collected from the tail vein. The glucose level (mg/dL) was measured using a glucose analyzer. Each animal was then dosed subcutaneously (SC) below the skin on the back. The amount of test article administered was based on the average body weight of the animal, and the total volume of the dose did not exceed 10 mL/kg. The animals were then allowed to return into their cages. Blood samples of 5 to 10 μL (<0.5% of 2 mL blood volume for a 35 g mouse) were removed through a needle prick/capillary tube at the following time points: −3, −2, −1, 0, 0.04, 0.16, 0.33, 0.5, 1, 2, 3, 6 days. Each collected blood sample was for its glucose level. Food was withdrawn from the animals for the first four hours after dosing. At the end of the study, the animals were humanely euthanized by carbon-dioxide asphyxiation.

Table 4 below describes the test compounds and the dose for each group of animals.

TABLE 4

Test Compounds and Dose for Each Group of Animals

| Treatment | Lot or Reference Nos. | Number of mice per group | Dose (in μg) |
|---|---|---|---|
| Negative control (saline) | Baxter, lot C645028 | 8 | — |
| Positive control 2 (GLP-1) | American Peptide, lot T05128191 | 8 | 60, 120 |
| G2PEG2Fmoc$_{20K}$-Lys$_{(26\ or\ 34)}$-GLP1 | ZH 071805 | 8 | 420 |
| G2PEG2Fmoc$_{40K}$-Lys$_{(26\ or\ 34)}$-GLP1 | ZH 072305 | 8 | 420 |
| G2PEG2Fmoc$_{20K}$-N$^{ter}$-GLP1 | ZH 082405 ZH 092105 | 8 | 420 |
| G2PEG2Fmoc$_{40K}$-N$^{ter}$-GLP1 | ZH 082505 CP2F1 ZH 082505 CP2F2 | 8 | 420 |

Figure 13:
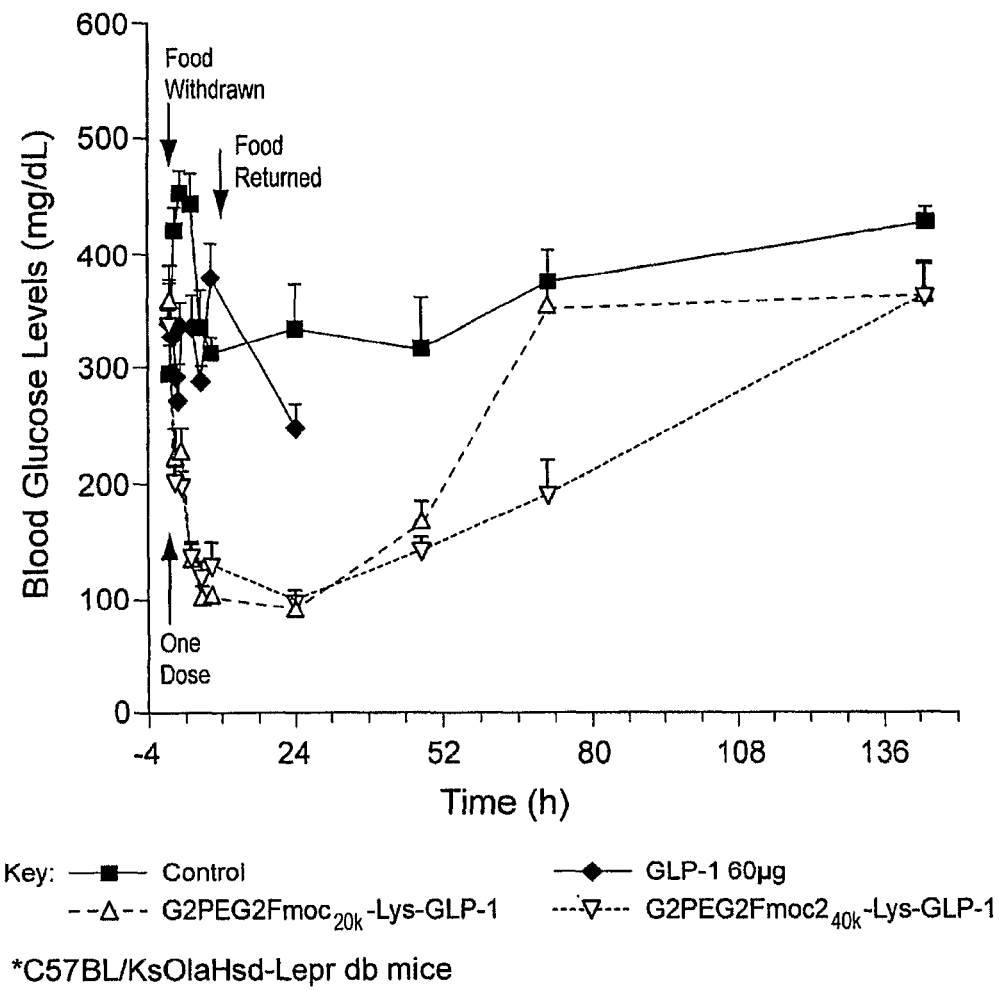
FIG. 13 is a plot demonstrating the comparative blood glucose-lowering effects over time of GLP-1, G2PEG2Fmoc$_{20k}$-Lys-GLP-1 conjugate and G2PEG2Fmoc$_{40k}$-Lys-GLP-1 conjugate when subcutaneously administered to db/db mice as described in Example 8.

The data from the study was collected and analyzed. It was noted that the animals tolerated the single subcutaneous dose. As illustrated in FIG. 13, the blood glucose-lowering effect of GLP-1 and each of the G2PEG2Fmoc$_{20K}$-Lys-GLP-1 (designated as "PEG20-Lys-GLP1" in the figure) and G2PEG2Fmoc$_{40K}$-Lys-GLP-1 (designated as "PEG40-Lys-GLP1" in the figure) conjugates is confirmed. It can be seen from the pharmacodynamic (PD) measurements that GLP-1 is cleared rapidly from the mouse, but that the GLP-1 conjugates release the peptide over a period of 3 to 4 days. That is to say, the exemplary GLP-1 degradable conjugates of the invention function somewhat like a molecular pump, releasing intact GLP-1 over time by in-vivo hydrolysis. The covalently attached hydrophilic polymer (i.e., PEG) functions not only to stabilize the GLP-1 in-vivo (i.e., by protecting the protein from enzymatic degradation), but also to extend its circulating half-life by slowly releasing the protein into the bloodstream over an extended period of 3 to 4 days. The 40 kilodalton PEG conjugate was also observed to have a small but extended PD effect when compared to the 20 kilodalton PEG conjugate.

The data from FIG. 13 suggest that: (a) GLP-1 is released into the mouse blood from the site of injection by diffusion and by hydrolysis from the PEGylated conjugate; and (b) the blood glucose-lowering activity of the lysine conjugated PEG-GLP1 may be due to the combination of the activity of the intact conjugates and the apparent in-vivo release of the peptide from the subject conjugates.

Figure 14:
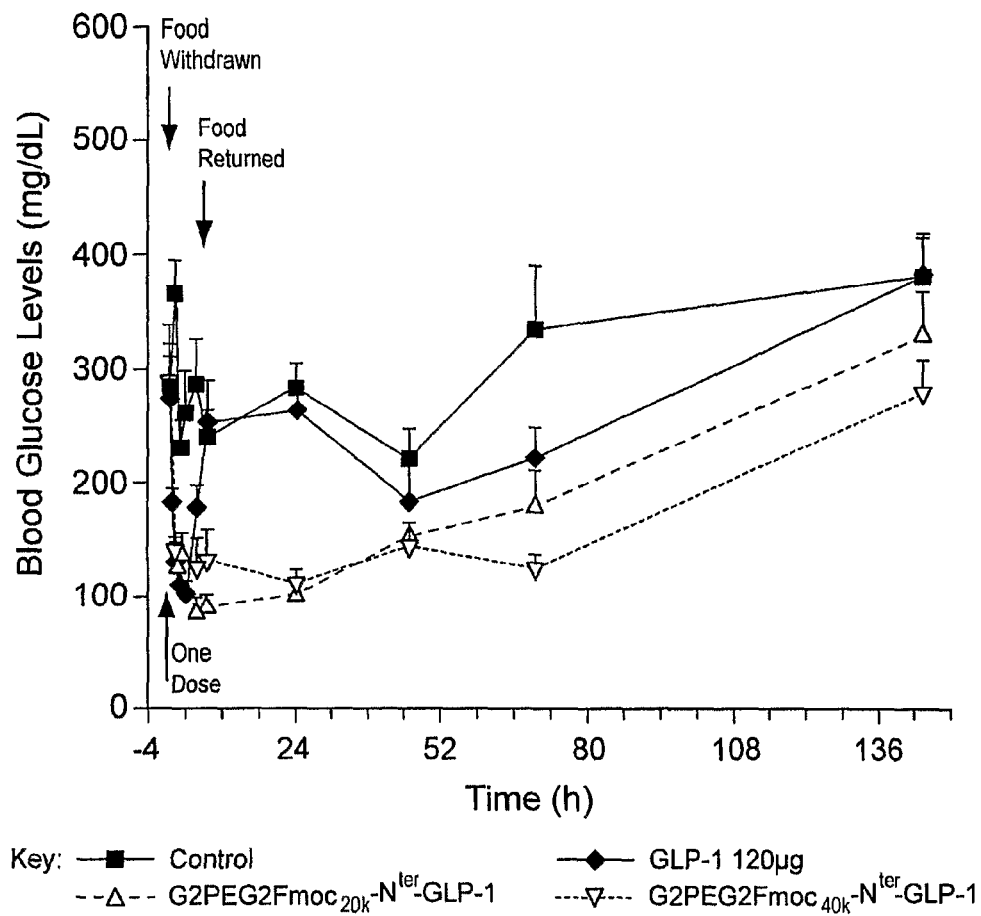
FIG. 14 is a plot demonstrating the comparative blood glucose-lowering effects over time of GLP-1, G2PEG2Fmoc$_{20k}$-N$^{ter}$-GLP-1 conjugate and G2PEG2Fmoc$_{40k}$-N$^{ter}$-GLP-1 conjugate when subcutaneously administered to db/db mice as described in Example 8.

FIG. 14 illustrates the blood glucose-lowering effect of GLP-1 and G2PEG2Fmoc$_{20K}$-N$^{ter}$-GLP-1 and G2PEG2Fmoc$_{40K}$-N$^{ter}$-GLP-1. It is evident from the pharmacodynamic (PD) measurements that GLP-1 is cleared rapidly from the mouse, but the PEG GLP-1 conjugates release the peptide over a period of 3 to 4 days. It is also observed that the PEG 40 kilodalton conjugate had a small but extended PD effect when compared to the PEG 20 kilodalton conjugate.

This set of data (FIG. 14) suggest that: (a) GLP-1 is released into the mouse blood from the site of injection by diffusion and by hydrolysis from the PEGylated conjugate; and (b) the histidine conjugated PEG-GLP 1 is not active, and the blood glucose-lowering activity observed is the result of release of the peptide from the conjugate.

This study demonstrates that one injection of PEGylated GLP-1 as described herein can be used to control diabetes over an extended period of more than 48 hours. This study also demonstrates the sustained release property of the G2PEG2Fmoc reagents when conjugated to GLP-1. This study also showed that GLP-1 can be PEGylated at the N-terminus to provide a product suitable for parenteral administration.

Example 9

PEGylation of GLP-1 with Branched mPEG-N-Hydroxysuccinimide Derivative, 40 kDa

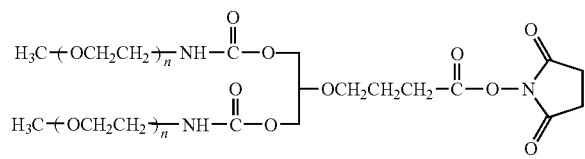

Branched mPEG-N-Hydroxysuccinimide Derivative, 40 kDa, ("mPEG2-NHS")

mPEG2-NHS, 40 kDa, stored at −20° C. under argon, is warmed to ambient temperature. A five-fold excess (relative to the amount of GLP-1 in a measured aliquot of the stock GLP-1 solution) of the warmed mPEG2-NHS is dissolved in 2 mM HCl to form a 10% reagent solution. The 10% reagent solution is quickly added to the aliquot of stock GLP-1 solution (1 mg/mL in sodium phosphate buffer, pH 7.0) and mixed well. After the addition of the PEG reagent, the pH of the reaction mixture is determined and adjusted to 7.0. To allow for coupling of the mPEG2-NHS to GLP-1 via an amide linkage, the reaction solution is placed on a Slow Speed Lab Rotator overnight to facilitate conjugation at room temperature. The reaction is quenched with Tris buffer. The conjugate solution is characterized by SEC-HPLC to determine the components of the conjugate mixture. Ion-exchange chromatography is used to purify the conjugates.

Glp-1 conjugates of varying molecular weights are similarly prepared using mPEG2-NHS reagents of differing molecular weights: 10 kDa, 15 kDA, 20 kDa, 30 kDa, 50 kDa, 60 kDa, etc.

Example 10

PEGylation of GLP-1 with Linear mPEG-Succinimidyl α-Methylbutanoate Derivative, 30 kDa

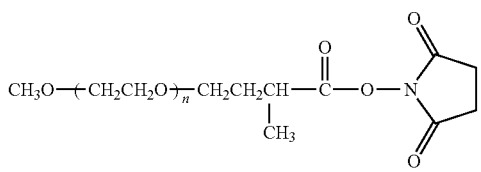

Linear mPEG-Succinimidyl α-Methylbutanoate Derivative, 30 kDa ("mPEG-SMB")

mPEG-SMB, 30 kDa, stored at −20° C. under argon, is warmed to ambient temperature. A ten-fold excess (relative to the amount of GLP-1 in a measured aliquot of the stock GLP-1 solution) of the warmed mPEG-SMB is dissolved in 2 mM HCl to form a 10% reagent solution. The 10% reagent solution is quickly added to the aliquot of stock GLP-1 solution (1 mg/mL in sodium phosphate buffer, pH 7.0) and mixed well. After the addition of the mPEG-SMB, the pH of the reaction mixture is determined and adjusted to 7.0. To allow for coupling of the mPEG-SMB to GLP-1 via an amide linkage, the reaction solution is placed on a Slow Speed Lab Rotator overnight to facilitate conjugation at room temperature. The reaction is quenched with Tris buffer.

The conjugate solution is characterized by SEC-HPLC. Ion-exchange is used to purify the conjugates.

Using this same approach, other conjugates are prepared using mPEG-SMB having other weight average molecular weights, e.g., 2 kD, 5 kD, 10 kD, 20 kD, 40 kD, etc.

Example 11

PEGylation of GLP-1 with mPEG-Piperidone, 20 kDa mPEG-Piperidone (mPEG-PIP) having a molecular weight of 20,000 Daltons is obtained from Nektar Therapeutics (Huntsville, Ala.). The basic structure of the polymeric reagent is provided below:

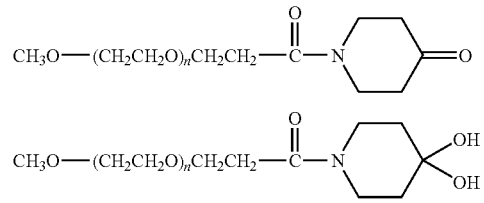

Linear mPEG-Piperidone Derivative, 20 kDa ("mPEG-PIP") Bottom structure corresponds to hydrated form mPEG-PIP, 20 kDa, stored at −20° C. under argon, is warmed to ambient temperature. A fifty to one hundred-fold excess (relative to the amount of GLP-1 in a measured aliquot of the stock GLP-1) of the warmed mPEG-PIP is dissolved in 10 mM sodium phosphate (pH 7.0) to form a 10% reagent solution. The 10% reagent solution is quickly added to the aliquot of stock GLP-1 solution (1 mg/mL in sodium phosphate buffer, pH 7.0) and mixed well. After the addition of the mPEG-PIP, the pH of the reaction mixture is determined and adjusted to 7.0, followed by mixing for thirty minutes. A reducing agent, sodium cyanoborohydride, is then added to make 13 mM NaCNBH$_3$, The reaction solution is placed on a Slow Speed Lab Rotator overnight to facilitate conjugation at room temperature. The reaction is quenched with Tris buffer.

The conjugate solution is characterized by SEC-HPLC. Ion-exchange is used to purify the conjugates.

Using this same approach, other conjugates can be prepared using mPEG-PIP having other weight average molecular weights, e.g., 2 kD, 5 kD, 10 kD, 30 kD, 40 kD, etc.

Example 12

PEGylation of GLP-1 with Linear mPEG-Butyraldehyde Derivative, 20 kDa

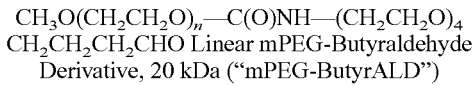
CH₃O(CH₂CH₂O)$_n$—C(O)NH—(CH₂CH₂O)₄CH₂CH₂CH₂CHO Linear mPEG-Butyraldehyde Derivative, 20 kDa ("mPEG-ButyrALD")

mPEG-ButyrALD, 20 kDa, stored at −20° C. under argon, is warmed to ambient temperature. A thirty-fold excess (relative to the amount of GLP-1 in a measured aliquot of the stock GLP-1) of the warmed mPEG-ButyrALD is dissolved in Milli-Q H₂O to form a 10% reagent solution. The 10% reagent solution is quickly added to the aliquot of stock GLP-1 solution (1 mg/mL in sodium phosphate buffer, pH 7.0) and mixed well. After the addition of the mPEG-ButryALD, the pH of the reaction mixture is determined and adjusted to 6.0, followed by mixing for thirty minutes. A reducing agent, sodium cyanoborohydride, is then added to make 9 mM NaCNBH₃. The reaction solution is placed on a Slow Speed Lab Rotator overnight to facilitate conjugation at room temperature. The reaction is quenched with Tris buffer. The conjugate solution is characterized by SEC-HPLC and anion-exchange chromatography.

Using this same approach, other conjugates can be prepared using mPEG-ButyrALD having other weight average molecular weights, e.g., 2 kD, 5 kD, 10 kD, 30 kD, 40 kD, etc.

Example 13

PEGylation of GLP-1 with Branched mPEG-Butyraldehyde Derivative, 40 kDa

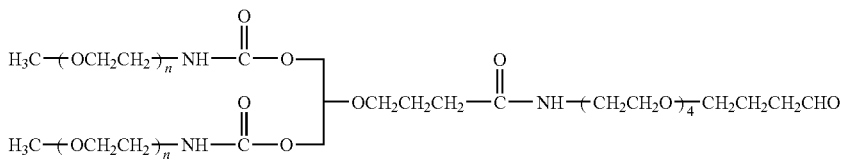

Branched mPEG-Butyraldehyde Derivative, 40 kDa ("mPEG2-ButyrALD")

mPEG2-ButyrALD, 40 kDa, stored at −20° C. under argon, is warmed to ambient temperature. A thirty-fold excess (relative to the amount of GLP-1 in a measured aliquot of the stock GLP-1) of the warmed mPEG2-ButryALD was dissolved in Milli-Q H₂O to form a 10% reagent solution. The 10% reagent solution is quickly added to the aliquot of stock GLP-1 solution (1 mg/mL in sodium phosphate buffer, pH 7.0) and mixed well. After the addition of the mPEG2-ButryALD, the pH of the reaction mixture is determined and adjusted to 6.0 using conventional techniques, followed by mixing for thirty minutes. A reducing agent, sodium cyanoborohydride is then added to make 9 mM NaCNBH₃. The reaction solution is placed on a Slow Speed Lab Rotator overnight to facilitate conjugation at room temperature. The reaction is quenched with Tris buffer.

The conjugate solution is characterized by SEC-HPLC and ion-exchange chromatography method.

Using this same approach, other conjugates can be prepared using mPEG2-ButyrALD having other weight average molecular weights, e.g., 10 kD, 15 kD, 20 kD, 30 kD, 50 kD, 60 kD, etc.

Example 14

PEGylation of GLP-1 with mPEG-SBA mPEG-Succinimidyl butanoate having a molecular weight of 20,000 Daltons is obtained from Nektar Therapeutics, (Huntsville, Ala.). The basic structure of the polymer reagent is provided below:

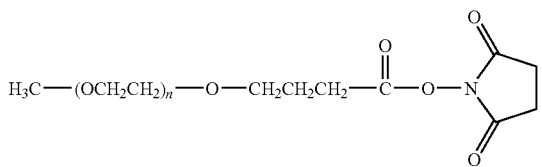

GLP-1 is dissolved in aqueous solution (1 mg/mL phosphate buffered solution). To this solution is then added a 1.5 to 10-fold molar excess of mPEG-SBA. After the addition of the mPEG-SBA, the pH of the reaction mixture is determined and adjusted to 7.0 to 7.5. The resulting mixture is stirred at room temperature for several hours.

The reaction mixture is analyzed by SDS-PAGE to determine the degree of PEGylation of the protein.

Example 15

Conjugation of Cysteine-Inserted GLP-1 with mPEG-MAL, 20K

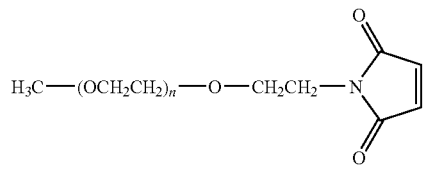

mPEG MAL, 20K

GLP-1 is inserted with one or more cysteine residues according as described in U.S. Patent Application Ser. Nos. 60/346,474 and 60/405,097. Illustrative cysteine-modified GLP-1 compounds are described in WO 2004/093823.

mPEG-MAL, 20K, stored at −20° C. under argon, is warmed to ambient temperature. A five- to twenty-fold excess of the warmed mPEG-MAL, 20K, is dissolved in deionized water to make a 10% mPEG MAL solution. The mPEG MAL solution is quickly added to an aliquot of stock cysteine-modified GLP-1 solution (1 mg/mL in 50 mM HEPES, pH 7.0) and is mixed well. After one hour of reaction at room temperature, the reaction vial is transferred to the cold room and the reaction is allowed to proceed overnight at 4° C. on Rotomix (slow speed, Thermolyne).

The conjugate mixture is purified using gel filtration chromatography. A size exclusion chromatography method is developed for analyzing the reaction mixtures, and the final products. SDS-PAGE analysis is also used for the characterization of the samples.

Example 16

Conjugation of GLP-1 with mPEG-MAL, 30K

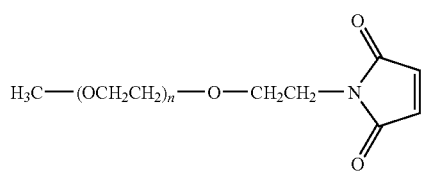

mPEG MAL, 30K

Cysteine-modified GLP-1 is obtained as described in Example 16 above.

mPEG-MAL, 30K, stored at −20° C. under argon, is warmed to ambient temperature. A five- to twenty-fold excess of the warmed mPEG-MAL, 30K, is dissolved in deionized water to make a 10% mPEG MAL solution. The mPEG MAL solution is quickly added to an aliquot of stock cysteine-inserted GLP-1 solution (1 mg/mL in 50 mM HEPES, pH 7.0) and is mixed well. After one hour of reaction at room temperature, the reaction vial is transferred to the cold room and the reaction is allowed to proceed overnight at 4° C. on Rotomix (slow speed, Thermolyne).

The conjugate mixture is purified using gel filtration chromatography. A size exclusion chromatography method is developed for analyzing the reaction mixtures, and the final products. SDS-PAGE analysis is also used for the characterization of the samples.

Example 17

PEGylation of GLP-1 with mPEG-Succinimidyl Benzamid-Carbonate 20 kDa (MPEG-SBC 20 kDa) in an Aqueous Reaction

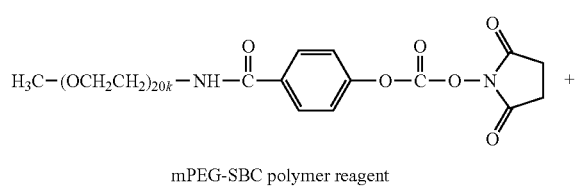

mPEG-SBC polymer reagent

+

-continued

GLP-1 ⟶

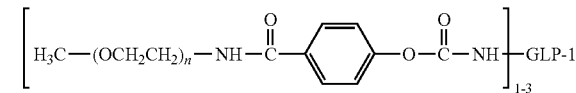

mPEG-SBC 20 kDa, available from Nektar Therapeutics (Huntsville, Ala.), stored at −20° C. under argon, is warmed to ambient temperature. The reaction is performed at room temperature. The calculated quantity of the warmed mPEG-SBC 20 kDa (414 mg, to obtain an 8-fold molar excess of mPEG-SBC 20 kDa based upon absolute GLP-1 content) is weighed into a 5 mL glass vial. 1.1 mL of DMSO is added to PEG, and it is heated in a 40° C. water bath until the PEG is dissolved. It is then allowed to equilibrate back to room temperature. A 2.0 mL aliquot of a 4.5 mg/mL solution of GLP-1 prepared in phosphate buffered saline, PBS, pH 7.4) is added to 10 mL glass vial and the volume brought to 4.5 mL with additional PBS. The protein is stirred using a magnetic stirrer at a moderate speed. The PEG is added to the protein via a syringe infusion at a rate of approximately 1 mL/min: The reaction is allowed to proceed for 10 minutes. It is then quenched by dropping the pH to 5.5 with 1 M HCl.

The conjugate solution is analyzed by SDS-PAGE and RP-HPLC.

Example 18

PEGylation of GLP-1 with MPEG-Succinimidyl Benzamid-Carbonate 30 kDa (MPEG-SBC 30 kDa) in an Aqueous Reaction GLP-1 is PEGylated as described in Example 18 above with the exception that the PEG reagent employed possesses a molecular weight of 30 kDa.

Example 19

PEGylation of GLP-1 with MPEG-Succinimidyl Phenyl-Carbonate 20 KDa (MPEG-SPC 20 kDa) in Aqueous Reaction

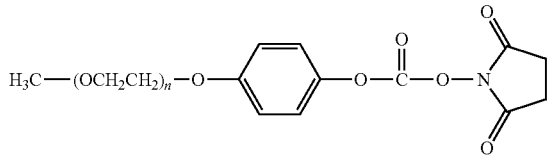

'SPC' polymer reagent mPEG-SPC 20 kDa, available from Nektar Therapeutics (Huntsville, Ala.), stored at −20° C. under argon, is warmed to ambient temperature. The reaction is performed at room temperature. An absolute 8-fold molar excess of mPEG-SPC reagent is used, based upon absolute peptide content. The PEG reagent is weighed into a 5 mL glass vial containing a magnetic stirrer bar. A 2.0 mL aliquot of a 4.5 mg/mL solution of GLP-1 prepared in phosphate buffered saline, PBS, pH 7.4 is added and the volume brought to 4.5 mL with additional PBS. The mixture is stirred at maximum speed using a magnetic stirrer until the PEG is fully dissolved. The stirring speed is reduced to 50% and the reaction is allowed to proceed to formation of conjugate product. The pH of the conjugate solution at the end of the reaction is measured and further acidified by addition of 0.1 M HCl, if necessary, to bring the pH of the final solution to about 5.5.

The conjugate solution is then analyzed by SDS-PAGE and RP-HPLC(C18) to determine the extent of reaction (i.e., whether the reaction has gone to completion).

Additional reactions, conducted as described above, are carried out with (i) mPEG-SPC 30 kDa, and (ii) mPEG-SPC 40 kDa, available from Nektar Therapeutics, Huntsville, Ala.

Example 20

In Vitro Activity Assay of PEG-Glp-1 Conjugates

The bioactivity of the conjugates described in Examples 3-7 and 9-20 is tested using an in-vitro activity assay as described in Zlokarnik, et al. (1998), Science, 279:84-88.

HEK-293 cells expressing the human GLP-1 receptor, using the PanVera LLC CRE-BLAM system, are seeded at 20,000 to 40,000 cells/well/100 µl DMEM medium with 10% FBS into a poly-d-lysine coated 96 well plate. The day after seeding, the medium is flicked off and 80 µl plasma-free DMEM medium is added. On the third day after seeding, 20 µl of plasma-free DMEM medium with 0.5% BSA containing different concentrations of PEG-GLP-1 conjugate is added to each well to generate a dose-response curve. Generally, fourteen dilutions containing from 3 nanomolar to 30 nanomolar PEG-GLP-1 conjugate are used to generate a dose response curve from which EC50 values can be determined. After 5 hours incubation, with the PEG-GLP-1 conjugate, 20 µl of β-lactamase substrate (CCF2/AM, Pan Vera LLC) is added and incubation is continued for one hour at which time fluorescence is determined on a fluorimeter.

Example 21

In vitro Release Profile of G2PEG2Fmoc$_{20K}$-N$^{ter}$-GLP-1

The in vitro release profile of G2PEG2Fmoc$_{20K}$-N$^{ter}$-GLP-1 was determined.

G2PEG2Fmoc$_{20K}$-N$^{ter}$-GLP-1 (in the form of mono-PEGylated GLP-1) was prepared as described in Example 3 and was used to evaluate the release of GLP-1 under hydrolysis conditions.

The conditions used to determine the in vitro release profile G2PEG2Fmoc$_{20K}$-N$^{ter}$-GLP-1 included: 2 mg/mL G2PEG2Fmoc$_{20K}$-N$^{ter}$-GLP-1 (monoPEGylated GLP-1 form) in phosphate-buffered saline, pH 7.4, 37° C. with samples taken at various time points and tested for the presence of "free" or unconjugated GLP-1. The release of GLP-1 was monitored by reverse phase HPLC at 215 nm.

Figure 15:
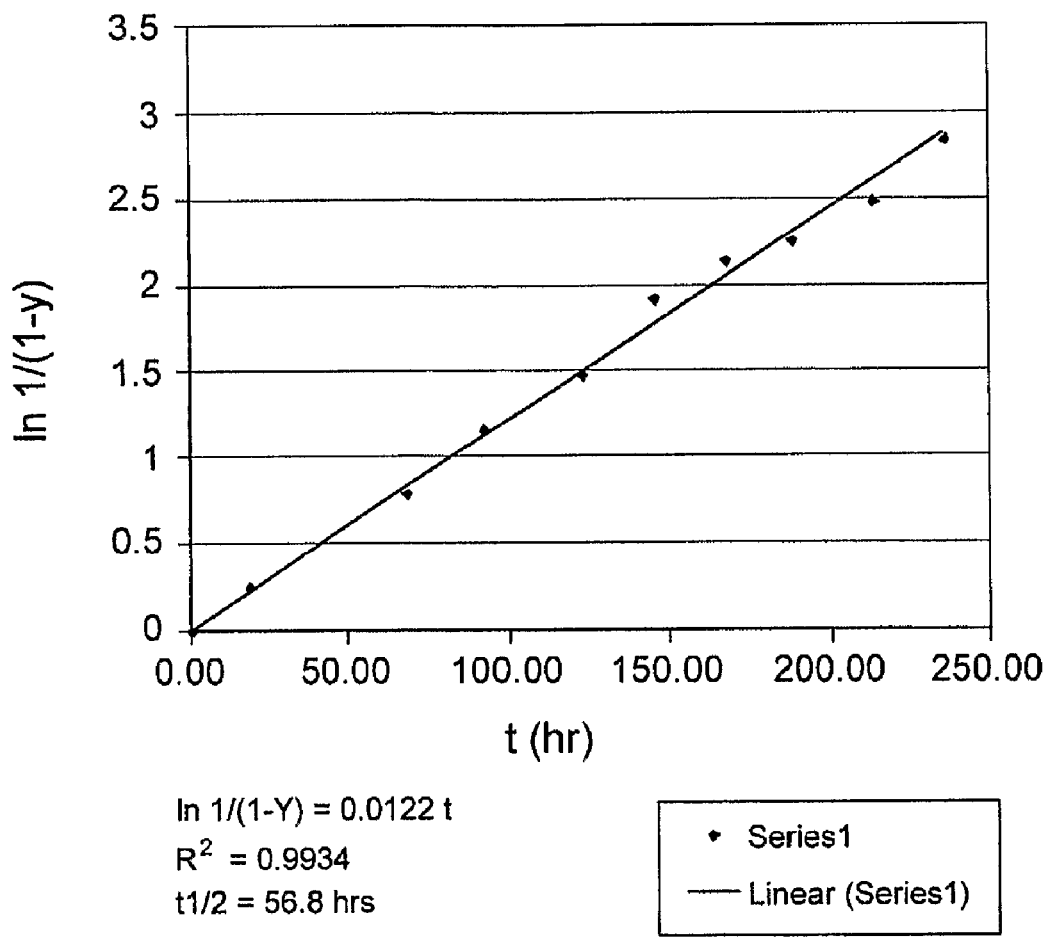
FIG. 15 is a plot showing the in vitro release profile of G2PEG2Fmoc$_{20k}$-N$^{ter}$-GLP-1 as described in Example 21.

FIG. 15 sets forth the results of the experiment is graph form, where Y=A$_t$/A$_{max}$ (A$_t$ is HPLC peak area of released GLP-1 at time of t (hr) and A$_{max}$ is HPLC peak area of GLP-1 reached its maximum release). Because the reaction kinetics represent a first order reaction due to the linearity of the plot, it can be concluded that ln 1/(1−Y)=kt, where k is the slope, t$_{1/2}$=ln 2/k. Based upon extrapolation of the data, the conjugate was determined to possess a hydrolysis half-life of 56.8 hours.

Example 22

Synthesis and Purification of mPEG$_{2k}$-O(CH$_2$)$_4$—N$^{ter}$-GLP-1

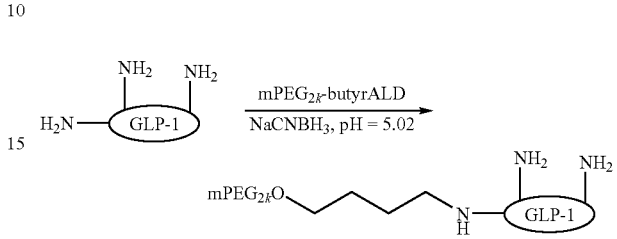

GLP-1 (43.2 mg, 13.0 µmol) was dissolved in a sodium acetate buffer solution (20 mL, pH=5.02) and CH3CN (1000 µL). mPEG2k-butyrALD (259.2 mg, 130 µmol) was added with stirring and the reaction was maintained at room temperature for 20 min. Solid NaCNBH3 (~5-8 mg, 7-10 eq) was then added and the reduction reaction was monitored by analytical HPLC. After allowing to react overnight (16 h), the product was purified by FPLC (fast protein liquid chromatography) using an ÄKTA™ Basic System (Pharmacia) and a gradient of 36.3-56% CH3CN in 0.1% TFA Milli-Q water in 0.76 CV (column volume). Fractions corresponding to mono mPEG2k-O(CH2)-4-Nter-GLP-1 were collected. The product was lyophilized and obtained as a white powder. Yield: 64.5 mg.

Example 23

Synthesis, Purification and Hydrolysis of mPEG$_{5K}$-OC$_6$H$_4$—OCO—N$^{ter}$-GLP-1 (mPEG$_{5k}$-SPC—N$^{ter}$-GLP-1)

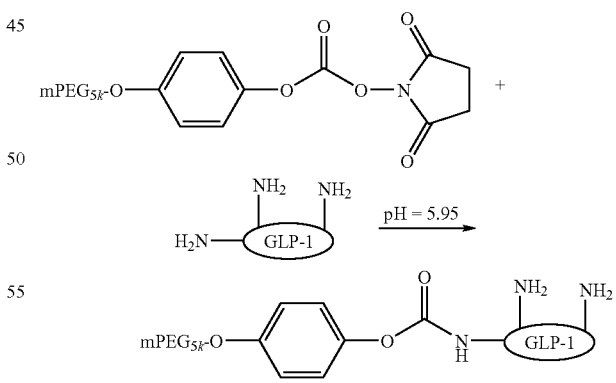

GLP-1 (43.6 mg, 13.2 µmol) was dissolved in a sodium acetate buffer solution (28 mL, pH=5.95) at room temperature. mPEG$_{5K}$-SPC (556 mg, 111 µmol) was added in several different portions while the reaction progress was monitored by analytical HPLC. After the maximum peak area of product was reached, the product mixture was purified immediately using an ÄKTA™ Basic System (Pharmacia) with a gradient of 37.8-60% CH₃CN in 0.1% TFA Milli-Q water in 5 CV. The fractions corresponding to mono mPEG$_{5k}$-SPC—N$^{ter}$-GLP-1 were collected (14 mL/fraction), and the product was lyophilized and obtained as a white powder. Yield: 75 mg.

Hydrolysis:

The mPEG$_{5k}$-SPC—N$^{ter}$-GLP-1 was dissolved in PBS buffer (pH=7.2) and warmed to 37° C. The hydrolysis was monitored by analytical HPLC. The half-life was determined to be about 8 hrs according to MS detector. The PEGylated GLP-1 was completely hydrolyzed after 3 days, leaving 6% of unknown product. Although native GLP-1 was released upon hydrolysis, the major hydrolysis product was not free GLP-1 but rather a His-carbamate compound as shown below. This result was further confirmed by LC-MS.

A similar phenomenon was observed for the counterpart N-terminal GLP-1 conjugate prepared by reaction with an mPEG-SBC reagent. When attempting to further purify the conjugate, under the conditions utilized, the conjugate was found to be extremely labile. The conjugate rapidly hydrolyzed to native GLP-1 and a GLP-1 derivative resulting from an intramolecular ring closure reaction due to reaction at the carbamate carbonyl by the imidazolyl nitrogen of the N-terminal histidine of GLP-1. The modified GLP-1 thereby released is shown below. Further purification was not pursued.

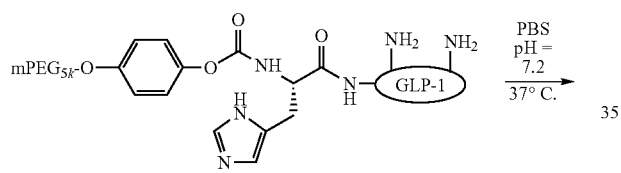

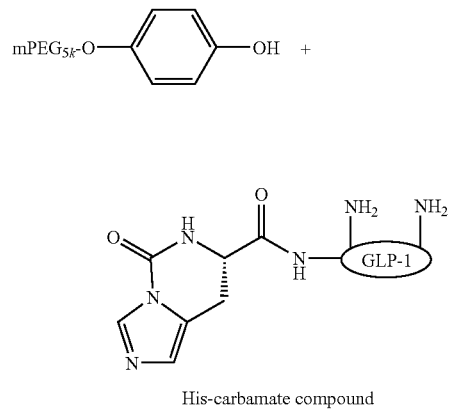

His-carbamate compound

Example 24

Preparation of an Exemplary GLP-1-Polymer Conjugate Having a Releasable PEG Moiety Attached to GLP-1

Preparation of PEG2-CAC-Fmoc$_{4k}$-N$^{ter}$-GLP-1

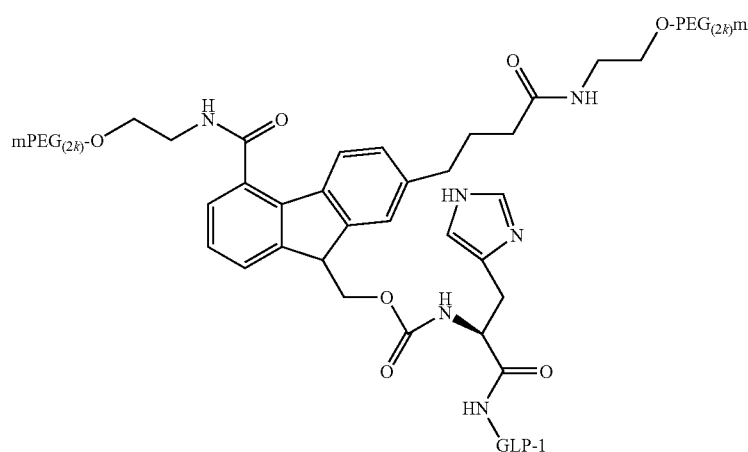

PEG2-CAC-Fmoc$_{4k}$-N$^{ter}$-GLP-1

An illustrative polymeric reagent, PEG2-CAC-Fmoc$_{4k}$-BTC (structure provided below), was covalently attached to the N-terminus of GLP-1 to provide a prodrug form of the protein wherein the PEG-moiety is releasably attached. The two-arm nature of the polymeric reagent provides increased stability to the GLP-1 moiety subsequent to administration, to thereby provide a sustained release formulation whereby GLP-1 is released from the conjugate via hydrolysis to provide the native or unmodified GLP-1 precursor. The structure of PEG2-CAC-Fmoc4k-Nter-GLP-1 is provided above (in the structure, "GLP-1" represents a residue of GLP-1 corresponding to amino acids 8-36; the N-terminal histidine of GLP-1 is shown explicitly to illustrate conjugation at the alpha amine rather than of the imidazole ring).

Performance column media (Amersham) with a flow rate of 30 mL/min. The crude solution was first diluted by addition of sodium acetate buffer at pH 4.30, and was then loaded onto the column. The UV absorbance of the eluent was monitored at 215 nm. The fraction corresponding to the PEG2-CAC-Fmoc$_{4k}$-N$^{ter}$-GLP-1 (monoPEGylated form) peak was collected. Purification of the remaining crude product was conducted, and the fractions corresponding to the PEG2-CAC-Fmoc$_{4k}$-N$^{ter}$-GLP-1 (monoPEGylated form) peak were combined, analyzed by reversed phase HPLC, and concentrated by ultrafiltration. The concentrated solution was buffer exchanged into 20 mM sodium citrate buffer at pH 4.3. The solution was then lyophilized. Yield: 163.2 mg.

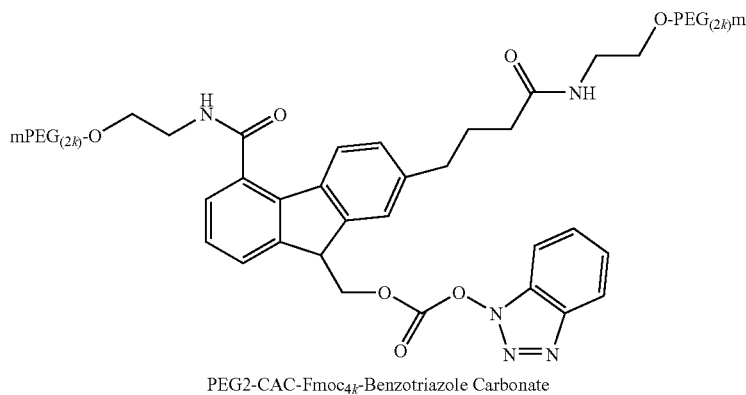

PEG2-CAC-Fmoc$_{4k}$-Benzotriazole Carbonate

PEG2-CAC-Fmoc$_{4k}$-BTC (BTC=benzotriazole carbonate) was prepared according to the methods described in U.S. patent application Ser. No. 11/454,971, filed on Jun. 16, 2006, to which the instant application claims priority, and the contents of which have been incorporated herein by reference.

A solution of 400 mg GLP-1 ($1.1146 \times 10^{-4}$ mol) in 100 mL of 20 mM sodium acetate buffer at pH 5.50 was prepared, followed by slow addition over 5 minutes with stirring of 1.737 g of PEG2-CAC-Fmoc$_{4k}$-BTC ($3.9013 \times 10^{-4}$ mol), which was freshly dissolved in 17 mL of 2 mM HCl. The solution was allowed to stir for 13 hours at room temperature, thereby allowing for the formation of PEG2-CAC-Fmoc$_{4k}$-N$^{ter}$-GLP-1, a PEGylated GLP-1 conjugate. The reaction mixture was quenched by addition of 1 mL of 1M glycine. The solution pH was adjusted to 7.0 by 0.5 N NaOH. The reaction mixture was allowed to stir at room temperature for another 2 hours. The quenched reaction mixture was then acidified to pH 4.0 by addition of 20 mM HAc. The reaction was monitored by reversed phase HPLC, using a 100 mm×4.6 mm ID Onyx monolithic C8 column with Mesopores of 130 Å and Macropores of 2 μm, available from Phenomenex. A mobile phase of 0.1% TFA in deionized water (solution C) and 0.1% TFA in acetonitrile (solution D) at 25° C. was employed using a linear gradient from 35% B to 55% B over 4 minutes.

To obtain the PEG2-CAC-Fmoc$_{4k}$-N$^{ter}$-GLP-1 in monoPEGylated form, the acidified reaction mixture (125 mL) was divided into 3 aliquots, and each aliquot was individually purified by cation exchange chromatography on an ÄKTA Basic System using a mobile phase of 20 mM sodium acetate buffer at pH 4.30 (Solution A) and 20 mM sodium acetate buffer with 1 M NaCl at pH 4.30 (Solution B). The column utilized was a Vantage L Laboratory Column VL (Millipore) packed with 160 mL column volume of SP Sepharose High The purified PEG2-CAC-Fmoc$_{4k}$-N$^{ter}$-GLP-1 was analyzed by SDS-PAGE. Its molecular weight was determined by MALDI-TOF as 7831.6 Da. The cleavable nature of the G2PEG2Fmoc$_{20k}$-N$^{ter}$-GLP-1 conjugate in aqueous media [1:2 v/v mixture of 20 mM sodium citrate buffer at pH 4.30 with 200 mM tris(hydroxymethyl)aminomethane (Tris) solution, incubated 16 hours at 37° C.] was also investigated by reversed phase HPLC, from which the complete release of GLP-1 from the conjugate was observed.

Example 25

Pharmacodynamic Evaluation of a Modified GLP-1 agonist, PEG2-CAC-Fmoc$_{4k}$-N$^{ter}$-GLP-1, in a Diabetic Mouse Model The objective of the study was to demonstrate the pharmacological activity of an illustrative GLP-1 conjugate, PEG2-CAC-Fmoc$_{4k}$-N$^{ter}$-GLP-1, administered intratracheally (IT) in the mouse.

Figure 16:
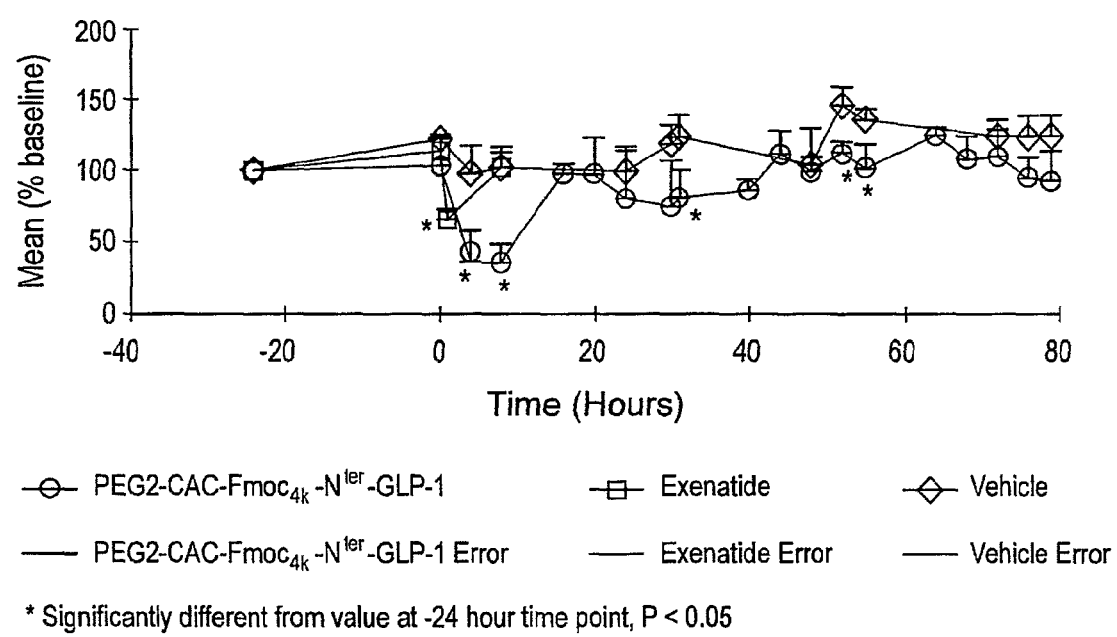
FIG. 16 is a plot of group mean blood glucose concentrations in mice administered exenatide (subcutaneous), PEG2-CAC-Fmoc$_{4k}$-N$^{ter}$-GLP-1 (intratracheal) or vehicle (intratracheal). Blood glucose concentrations are expressed as % of value measured at 24 hours pre-dose as described in Example 25.

A male diabetic mouse (BKS.Cg-+Lepr db/+Lepr db/01 aHsd) model was used in the study. The test system included 21 male diabetic mice (BKS.Cg-+Lepr db/+Lepr db/01 aHsd) approximately 8-9 weeks of age (Harlan Labs). See Table 5. The mice were anesthetized and then suspended vertically by their upper incisors. Approaching the suspended animal from the dorsal position, a 1 mL syringe fitted with a gavage needle was inserted orally into the mouse and descended into the trachea just above the carina. The dose was instilled into the lungs and the gavage needle was then immediately removed. Exenatide was administered by subcutaneous (SC) injection using a 20 G 1 inch 1 mL tuberculin syringe. Blood samples of approximately 0.07 mL were collected from the tail vein at each time point. These samples were tested for concentrations of glucose. The glucose measurement was made in duplicate with Glucometer Elite (Bayer Corp., Elkart, Ind.) glucose monitors. The upper limit of quantitation (ULOQ) of these glucometers is 600 mg/dl. This value (600 mg/dl) was used for calculation of descriptive statistics when the ULOQ was exceeded. Group mean blood glucose concentrations, expressed as % of baseline, are given in FIG. 16. These values were calculated for each individual animal using its 24-hour pre-dose blood glucose measurement as baseline. Statistical evaluation was made with a 2-tailed t-test at a P value of 0.05 and compared group means of treatment and vehicle groups at corresponding time points. In the absence of a corresponding vehicle time point for the 1 hour exenatide measurement, the 4 hour vehicle measurement was used for statistical comparison. Selected time points of PEG2-CAC-Fmoc$_{4k}$-N$^{ter}$-GLP-1 and exenatide-treated groups were also compared to their respective T=0 values.

TABLE 5

Study Design

| Group No. | Control/Test Article | Route of Administration | Number of Animals/ Gender | Total Dose of Test Article (μg/mouse) | No. of Dosing Days |
|---|---|---|---|---|---|
| 1 | PEG2-CAC-Fmoc$_{4k}$-N$^{ter}$-GLP-1 | IT | 12 M | 1500 | 1 |
| 2 | Vehicle | IT | 6 M | NA | 1 |
| 3 | Exenatide | SC | 3 M | 0.1 | 1 |

The objective of this study, i.e., to demonstrate pharmacological activity of an illustrative releasable GLP-1 conjugate, when administered intratracheally (IT) in the mouse, was achieved.

Mice were administered PEG2-CAC-Fmoc$_{4k}$-N$^{ter}$-GLP-1 or vehicle intratracheally and were tested for blood glucose concentrations at various time points post-administration. Exenatide administered SC was used as a positive control.

A significant reduction in blood glucose was observed at the 1 hour time point in the group administered exenatide. Blood glucose had returned to baseline by the next time point (8 hrs).

PEG2-CAC-Fmoc$_{4k}$-N$^{ter}$-GLP-1 caused a substantial reduction in blood glucose at 4 and 8 hours after administration. The magnitude of the glucose suppression was greater than that observed following administration of exenatide. This reduction was statistically significant both when compared to the T=0 hour pre-dose measurement and to the values for the vehicle group at the corresponding time point.

Intact PEG2-CAC-Fmoc$_{4k}$-N$^{ter}$-GLP-1 is thought not to have pharmacological activity. This is presumably due to the interference of the N-terminal PEG with the interaction of the GLP-1 ligand to its receptor. The observation of in vivo pharmacological activity and the occurrence of the activity maximum 8 hours after administration are consistent with in vivo cleavage of PEG2-CAC-Fmoc$_{4k}$-N$^{ter}$-GLP-1 and release of active GLP-1.

At 3 other time points (31, 52, and 55 hours), a statistically significant difference was observed between the PEG2-CAC-Fmoc$_{4k}$-N$^{ter}$-GLP-1 and vehicle groups. The magnitude of the difference was considerably smaller than that observed at 4 and 8 hours. In contrast to the reductions observed at 4 and 8 hours, the glucose values at these 3 time points were not significantly different from the values at T=0. The biological significance of this observation will need to be further evaluated but a delayed cleavage of residual 4K-FMOC GLP-1 in the lung could theoretically result in delayed glucose suppression.

No adverse effect attributed to compound was observed in these studies. The one mouse death (animal 1-8) was attributed to the administration process.

In sum, the results of this experiment indicate that the intratracheal administration of PEG2-CAC-Fmoc$_{4k}$-N$^{ter}$-GLP-1 resulted in a statistically significant, profound and prolonged suppression of blood glucose in a male diabetic mouse (BKS.Cg-+Lepr db/+Lepr db/01 aHsd) model.

Example 26

Pharmacodynamic Evaluation of a Modified GLP-1 agonist, mPEGSPC$_{5k}$-N$^{ter}$-GLP-1, in a Diabetic Mouse Model The objective of this study was to demonstrate the pharmacological activity of the exemplary, releasable GLP-1 conjugate, mPEGSPC$_{5k}$-N$^{ter}$-GLP-1, when administered intratracheally (IT) in the mouse.

A male diabetic mouse (BKS.Cg-+Lepr db/+Lepr db/01 aHsd) model was used in the study. The conjugate administered, mPEGSPC$_{5k}$-N$^{ter}$-GLP-1, is cleavable and was expected to release active GLP-1 in vivo. The released GLP-1 moiety was expected to have an approximately 200-fold reduced activity due to a residual carbonyl residue at the N-terminus (See, e.g., Example 23 above).

The test system included 18 male diabetic mice (BKS.Cg-+ Lepr db/+Lepr db/01aHsd) approximately 8-9 weeks of age (Harlan Labs). The mice were anesthetized and then suspended vertically by their upper incisors. Approaching the suspended animal from the dorsal position, a 1 mL syringe fitted with a gavage needle was inserted orally into the mouse and descended into the trachea just above the carina. The dose was instilled into the lungs and the gavage needle was then immediately removed. Exenatide was administered by subcutaneous (SC) injection using a 20 G 1 inch 1 mL tuberculin syringe. Blood samples of approximately 0.07 mL were collected from the tail vein at each time point. These samples were tested for concentrations of glucose. The glucose measurement was made in duplicate with Glucometer Elite (Bayer Corp., Elkart, Ind.) glucose monitors. The upper limit of quantitation (ULOQ) of these glucometers is 600 mg/dl. This value (600 mg/dl) was used for calculation of descriptive statistics when the ULOQ was exceeded. Group mean blood glucose concentrations (mg/dl) are given in FIG. 17. Statistical evaluation was made with a 2-tailed t-test at a P value of 0.05 and compared selected time points to T=0 value for that treatment group.

TABLE 6

Study Design

| Group No. | Control/Test Article | Route of Administration | Number of Animals/ Gender | Total Dose of Test Article (μg/mouse) | No. of Dosing Days |
|---|---|---|---|---|---|
| 1 | mPEGSPC$_{5k}$-N$^{ter}$-GLP-1 | IT | 9 M | 1000 | 1 |
| 2 | Vehicle | IT | 6 M | NA | 1 |
| 3 | Exenatide | SC | 3 M | 0.1 | 1 |

The objective of this study, to demonstrate pharmacological activity of the PEGylated and releasable GLP-1 conjugate, mPEGSPC$_{5k}$-N$^{ter}$-GLP-1, when administered intratracheally (IT) in the mouse, was achieved.

Mice were administered mPEGSPC$_{5k}$-N$^{ter}$-GLP-1 or vehicle intratracheally and were tested for blood glucose and plasma insulin concentrations at various time points post administration. Exenatide administered SC was used as a positive control.

Figure 17:
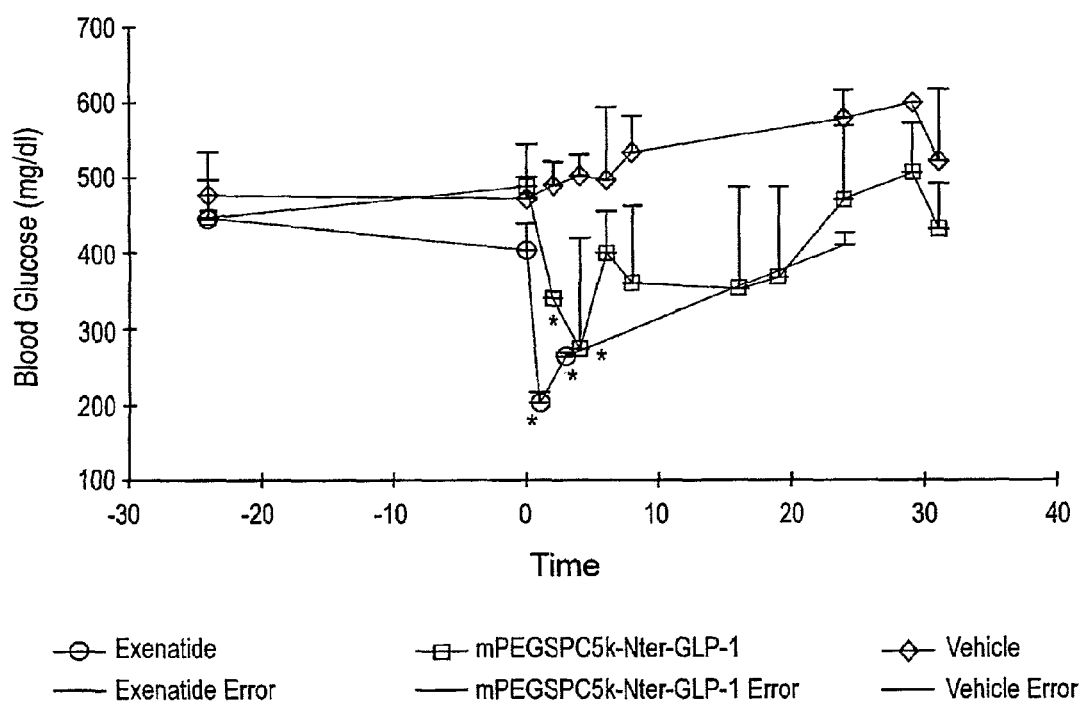
FIG. 17 is a plot of group mean blood glucose concentrations in mice administered exenatide (subcutaneous), mPEGSPC$_{5k}$-N$^{ter}$-GLP-1 (intratracheal) or vehicle (intratracheal) as described in Example 26.

A significant reduction in blood glucose was observed at the 1 and 3 hour time points in the group administered exenatide. Blood glucose had returned to baseline by the next time point (24 hrs).

mPEGSPC$_{5k}$-N$^{ter}$-GLP-1 caused an overall reduction in blood glucose profile from the 2 hour time point to the 31 hour (last) time point when compared to the vehicle (FIG. 17). When group means at individual time points were compared to pre-dose values, glucose suppression at 2 and 4 hours reached statistical significance. This was true whether the −24 or 0 hour pre-dose values were used for the comparison. Glucose reduction at these time points did not reach significance when compared to the values for the vehicle group at the corresponding time point. It should be noted that there were only 3 mice per non pre-dose time point and that there is considerable variation between individual mouse values.

Intact mPEGSPC$_{5k}$-N$^{ter}$-GLP-1 is assumed not to have pharmacological activity. This is presumed because of the interference of the N-terminal PEG with the interaction of the GLP-1 ligand to its receptor. The released GLP-1 moiety is expected to have a low level of pharmacological activity when compared to native GLP-1 due to a residual carbonyl moiety at the N-terminus (which would likely also interfere with receptor-ligand binding). This lower intrinsic activity of the cleavage product may have contributed to the less pronounced pharmacological effect of the mPEGSPC$_{5k}$-N$^{ter}$-GLP-1 relative to that of PEG2-CAC-Fmoc$_{4k}$-N$^{ter}$-GLP-1. The observation of in vivo pharmacological activity and the occurrence of the activity maximum 4 hours after administration are consistent with in vivo cleavage of mPEGSPC$_{5k}$-N$^{ter}$-GLP-1 and release of a form of active GLP-1.

Though it does not reach statistical significance at individual time points, IT administration of mPEGSPC$_{5k}$-N$^{ter}$-GLP-1 results in an apparent continued glucose suppression after the 4 hour time points relative to the vehicle group.

No adverse effect attributed to compound was observed in these studies.

In sum, the results of this experiment, indicate that the intratracheal administration of mPEGSPC$_{5k}$-N$^{ter}$-GLP-1, a cleavable GLP-1 conjugate, resulted in a statistically significant suppression of blood glucose in a male diabetic mouse (BKS.Cg-+Lepr db/+Lepr db/01aHsd) model.

The foregoing embodiments and advantages are merely exemplary and are not to be construed as limiting the present invention. The description of the present invention is intended to be illustrative, and not to limit the scope of the claims. Many alternatives, modifications, and variations will be apparent to those skilled in the art.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

We claim:

1. A GLP-1 polymer conjugate comprising a GLP-1 moiety attached at its N-terminus to a water-soluble polymer, wherein the conjugate is formed by contacting the GLP-1 moiety with a polymeric reagent of the following structure:

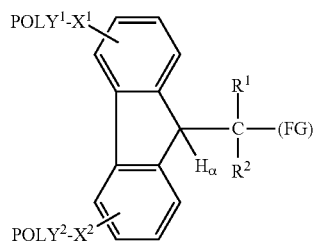

where:
POLY$^1$ is a first water-soluble polymer;
POLY$^2$ is a second water-soluble polymer;
X$^1$ is a first spacer moiety;
X$^2$ is a second spacer moiety;
H$_\alpha$ is an ionizable hydrogen atom;
R$^1$ is H or an organic radical;
R$^2$ is H or an organic radical; and
(FG) is a functional group capable of reacting with an amino group of the GLP-1 moiety to form a degradable carbamate linkage.

2. The GLP-1 polymer conjugate of claim 1, wherein each of the first water-soluble polymer and second water-soluble polymer is independently selected from poly(alkylene glycol), poly(oxyethylated polyol), poly(olefinic alcohol), poly(vinylpyrrolidone), poly(hydroxyalkylmethacrylamide), poly(hydroxyalkylmethacrylate), poly(saccharide), poly(α-hydroxy acid), poly(vinyl alcohol), polyphosphazene, polyoxazoline, poly(N-acryloylmorpholine), and copolymers and terpolymers thereof.

3. The GLP-1 polymer conjugate of claim 2, wherein each of the first water-soluble polymer and second water-soluble polymer is a polyethylene glycol.

4. The GLP-1 polymer conjugate of claim 3, further comprising at least one additional polyethylene glycol attached via a degradable carbamate linkage to a number of sites on the GLP-1 moiety selected from one and two.

5. The GLP-1 polymer conjugate of claim 4, wherein the at least one additional polyethylene glycol is attached via a degradable carbamate linkage to one or more sites corresponding to Lys26 and Lys34 of the GLP-1 moiety of SEQ ID NO: 1.

6. The GLP-1 polymer conjugate of claim 3, wherein the polyethylene glycol is attached via a degradable carbamate linkage to a single site of the GLP-1 moiety.

7. The GLP-1 polymer conjugate of claim 1, wherein each of the first water-soluble polymer and the second water-soluble polymer independently has a molecular weight ranging from about 500 daltons to about 80,000 daltons.

8. The GLP-1 polymer conjugate of claim 7, wherein each of the first water-soluble polymer and the second water-soluble polymer independently has a molecular weight ranging from about 1000 daltons to about 40,000 daltons.

9. The GLP-1 conjugate of claim 1, wherein each of $R^1$ and $R^2$ is H.

* * * * *